US005843460A

United States Patent [19]

Labigne et al.

[11] Patent Number: 5,843,460

[45] Date of Patent: Dec. 1, 1998

[54] IMMUNOGENIC COMPOSITIONS AGAINST HELICOBACTER INFECTION, POLYPEPTIDES FOR USE IN THE COMPOSITIONS, AND NUCLEIC ACID SEQUENCES ENCODING SAID POLYPEPTIDES

[75] Inventors: Agnes Labigne, Bures S/Yvette, France; Sebastin Suerbaum, Bochum, Germany; Richard L. Ferrero, Paris; Jean-Michel Thiberge, Plaisir, both of France

[73] Assignees: Institut Pasteur; Institut National de la Sante et de la Recherche Medicale, both of Paris, France

[21] Appl. No.: 467,822

[22] Filed: Jun. 6, 1995

Related U.S. Application Data

[63] Continuation of Ser. No. 447,177, May 19, 1995, which is a continuation-in-part of Ser. No. 432,697, May 2, 1995.

[30] Foreign Application Priority Data

May 19, 1993 [EP] European Pat. Off. ............ 93 401 309
Nov. 19, 1993 [WO] WIPO ...................... PCT/EP93/03259

[51] Int. Cl.[6] .................................................. A61K 39/02

[52] U.S. Cl. .......................... 424/234.1; 435/7.32; 435/6; 435/7.9; 514/234.5; 514/41

[58] Field of Search .................................. 435/7.32, 4, 6, 435/7.9; 514/234.5, 41; 424/234.1

[56] References Cited

FOREIGN PATENT DOCUMENTS

| | | |
|---|---|---|
| WOA9004030 | 4/1990 | WIPO . |
| WOA9109049 | 6/1991 | WIPO . |
| WOA9307273 | 4/1993 | WIPO . |
| WOA9316723 | 9/1993 | WIPO . |
| WOA9318150 | 9/1993 | WIPO . |
| WOA9320843 | 10/1993 | WIPO . |
| WOA9406474 | 3/1994 | WIPO . |
| WOA9409823 | 5/1994 | WIPO . |
| WOA9503824 | 2/1995 | WIPO . |
| WO 9638475 | 12/1996 | WIPO . |
| WO 9640893 | 12/1996 | WIPO . |

OTHER PUBLICATIONS

R. L. Ferrero et al., "Molecular Evidence Demonstrating Significant Homology Between the Urease Polypeptides of Helicobacter Felis and and Helicobacter Pylori," *Gastroenterology*, vol. 104, No. 4, Apr. 1993, Elsevier, New York, U.S.; p. A699.

E.G. Fox, et al. "Comparison of Two New Immunodiagnostic Assays for Helicobacter Pylori with Established Clinical and Histopathologic Findings", Gastroeneterology, vol. 100, No. 5, Part 2, p. A66.

B.E. Dunn et al., "Identification and Purification of a cpn60 Heat Shock Protein Homolog from Helicobacter Pylori," *Infection and Immunity*, vol. 60, No. 5, May 1992, Am. Soc. Microbiol., Baltimore, US; pp. 1946–1951.

(List continued on next page.)

*Primary Examiner*—James C. Housel
*Assistant Examiner*—Ginny Allen Portner
*Attorney, Agent, or Firm*—Finnegan, Henderson, Farabow, Garrett & Dunner, L.L.P.

[57] ABSTRACT

There is provided an immunogenic composition capable of inducing protective antibodies against Helicobacter infection characterized in that it comprises:

i) at least one sub-unit of a urease structural polypeptide from *Helicobacter pylori* (SEQ ID NOS:22,26), or a fragment thereof, said fragment being recognized by antibodies reacting with *Helicobacter felis* urease (SEQ ID NOS:20–21), and/or at least one sub-unit of a urease structural polypeptide from *Helicobacter felis* (SEQ ID NOS:20–21), or a fragment thereof, said fragment being recognized by antibodies reacting with *Helicobacter pylori* urease (SEQ ID NOS:22–26);

ii) and/or, a heat shock protein (Hsp), or chaperonin, from Helicobacter, or a fragment of said protein.

The preparation, by recombinant means, of such immunogenic compositions is also provided.

10 Claims, 36 Drawing Sheets

OTHER PUBLICATIONS

D.J. Evans et al., "Urease–associated Heat Shock Protein of Helicobacter Pylori," *Infection and Immunity*, vol. 60, No. 5, May 1992, Am. Soc. Microbiol., Baltimore, US; pp. 2125–2127.

P.A. Foxall et al., "Use of Polymerase Chain Reaction–amplified Helicobacter Pylori Urease Structural Genes for Differentiation of Isolates," *J. Clin. Microbiol.*, vol. 30, No. 3, Mar. 1992, Am. Soc. Microbiol, Washington, DC, US; pp. 739–741.

R.L. Ferrero and A. Labigne, "Cloning, Expression, and Sequencing of Helicobacter Felis Urease Genes," *Molec. Microbiol.*, vol. 9, No. 2, 14 Jul. 1993, Blackwell Sci. Pub., Oxford, UK; pp. 323–333.

S. Suerbaum and A. Labigne, "Cloning and Sequencing of the HspA and HspB heat shock protein encoding genes of *Helicobacter pylori*," Abstr. Gen. Meet. Am. Soc. Microbiol., vol. 93, No. O, 19 May 1993, p. 127.

Suerbaum, Sebastian et al., "*Helicobacter pylori* hspA–hspB heat–shock gene cluster: nucleotide sequence, expression, putative function and immunogenicity" Molecular Microbiology (1994) 14(5), 959–974.

Richard L. Ferrero et al., "Recombinant Antigens Prepared from the Urease Subunits of Helicobacter spp.: Evidence of Protection in a Mouse Model of Gastric Infection," Infection and Immunity, Nov. 1994, pp. 4981–4989.

J. Pappo et al., "Effect of Oral Immunization with Recombinant Urease on Murine *Helicobacter felis* Gastritis," Infection and Immunity, Apr. 1995, pp. 1246–1252.

Maurice M. Exner et al., "Isolation and Characterization of a Family of Porin Proteins from *Helicobacter pyroli*," Infection and Immunity, Apr. 1995, pp. 1567–1572.

Allan D. Pronovost et al., "Evaluation of a New Immunodiagnostic Assay for*Helicobacter pylori*Antibody Detection: Correlation with Histopathological and Microbiological Results," Journal of Clinical Microbiology, vol. 32, No. 1, Jan. 1994, pp. 46–50.

Steven J. Czinn et al., "Protection of germ–free mice from infection by *Helicobacter felis* after active oral or passive IgA immunization.", Vaccine, vol. 11, Issue 6, pp. 637–642, 1993.

C. Stewart Goodwin, Overview of *Helicobacter pylori* Gastritis, Peptic Ulcer, and Gastric Cancer and the Possible Development of an *H. Pylori* Vaccine,*Helicobacter pylori*-Biology and Clinical Practice, Chapter 25 pp. 431–444, 1993.

Hu et al, Infection and Immunity, Jul. 1992, pp. 2657–2666, vol. 60(7).

Engstrand et al, Am. J. Gastroenterol. Aug. 1991, vol. 86(8), pp. 976–980.

Chen et al, The Lancet, vol. 339, May 2, 1992, pp. 1120–1121.

Dick–Hegedus et al, Scand. J. Gastroenterol. 1991, vol. 26, pp. 909–915.

Fox et al, Infection and Immunity, vol. 59(3) Mar. 1991, pp. 785–791.

Austin et al, Journal of Bacteriology, Nov. 1992, pp. 7470–7473, vol. 174(22).

Lee et al, Gastroenterology, 1990. vol. 99, pp. 1315–1323.

Czinn et al, Gastroenterology, 102(4 pt 2), p. A611, 1992.

```
1                                       31  S D
TGA TAG CTT GGC TAC CAA TAG AAA TTC AAT AAG GAG TTT AGG ATG AAA CTA ACG CCT AAA
                                                ureA    Met lys leu thr pro lys

61/7                                    91/17
GAA CTA GAC AAG TTA ATG CTC CAT TAT GCG GGC AGA TTG GCA GAA GAA CGC TTG GCG CGT
glu leu asp lys leu met leu his tyr ala gly arg leu ala glu glu arg leu ala arg

121/27                                  151/37
GGT GTG AAA CTC AAT TAC ACC GAA GCG GTC GCG CTC ATT AGC GGG CGT GTG ATG GAA AAG
gly val lys leu asn tyr thr glu ala val ala leu ile ser gly arg val met glu lys

181/47                                  211/57
GCG CGT GAT GGT AAT AAA AGC GTG GCG GAT TTG ATG CAA GAA GGC AGG ACT TGG CTT AAA
ala arg asp gly asn lys ser val ala asp leu met gln glu gly arg thr trp leu lys

241/67                                  271/77
AAA GAA AAT GTG ATG GAC GGC GTA GCA AGC ATG ATT CAT GAA GTG GGG ATT GAA GCT AAC
lys glu asn val met asp gly val ala ser met ile his glu val gly ile glu ala asn

301/87                                  331/97
TTC CCC GAT GGA ACC AAG CTT GTA ACT ATC CAC ACT CCG GTA GAG GAT AAT GGC AAA TTA
phe pro asp gly thr lys leu val thr ile his thr pro val glu asp asn gly lys leu

361/107                                 391/117
GCC CCC GGC GAG GTC TTC TTA AAA AAT GAG GAC ATT ACT ATT AAC GCC GGC AAA GAA GCC
ala pro gly glu val phe leu lys asn glu asp ile thr ile asn ala gly lys glu ala
```

FIG. 3A

```
421/127                                 451/137
ATT AGC TTG AAA GTG AAA AAT AAA GGC GAT CGT CCT GTG CAG GTG GGA TCA CAT TTC CAC

ile ser leu lys val lys asn lys gly asp arg pro val gln val gly ser his phe his

481/147                                 511/157
TTC TTC GAA GTG AAT AAG CTC TTG GAC TTC GAT CGC GCA AAA AGC TTT TGC AAA CGC CTA

phe phe glu val asn lys leu leu asp phe asp arg ala lys ser phe cys lys arg leu

541/167                                 571/177
GAC ATT GCA TCT GGA ACA GCG GTG CGC TTT GAA CCC GGG GAG GAA AAA AGT GTG GAA CTC

asp ile ala ser gly thr ala val arg phe glu pro gly glu glu lys ser val glu leu

601/187                                 631/197
ATT GAC ATC GGC GGG AAT AAG CGC ATC TAT GGC TTT AAT TCT TTG GTG GAT CGC CAA GCC

ile asp ile gly gly asn lys arg ile tyr gly phe asn ser leu val asp arg gln ala

661/207                                 691/217
GAT GCC GAT GGT AAA AAA CTC GGC TTA AAA CGC GCT AAA GAA AAA GGT TTT GGG TCT GTA

asp ala asp gly lys lys leu gly leu lys arg ala lys glu lys gly phe gly ser val

721/227                                 751     S D
AAC TGC GGT TGT GAA GCG ACT AAA GAT AAA CAA TAA GGA AAA ACC ATG AAA AAG ATT TCA
                                            (SEQ. ID NO:20)
asn cys gly cys glu ala thr lys asp lys gln OCH    ureB     Met lys lys ile ser

781/6                                   811/16
CGA AAA GAA TAT GTT TCT ATG TAT GGT CCC ACT ACC GGG GAT CGT GTT AGA CTC GGC GAC

arg lys glu tyr val ser met tyr gly pro thr thr gly asp arg val arg leu gly asp
```

FIG. 3B

```
841/26                                  871/36
ACT GAT TTG ATC TTA GAA GTG GAG CAT GAT TGC ACC ACT TAT GGT GAA GAG ATC AAA TTT
thr asp leu ile leu glu val glu his asp cys thr thr tyr gly glu glu ile lys phe

901/46                                  931/56
GGG GGC GGT AAA ACT ATC CGT GAT GGG ATG AGT CAA ACC AAT AGC CCT AGC TCT TAT GAA
gly gly gly lys thr ile arg asp gly met ser gln thr asn ser pro ser ser tyr glu

961/66                                  991/76
TTA GAT TTG GTG CTC ACT AAC GCC CTC ATT GTG GAC TAT ACG GGC ATT TAC AAA GCC GAC
leu asp leu val leu thr asn ala leu ile val asp tyr thr gly ile tyr lys ala asp

1021/86                                 1051/96
ATT GGG ATT AAA GAC GGC AAG ATT GCA GGC ATT GGC AAG GCA GGC AAT AAG GAC ATG CAA
ile gly ile lys asp gly lys ile ala gly ile gly lys ala gly asn lys asp met gln

1081/106                                1111/116
GAT GGC GTA GAT AAT AAT CTT TGC GTA GGT CCT GCT ACA GAG GCT TTG GCA GCT GAG GGC
asp gly val asp asn asn leu cys val gly pro ala thr glu ala leu ala ala glu gly

1141/26                                 1171/136
TTG ATT GTA ACC GCT GGT GGC ATC GAT ACG CAT ATT CAC TTT ATC TCT CCC CAA CAA ATC
leu ile val thr ala gly gly ile asp thr his ile his phe ile ser pro gln gln ile

1201/146                                1231/156
CCT ACT GCT TTT GCC AGC GGG GTT ACA ACC ATG ATT GGA GGA GGC ACA GGA CCT GCG GAT
pro thr ala phe ala ser gly val thr thr met ile gly gly gly thr gly pro ala asp
```

FIG. 3C

```
1261/166                                1291/176
GGC ACG AAT GCG ACC ACC ATC ACT CCC GGA CGC GCT AAT CTA AAA AGT ATG TTG CGT GCA
gly thr asn ala thr thr ile thr pro gly arg ala asn leu lys ser met leu arg ala
1321/186                                1351/196
GCC GAA GAA TAC GCC ATG AAT CTA GGC TTT TTG GCT AAG GGG AAT GTG TCT TAC GAA CCC
ala glu glu tyr ala met asn leu gly phe leu ala lys gly asn val ser tyr glu pro
1381/206                                1411/216
TCT TTA CGC GAT CAG ATT GAA GCA GGG GCG ATT GGT TTT AAA ATC CAC GAA GAC TGG GGA
ser leu arg asp gln ile glu ala gly ala ile gly phe lys ile his glu asp trp gly
1441/226                                1471/236
AGC ACA CCT GCA GCT ATT CAC CAC TGC CTC AAT GTC GCC GAT GAA TAC GAT GTG CAA GTG
ser thr pro ala ala ile his his cys leu asn val ala asp glu tyr asp val gln val
1501/246                                1531/256
GCT ATC CAC ACC GAT ACC CTT AAC GAG GCG GGC TGT GTA GAA GAC ACC CTA GAG GCG ATT
ala ile his thr asp thr leu asn glu ala gly cys val glu asp thr leu glu ala ile
1561/266                                1591/276
GCC GGG CGC ACC ATC CAT ACC TTC CAC ACT GAA GGG GCT GGG GGT GGA CAC GCT CCA GAT
ala gly arg thr ile his thr phe his thr glu gly ala gly gly gly his ala pro asp
1621/286                                1651/296
GTT ATC AAA ATG GCA GGG GAA TTT AAC ATT CTA CCC GCC TCT ACT AAC CCG ACC ATT CCT
val ile lys met ala gly glu phe asn ile leu pro ala ser thr asn pro thr ile pro
```

FIG. 3D

```
1681/306                                1711/316
TTC ACC AAA AAC ACT GAA GCC GAG CAC ATG GAC ATG TTA ATG GTG TGC CAC CAC TTG GAT

phe thr lys asn thr glu ala glu his met asp met leu met val cys his his leu asp

1741/326                                1771/336
AAA AGT ATC AAG GAA GAT GTG CAG TTT GCC GAT TCG AGG ATT CGC CCC CAA ACT ATC GCG

lys ser ile lys glu asp val gln phe ala asp ser arg ile arg pro gln thr ile ala

1801/346                                1831/356
GCT GAA GAC CAA CTC CAT GAC ATG GGG ATC TTT TCT ATC ACC AGC TCC GAC TCT CAG GCT

ala glu asp gln leu his asp met gly ile phe ser ile thr ser ser asp ser gln ala

1861/366                                1891/376
ATG GGA CGC GTA GGC GAG GTG ATC ACA CGC ACT TGG CAG ACA GCA GAC AAA AAC AAA AAA

met gly arg val gly glu val ile thr arg thr trp gln thr ala asp lys asn lys lys

1921/386                                1951/396
GAG TTT GGG CGC TTG AAA GAG GAA AAA GGC GAT AAC GAC AAC TTC CGC ATC AAA CGC TAC

glu phe gly arg leu lys glu glu lys gly asp asn asp asn phe arg ile lys arg tyr

1981/406                                2011/416
ATC TCT AAA TAC ACC ATC AAC CCC GGG ATC GCG CAT GGG ATT TCT GAC TAT GTG GGC TCT

ile ser lys tyr thr ile asn pro gly ile ala his gly ile ser asp tyr val gly ser

2041/426                                2071/436
GTG GAA GTG GGC AAA TAC GCC GAC CTC GTG CTT TGG AGT CCG GCT TTC TTT GGC ATT AAG

val glu val gly lys tyr ala asp leu val leu trp ser pro ala phe phe gly ile lys
```

FIG. 3E

```
2101/446                                2131/456
CCC AAT ATG ATT ATT AAG GGC GGA TTT ATT GCG CTC TCT CAA ATG GGC GAT GCC AAT
pro asn met ile ile lys gly gly phe ile ala leu ser gln met gly asp ala asn

2161/466                                2191/476
TCT ATT CCC ACC CCT CAG CCC GTC TAT TAC CGT GAA ATG TTT GGA CAC CAT GGG AAA
ser ile pro thr pro gln pro val tyr tyr arg glu met phe gly his his gly lys

2221/486                                2251/496
AAA TTC GAC ACC AAT ATC ACT TTC GTG TCC CAA GCG GCT TAC AAG GCA GGG ATC AAA
lys phe asp thr asn ile thr phe val ser gln ala ala tyr lys ala gly ile lys

2281/506                                2311/516
GAA CTA GGG CTA GAT CGC GCG GCA CCG CCA GTG AAA AAC TGT CGC AAT ATC ACT AAA
glu leu gly leu asp arg ala ala pro pro val lys asn cys arg asn ile thr lys

2341/526                                2371/536
GAC CTC AAA TTC AAC GAT GTG ACC GCA CAT ATT GAT GTC AAC CCT GAA ACC TAT AAG
asp leu lys phe asn asp val thr ala his ile asp val asn pro glu thr tyr lys

2401/546                                2431/556
AAA GTG GAT GGC AAA GAG GTA ACC TCT AAA GCA GCA GAT GAA TTG AGC CTA GCG CAA
lys val asp gly lys glu val thr ser lys ala ala asp glu leu ser leu ala gln
```

FIG. 3F

```
2461/566                                             2491
TAT AAT TTG TTC TAG GAG GCT AAG GAG GGG GAT AGA GGG GGT TAA TTT AGA GGG GAG TCA
                  (SEQ. ID NO:21)
tyr asn leu phe AMB

2521                                                 2551
TTG ATT TAC CTT TGC TAG TTT ATA ATG GAT TTA AGA GAG GTT TTT TTT CGT GTT TTA TAC

2581                                                 2611
CGC GTT GAA ACC CTC AAA TCT TTA CCA AAA GGA TGG TAA (SEQ. ID NO: 19)
```

FIG. 3G

```
                                                                              89
                                                                              89
                                                                              89
                                                                              90

       ureA
       MKLTPKELDKLMLHYAGRLAEERLARGVKLNYTEAVALISGRVMEKARDGNKSVADLMQEGRTWLKKENVMDGVASMIHEVGIEANFPDG
H.f.   ****************E**KKRKEK*I*****V***AHI**E*A*K*TA*E**************L**PDD********M*****
H.p.   ****R*K****L*FT**LV**RR**K*L***P*R******G**E*-*T**Q**S**V*TA*Q**E**PE**KD*QV*CT****
P.p.   ****E**R*K***L*FT**LV**RR**K*L***P*R******G**E*-*T**Q**S**V*TA*Q**E**PE**KD*QV*CT****
J.b.   ****S*R*VE**N**Y**QKR****R***T***ASQI**Y**E*T**Q***Y**E**T**Q***CL*QHL*GRRQ*LPA*PHLLNA*QV**TE****
       ===  =  ===  =   ==    =  =     =    =   =    =   =        =   = =    =    =  =  ==  =

                        FIG. 4A

                                                                              154
                                                                              154
                                                                              51
                                                                              180

       TKLVTIHTPV--------------------EDNGKLAPGEVFLKNEDITI--NAGKEAISLKVKNKGDRPVQVGSHFHFFEVNKLL
H.f.   *****V**I---------------*A*****V**L----*E**K*V*V***I*****C***Y**Y***EA*
H.p.   ****S**S*IV   1  MI****IRVNAALGD*EL***R*TKTIQ*A*H*****R*TKTIQ*A*H*****C***Y**Y***EA*RC*
P.m.   ****S**S*IV 100  ISRENGELQEALFGSLLPVPSLDKFAETKEDNRI****ILCED*CL*L--*I**RK*VI***TS****I****PY*
J.b.   ====  =                 ===                                =  ===      = = ===   ==
       (SEQ ID NO:23)

                        FIG. 4B
```

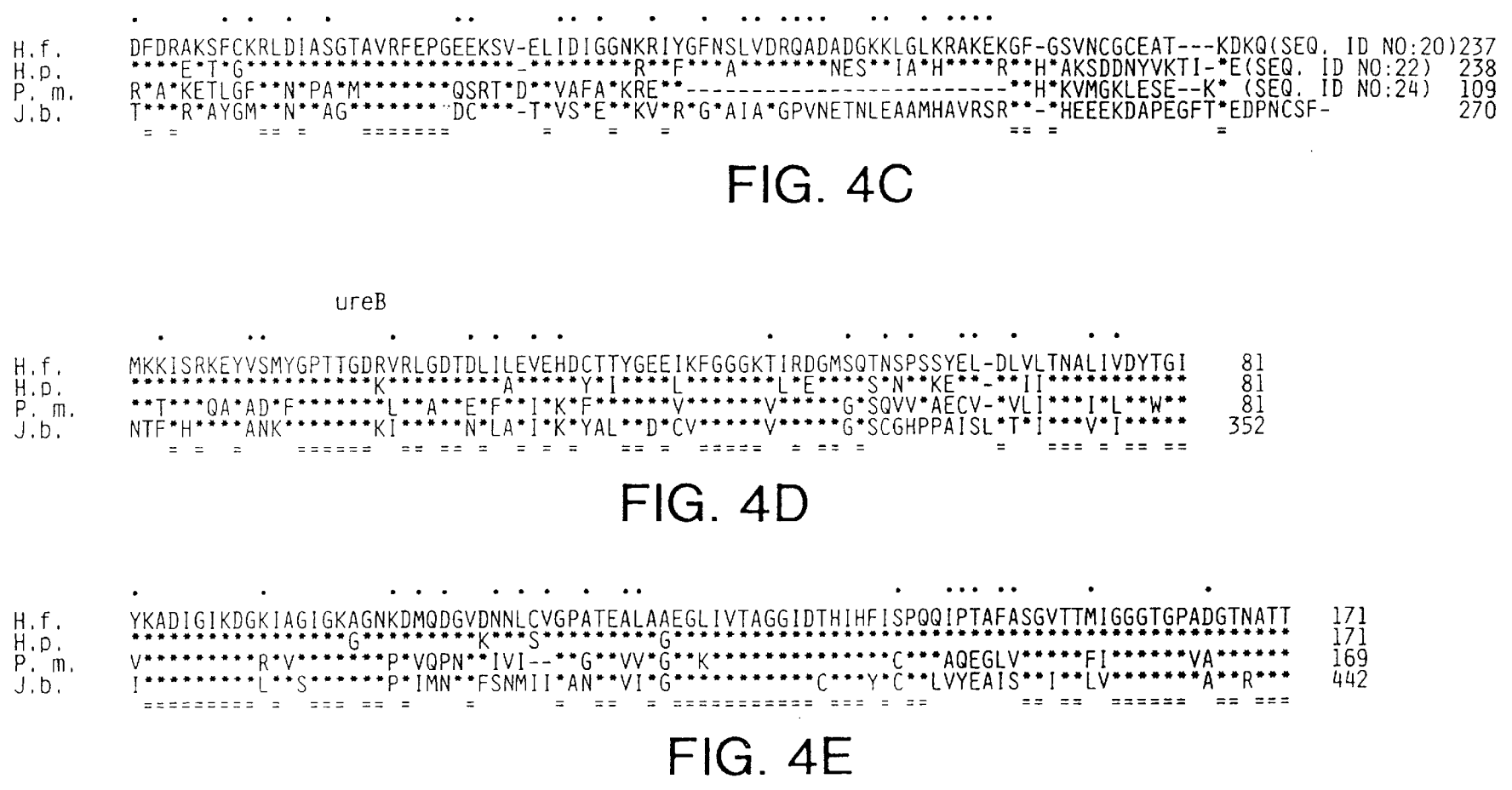

```
H.f.   DFDRAKSFCKRLDIASGTAVRFEPGEEKSV-ELIDIGGNKRIYGFNSLVDRQADADGKKLGLKRAKEKGF-GSVNCGCEAT---KDKQ(SEQ. ID NO:20)237
H.p.   ****E*T*G*********************-*********R**F***A*******NES**IA*H****R**H*AKSDDNYVKTI-*E(SEQ. ID NO:22)  238
P. m.  R*A*KETLGF**N*PA*M*******QSRT*D**VAFA*KRE**--------------------------**H*KVMGKLESE--K* (SEQ. ID NO:24)  109
J.b.   T***R*AYGM**N**AG********DC***-T*VS*E**KV*R*G*AIA*GPVNETNLEAAMHAVRSR**-*HEEEKDAPEGFT*EDPNCSF-            270
```

FIG. 4C ureB

```
H.f.   MKKISRKEYVSMYGPTTGDRVRLGDTDLILEVEHDCTTYGEEIKFGGGKTIRDGMSQTNSPSSYEL-DLVLTNALIVDYTGI    81
H.p.   *******************K*********A*****Y*I****L********L*E****S*N**KE**-**II**********    81
P. m.  **T***QA*AD*F*******L**A**E*F**I*K*F******V*******V******G*SQVV*AECV-*VLI***I*L**W**    81
J.b.   NTF*H****ANK********KI******N*LA*I*K*YAL**D*CV*******V******G*SCGHPPAISL*T*I***V*I******   352
```

FIG. 4D

```
H.f.   YKADIGIKDGKIAGIGKAGNKDMQDGVDNNLCVGPATEALAAEGLIVTAGGIDTHIHFISPQQIPTAFASGVTTMIGGGTGPADGTNATT   171
H.p.   *****************G*********K***S*********G************************************************   171
P. m.  V*********R*V*******P*VQPN**IVI--**G**VV*G**K**************C***AQEGLV*****FI*******VA******   169
J.b.   I*********L**S*******P*IMN**FSNMII*AN**VI*G***********C***Y*C**LVYEAIS**I**LV*********A**R***   442
```

FIG. 4E

```
        .   .  ..   .. . . .  .  ..  .     .  .  .     .                .       .               .  .
H.f.    ITPGRANLKSMLRAAEEYAMNLGFLAKGNVSYEPSLRDQIEAGAIGFKIHEDWGSTPAAIHHCLNVADEYDVQVAIHTDTLNEAGCVEDT   261
H.p.    *****R***W*********S*********A*NDA*A******************T**S**N*A*D***K*********************   261
P. m.   V***IW*MYR**E*VD*LPI*V*LFG**CV*QPEAI*E**T*****L*******A**M***N*******M*******S*****G*FY*E*   259
J.b.    C**SPTQMRL**QSTDDLPL*F**TG**SS*KPDE*HEI*K***M*L*L***********DN**TI*EHH*I*IN**********F**HS   532
         ==       ==       = =   ==  =            === = = ===== == ==   =  =   = =  == ===== =  =
```

FIG. 4F

```
                                    .             . .    ..  .          .  .   .  .    ..
H.f.    LEAIAGRTIHTFHTEGAGGGHAPDVIKMAGEFNILPASTNPTIPETKNTEAEHMDMLMVCHHLDKSIKEDVQFADSRIRPQTIAAEDQLH   351
H.p.    MA*****TM***************I**V***H**************V***************************************T**   351
P. m.   VK*****VI******************SV**P**********M*Y*I**VD**L**********P**P***A**E****RE******I**   349
J.b.    IA*FK**TI**Y*S**********I**VC*IK*V**S*****R*L*S**ID**L**********RE*P***A**H****KK******V**   622
          =  ==  == = ========== ==  =  = == ===== = = == ==========  = === == ====  ======  ==
```

FIG. 4G

```
           ..  .              .          ... .  ....           .                              .
H.f.    DMGIFSITSSDSQAMGRVGEVITRTWQTADKNKKEFGRLKEEKGDNDNFRIKRYISKYTINPGIAHGISDYVGSVEVGKYADLVLWSPAF   441
H.p.    ******************************************************L*******A******E*********V**********   441
P. m.   ***AI*VM**************L****C*H***LQR*T*AGDSA****N******A******AL****AHT***I*K**L**I***D***   439
J.b.    *I*AI**I**************S**********AQT*P**CDSS***********A******A******Q*********L******K*S*   712
        = =  =  ============ ==== = ===   = =      === ======  ======  ====   === = == == === = =
```

FIG. 4H

```
              .      ......   .          .  . . ..     . . .   .  ..  .    . .     .   .   .
H.f.     FGIKPNMIIKGGFIALSQMGDANASIPTPQPVYYREMFGHHGKNKFDTNITFVSQAAYKAGIKEELGLDRAAPPVKN--CRNITKKDLKF   529
H.p.     **V***********************************A****A*Y*R**********DK********E*QVL****--********MQ*   529
P. m.    **V**AL*****MVRYAP***I**A*******H**P*YACL**A*YQ*SMI*M*K*GIEA*VP*K***KSLSLIGRVEGC*H***ASMIH   529
J.b.     **T**E*V****MVAWADI**P**********KM*P*Y*TL**AGGALS*A***K**LDQRVNVLY**NKRVEA*S*--V*KL**L*M*L   800
         == ==   ====       == == =======  = =    =         = = =          ==            =  ==
```

FIG. 4I

```
            ..    .       .   .....     .   .
H.f.     NDVTAHIDVNPETYKVKVDGKEVTSKAADELSLAQLYNLF (SEQ. ID NO:21)  569
H.p.     **T****E******H*F*********P*NKV*****FSI* (SEQ. ID NO:26)  569
P. m.    *NYVP**ELD*Q**I**A**VPLVCEP*T**PM**R*F** (SEQ. ID NO:27)  569
J.b.     **ALPE*T*D**S*T**A***LLCVSE*TTVP*SRN*F** (SEQ. ID NO:25)  840
         =     =   =  = =  ==       =           =
```

```
ureA : 74 % identity        ureB  : 88 % identity
ureA : 46 % identity        ureB  : 62 % identity
ureA : 47 % identity        ureB  : 59 % identity
```

FIG. 4J

```
1                                       31
ACA AAC ATG ATC TCA TAT CAG GGA CTT GTT CGC ACC TTC CCT AAA AAT GCG CTA TAG TTG

61                                      91
TGT CGC TTA AGA ATA CTA AGC GCT AAA TTT CTA TTT TAT TTA TCA AAA CTT AGG AGA ACT

121                                     151/10
GAA ATG AAG TTT CAA CCA TTA GGA GAA AGG GTC TTA GTA GAA AGA CTT GAA GAA GAG AAC
    met lys phe gln pro leu gly glu arg val leu val glu arg leu glu glu glu asn

181/21                                  211/31
AAA ACC AGT TCA GGC ATC ATC ATC CCT GAT AAC GCT AAA GAA AAG CCT TTA ATG GGC GTA
lys thr ser ser gly ile ile ile pro asp asn ala lys glu lys pro leu met gly val

241/41                                  271/51
GTC AAA GCG GTT AGC CAT AAA ATC AGT GAG GGT TGC AAA TGC GTT AAA GAA GGC GAT GTG
val lys ala val ser his lys ile ser glu gly cys lys cys val lys glu gly asp val

301/51                                  331/71
ATC GCT TTT GGC AAA TAC AAA GGC GCA GAA ATC GTT TTA GAT GGC GTT GAA TAC ATG GTG
ile ala phe gly lys tyr lys gly ala glu ile val leu asp gly val glu tyr met val

361/71                                  391/91
CTA GAA CTA GAA GAC ATT CTA GGT ATT GTG GGC TCA GGC TCT TGC TGT CAT ACA GGT AAT
leu glu leu glu asp ile leu gly ile val gly ser gly ser cys cys his thr gly asn

421/91                                  451/111
CAT GAT CAT AAA CAT GCT AAA GAG CAT GAA GCT TGC TGT CAT GAT CAC AAA AAA CAC TAA
his asp his lys his ala lys glu his glu ala cys cys his asp his lys lys his OCH
                                                                (SEQ. ID NO: 29)

481                                     511
AAA ACA TTA TTA TTA AGG ATA CAA AAT GGC AAA AGA
```

FIG. 6A 479 509/2
AAA AAA CAT TAT TAT TAA GGA TAC AAA ATG GCA AAA GAA ATC AAA TTT TCA GAT AGC CGA
met ala lys glu ile lys phe ser asp ser ala 539/12 569/22
AGA AAC CTT TTA TTT GAA GGC GTA AGA CAA CTC CAT GAC GCT GTC AAA GTA ACC ATG GGG
arg asn leu leu phe glu gly val arg gln leu his asp ala val lys val thr met gly 599/32 629/42
CCA AGA GGC AGG AAC GTG TTG ATC CAA AAA AGC TAT GGC GCT CCA AGC ATC ACC AAA GAC
pro arg gly arg asn val leu ile gln lys ser tyr gly ala pro ser ile thr lys asp 659/52 689/62
GGC GTG AGC GTG GCT AAA GAG ATT GAA TTA AGT TGC CCC GTG GCT AAC ATG GGC GCT CAG
gly val ser val ala lys glu ile glu leu ser cys pro val ala asn met gly ala gln 719/72 749/82
CTC GTT AAA GAA GAT GCG AGC AAA ACC GCT GAT GCC GCC GGC GAT GGC ACG ACC ACA GCG
leu val lys glu asp ala ser lys thr ala asp ala ala gly asp gly thr thr thr ala 779/92 809/102
ACC GTG CTG GCT TAT AGC ATT TTT AAA GAG GGC TTG AGG AAT ATC ACG GCT GGG GCT AAC
thr val leu ala tyr ser ile phe lys glu gly leu arg asn ile thr ala gly ala asn 839/112 869/122
CCT ATT GAA GTG AAA CGA GGC ATG GAT AAA GCG CCT GAA GCG ATC ATT AAT GAG CTT AAA
pro ile glu val lys arg gly met asp lys ala pro glu ala ile ile asn glu leu lys 899/132 929/142
AAA GCG AGC AAA AAA GTG GGC GGT AAA GAA GAA ATC ACC CAA GTA GCG ACC ATT TCT GCA
lys ala ser lys lys val gly gly lys glu glu ile thr gln val ala thr ile ser ala

FIG. 6B

```
959/152                                         989/162
AAC TCC GAT CAC AAT ATC GGG AAA CTC ATC GCT GAC GCT ATG GAA AAA GTG GGT AAA GAC
asn ser asp his asn ile gly lys leu ile ala asp ala met glu lys val gly lys asp

1019/172                                        1049/182
GGC GTG ATC ACC GTT GAA GAA GCT AAG GGC ATT GAA GAT GAA TTA GAT GTC GTA GAA GGC
gly val ile thr val glu glu ala lys gly ile glu asp glu leu asp val val glu gly

1079/192                                        1109/202
ATG CAA TTT GAT AGA GGC TAC CTC TCC CCT TAC TTT GTA ACC AAC GCT GAG AAA ATG ACC
met gln phe asp arg gly tyr leu ser pro tyr phe val thr asn ala glu lys met thr

1139/212                                        1169/222
GCT CAA TTG GAT AAC GCT TAC ATC CTT TTA ACG GAT AAA AAA ATC TCT AGC ATG AAA GAC
ala gln leu asp asn ala tyr ile leu leu thr asp lys lys ile ser ser met lys asp

1199/232                                        1229/242
ATT CTC CCG CTA CTA GAA AAA ACC ATG AAA GAG GGC AAA CCG CTT TTA ATC ATC GCT GAA
ile leu pro leu leu glu lys thr met lys glu gly lys pro leu leu ile ile ala glu

1259/252                                        1289/262
GAC ATT GAG GGC GAA GCT TTA ACG ACT CTA GTG GTG AAT AAA TTA AGA GGC GTG TTG AAT
asp ile glu gly glu ala leu thr thr leu val val asn lys leu arg gly val leu asn

1319/272                                        1349/282
ATC GCA GCG GTT AAA GCT CCA GGC TTT GGG GAC AGG AGA AAA GAA ATG CTC AAA GAC ATC
ile ala ala val lys ala pro gly phe gly asp arg arg lys glu met leu lys asp ile
```

FIG. 6C

```
1379/292                                1409/302
GCT GTT TTA ACC GGC GGT CAA GTC ATT AGC GAA GAA TTG GGC TTG AGT CTA GAA AAC GCT
ala val leu thr gly gly gln val ile ser glu glu leu gly leu ser leu glu asn ala

1439/312                                1469/322
GAA GTG GAG TTT TTA GGC AAA GCG AAG ATT GTG ATT GAC AAA GAC AAC ACC ACG ATC GTA
glu val glu phe leu gly lys ala lys ile val ile asp lys asp asn thr thr ile val

1499/332                                1529/342
GAT GGC AAA GGC CAT AGC CAT GAC GTC AAA GAC AGA GTC GCG CAA ATC AAA ACC CAA ATT
asp gly lys gly his ser his asp val lys asp arg val ala gln ile lys thr gln ile

1559/352                                1589/362
GCA AGC ACG ACA AGC GAT TAC GAC AAA GAA AAA TTG CAA GAA AGA TTG GCC AAA CTC TCT
ala ser thr thr ser asp tyr asp lys glu lys leu gln glu arg leu ala lys leu ser

1619/372                                1649/382
GGC GGT GTG GCT GTG ATT AAA GTG GGC GCT GCG AGT GAA GTG GAA ATG AAA GAG AAA AAA
gly gly val ala val ile lys val gly ala ala ser glu val glu met lys glu lys lys

1679/392                                1709/402
GAC CGG GTG GAT GAC GCG TTG AGC GCG ACT AAA GCG GCG GTT GAA GAA GGC ATT GTG ATT
asp arg val asp asp ala leu ser ala thr lys ala ala val glu glu gly ile val ile

1739/412                                1769/422
GGG GGC GGT GCG GCC CTC ATT CGC GCG GCC CAA AAA GTG CAT TTG AAT TTA CAC GAT GAT
gly gly gly ala ala leu ile arg ala ala gln lys val his leu asn leu his asp asp
```

FIG. 6D

```
1799/432                                1829/442
GAA AAA GTG GGC TAT GAA ATC ATC ATG CGC GCC ATT AAA GCC CCA TTA GCT CAA ATC GCT
glu lys val gly tyr glu ile ile met arg ala ile lys ala pro leu ala gln ile ala

1859/452                                1889/462
ATC AAT GCC GGT TAT GAT GGC GGT GTG GTC GTG AAT GAA GTA GAA AAA CAC GAA GGG CAT
ile asn ala gly tyr asp gly gly val val val asn glu val glu lys his glu gly his

1919/472                                1949/482
TTT GGT TTT AAC GCT AGC AAT GGC AAG TAT GTG GAC ATG TTT AAA GAA GGC ATT ATT GAC
phe gly phe asn ala ser asn gly lys tyr val asp met phe lys glu gly ile ile asp

1979/492                                2009/502
CCC TTA AAA GTA GAA AGG ATC GCT TTA CAA AAT GCG GTT TCG GTT TCA AGC CTG CTT TTA
pro leu lys val glu arg ile ala leu gln asn ala val ser val ser ser leu leu leu

2039/512                                2069/522
ACC ACA GAA GCC ACC GTG CAT GAA ATC AAA GAA GAA AAA GCG GCC CCA GCA ATG CCT GAT
thr thr glu ala thr val his glu ile lys glu glu lys ala ala pro ala met pro asp

2099/532                                2129/542
ATG GGT GGC ATG GGC GGA ATG GGA GGC ATG GGC GGC ATG ATG TAA GCC CCC TTG CTT TTT
met gly gly met gly gly met gly gly met gly gly met met OCH
                                                     (SEQ ID NO: 30)
2159                                    2189
GGT ATC ATC TGC TTT TAA AAT CCA TCT TCT AGA ATC CCC CCT TCT AAA ATC CCT TTT TTG

2219                                    2249
GGG GGT GCT TTT GGT TTG ATA AAA CCG CTC GCT TTT AAA AAC GCG CAA CAA AAA ACT CTG

2279
TTA AGC (SEQ. ID NO: 28)
```

FIG. 6E

```
 MAKEIKFSDSARNLLFEGVRQLHDAVKVTMGPRGRNVLIQKSYGAPSITKDGVSVAKEIELSCPVANMGAQLVKEDASKTADAAGDG
 ****LR*G*D**LQMLA**NA*A***Q**********VLE******TV************FEHRFM*****M***V****S*T****
MA**DV**GND**VKMLR**NV*A******L**K****VLD**F***T*********R****EDKFE*****M***V***AN******
MA**N**YNED**KKIHK**KT*AE*****L**K**H*V*D**F*S*QV*****T*******EDKHE*****M***V******K****
 ***T*AYDEE**RG*ER*LNS*A******L**K****VLE*KW***T**N****I******ED*YEKI**E****V*K**D*V****
Y**DV-**GAD**ALMLQ**DL*A***A*****K**T*I*EQ*W*S*KV*****T***S*D*KDKYK*I**K**QDV*NN*NEE****
```

FIG. 7A-1

```
TTTATVLAYSIFKEGLRNITAGANPIEVKRGMDKAPEAIINELKKASKKVGGKEEITQVATISANSDHNIGKLIADAMEKVGKDGVIT
********R**LV**HKAVA**M**MDL***I***VL*VTKK*QAM**PCKDSKA*A**G*******EA**AI**E*******E****
********QA*IT***KAVA**M**MDL***I***VT*AVE***AL*VPCSDSKA*A**G*******ETV*****E**D****E****
********EA*YS*****V******MLD***I***VKVVVD*I**I**P*QHHK**A*********N*AE**N***E*******N*S**
********QALV******VA*****LGL***IE**VDKVTET*L*DA*E*ET**Q*AAT*A***-G*QS**D***E**D***NE****
********R**A***FEK*SK****VEIR**V*L*VD*V*A****Q**P*TTP***A*********G*KE**NI*SD**K***RK****
```

FIG. 7A-2

```
VEEAKGIEDELDVVEGMQFDRGYLSPYFVTNAEKMTAQLDNAYILLTDKKISSMKDILPLLEKTMKEGKPLLIIAEDIEGEALTTLVV
**DGN*L*N**Y***********I****IN*QQN*SCE*EHPF***V***V**IREM*SV**GVA*S*R*********I*****A****
**DGT*LQ******************INKP*TGAVE*ESPF***A*****NIREM**V**AVA*A***********V*****A*A**
******F*TV*******N*N*****S**S**P*TQECV*EE*LV*IY*****GI**F**V*QQVAES*R***************A****
***SNTFGLQ*ELT***R**K**I*G****D**RQE*V*EEP****VSS*V*TV**L******VIQA**S*******V*****S****
*KDG*TLN***EII***K*****I****INTSKGQKCEFQD**V**SE*****IQS*V*A**IANLVLNR*KVGLQVVAVK*PGF**L
```

FIG. 7A-3

```
NKLRGVLNIAAVKAPGFGDRRKEMLKDIAVLTGGQVISEELGLSLENAEVEF-LGKAKI-VIDKDNTTIVDGKGHSHDVKDRVAQIKT
*NM**IVKVC************A**Q***I**K*******I*K***G*TL*D-**S**RI*VT*E****I**E*KATEINA*I***RA
*TI**IVKV*************A**Q***T****T*****I*ME**K*TL*D-**Q**RV**N**T***I**V*EEAAIQG*****RQ
*R**AGFRVC************A**E***I*****L******MK***TTLAM-*****KVIVS*ED****E*L*SKE*IES*CES**K
**I**TFKSV************A**Q*M*I***A******V**T***TDLSL-****RKV*MT**E****E*A*DTDAIAG*****R*
*R*KVG*QVV*V*******N**NQ*K*M*IA***A*FG**GLTLNLEDVQPHD***VGEVIVT**DAMLLK*K*DKAQIEK*IQE*IE
```

FIG. 7A-4

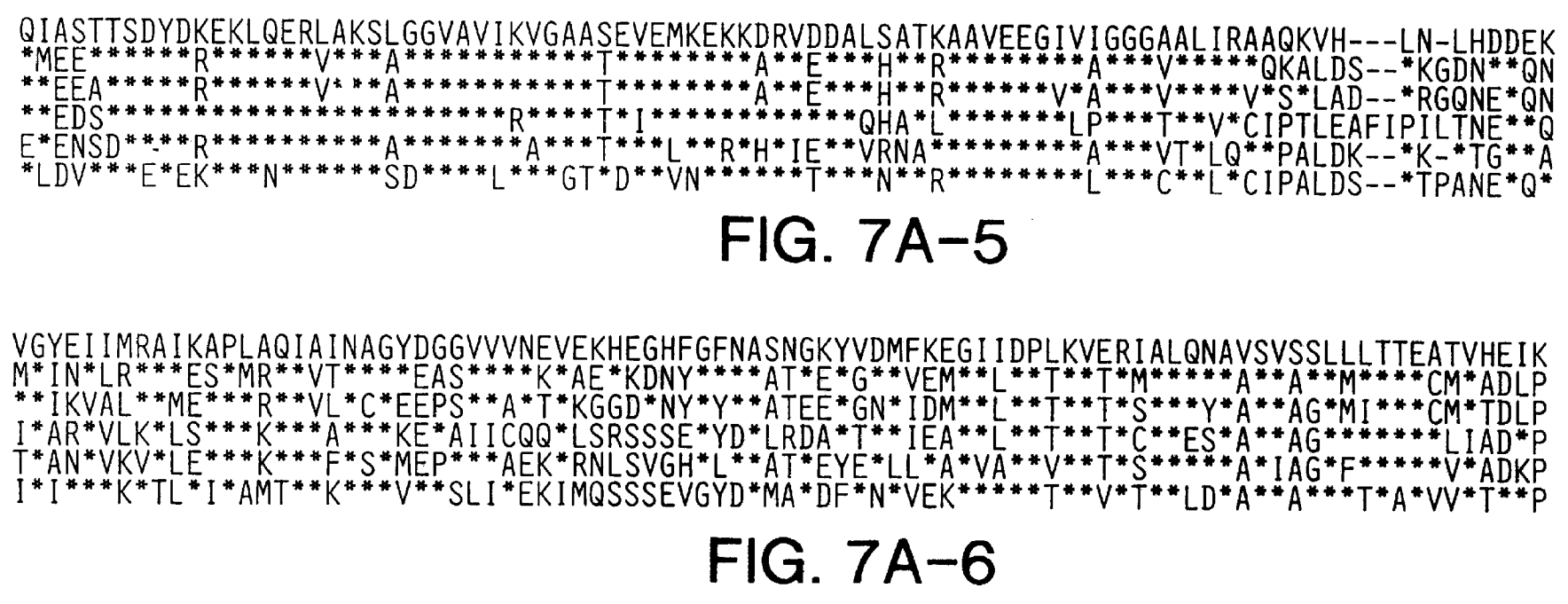

```
QIASTTSDYDKEKLQERLAKSLGGVAVIKVGAASEVEMKEKKDRVDDALSATKAAVEEGIVIGGGAALIRAAQKVH---LN-LHDDEK
*MEE******R******V***A***********T********A**E***H**R*********A***V*****QKALDS--*KGDN**QN
**EEA*****R******V***A***********T********A**E***H**R*******V*A***V****V*S*LAD--*RGQNE*QN
**EDS*********************R****T*I************QHA*L********LP***T**V*CIPTLEAFIPILTNE**Q
E*ENSD**-**R***********A*******A***T***L**R*H*IE**VRNA**********A***VT*LQ**PALDK--*K-*TG**A
*LDV***E*EK***N******SD****L***GT*D**VN******T***N**R**********L***C**L*CIPALDS--*TPANE*Q*
```

FIG. 7A-5

```
VGYEIIMRAIKAPLAQIAINAGYDGGVVVNEVEKHEGHFGFNASNGKYVDMFKEGIIDPLKVERIALQNAVSVSSLLLTTEATVHEIK
M*IN*LR***ES*MR**VT****EAS****K*AE*KDNY****AT*E*G**VEM**L**T**T*M******A**A**M****CM*ADLP
**IKVAL**ME***R**VL*C*EEPS**A*T*KGGD*NY*Y**ATEE*GN*IDM**L**T**T*S***Y*A**AG*MI***CM*TDLP
I*AR*VLK*LS***K***A***KE*AIICQQ*LSRSSSE*YD*LRDA*T**IEA**L**T**T*C**ES*A**AG*******LIAD*P
T*AN*VKV*LE***K***F*S*MEP***AEK*RNLSVGH*L**AT*EYE*LL*A*VA**V**T*S******A*IAG*F*****V*ADKP
I*I***K*TL*I*AMT**K***V**SLI*EKIMQSSSEVGYD*MA*DF*N*VEK******T**V*T**LD*A**A***T*A*VV*T**P
```

FIG. 7A-6

```
                                (SEQ ID NO: 20)
EEKAAPAMPDMGGMGGMGGMGGMM        HspB Helicobacter pylori
                                (SEQ ID NO: 31)
KKEEGVGAG***************        HtpB Legionella pneumophila
                                (SEQ ID NO: 32)
KND**-DLGAA*************        GroEL Escherichia coli
                                (SEQ ID NO: 33)
***SSSA-*A*P*A*-*DY             HypB Chlamydia psittaci
                                (SEQ ID NO: 34)
*KT****SDPTGGMGGMDF             GroEL1 Mycobacterium leprae
                                (SEQ ID NO: 35)
***D-*G*GA******-*-M**G*F       63 kDa Human mitochondrial protein P1

Identity : 62.7%
           60.5%
           59.6%
           57.4%
           42.5%
```

Comparison of the GroEL-like proteins from various bacteria

FIG. 7A-7

```
        Helicobacter pylori          MKFQPLGERVLVERLEEENKTSSGIIIPDNAKEKPLMGVVKAV---SHKI
35%     Mycobacterium leprae             **EDKI**QAG*A*TM*P**LV**ED*****QE*T*V**GPGRWDE
35.6%   Legionella pneumophila       **IR**HD**V*R*M***RT*AG**V***S*T***MR*EII**GAGKVLE
33.8%   Thermophilic bacterium       *LK-***D*IVI*VV*T****A***VL**T*****QE*R*V**GAGRVLD
32.2%   Clostridium perfringens      *SIK***D**VIK***A*ET*K****VTGT***R*QEAE*V**GPGAIVD
20.3%   Escherichia coli             MNIR**HD**I*K*K*V*T*SAG**VLTGS*AA*STR*E*L**GNGRILE
```

FIG. 7B-1

```
SEGCKC---VKEGDVIAFGKYKGAEIVLDGVEYMVLELEDILGIVGSGSCCHTGNHDHKHAKEHEACCHDHKKH (SEQ ID NO: 29)
DGAKRIPVD*S***IVIYS**G*T**KYN*E**LI*SAR*V*AV*SK (SEQ ID NO: 36)
NGDVRA---**V***VL****S*T*V*V**K*LV*MRED**M*VIEK (SEQ ID NO: 37)
NGQRIGRKS-*V**RVI*S**A*T*VKY**K*Y*I*RES***AVIR  (SEQ ID NO: 38)
-GKRTEME-**I**KVLYS**A*T*VKFE*E**TI*RQD***A**E  (SEQ ID NO: 39)
NGEVKP-LD**VG*IVI*NDGY*VKSEKIDN*EVLIMS*SDILAIVEA(SEQ ID NO.40)
```

Comparison of the GroES-like proteins from various bacteria

FIG. 7B-2

```
1/1                                     31/11
ATG TTA GGT CTT GTG TTA TTG TAT GTT GCG GTC GTG CTG ATC AGC AAC GGA GTT AGT GGG
Met leu gly leu val leu leu tyr val ala val val leu ile ser asn gly val ser gly

61/21                                   91/31
CTT GCA AAT GTG GAT GCC AAA AGC AAA GCC ATC ATG AAC TAC TTT GTG GGG GGG GAC TCT
leu ala asn val asp ala lys ser lys ala ile met asn tyr phe val gly gly asp ser

121/41                                  151/51
CCA TTG TGT GTA ATG TGG TCG CTA TCA TCT TAT TCC ACT TTC CAC CCC ACC CCC CCT GCA
pro leu cys val met trp ser leu ser ser tyr ser thr phe his pro thr pro pro ala

181/61                                  211/71
ACT GGT CCA GAA GAT GTC GCG CAG GTG TCT CAA CAC CTC ATT AAC TTC TAT GGT CCA GCG
thr gly pro glu asp val ala gln val ser gln his leu ile asn phe tyr gly pro ala

241/81                                  271/91
ACT GGT CTA TTG TTT GGT TTT ACC TAC TTG TAT GCT GCC ATC AAC AAC ACT TTC AAT CTC
thr gly leu leu phe gly phe thr tyr leu tyr ala ala ile asn asn thr phe asn leu

301/101                                 331/111
GAT TGG AAA CCC TAT GGC TGG TAT TGC TTG TTT GTA ACC ATC AAC ACT ATC CCA GCG GCC
asp trp lys pro tyr gly trp tyr cys leu phe val thr ile asn thr ile pro ala ala

361/121                                 391/131
ATT CTT TCT CAC TAT TCC GAT GCG CTT GAT GAT CAC CGC CTC TTA GGA ATC ACT GAG GGC
ile leu ser his tyr ser asp ala leu asp asp his arg leu leu gly ile thr glu gly

421/141                                 451/151
GAT TGG TGG GCT TTC ATT TGG CTT GCT TGG GGT GTT TTG TGG CTC ACT GGT TGG ATT GAA
asp trp trp ala phe ile trp leu ala trp gly val leu trp leu thr gly trp ile glu

481/161                                 511/171
TGC GCA CTT GGT AAG AGT CTA GGT AAA TTT GTT CCA TGG CTT GCC ATC GTC GAG GGC GTG
cys ala leu gly lys ser leu gly lys phe val pro trp leu ala ile val glu gly val

541/181                                 571/191
ATC ACC GCT TGG ATT CCT GCT TGG CTA CTC TTT ATC CAA CAC TGG TCT TGA (SEQ ID NO: 41)
ile thr ala trp ile pro ala trp leu leu phe ile gln his trp ser OPA (SEQ ID NO: 42)
```

FIG. 9

Comparison of the amino acid sequence of the UreI proteins deduced from the nucleotide sequence of the *ureI* gene of *H. felis* and that of *H. pylori*

Percent Similarity : 88.2

Percent Identity : 73.8

First line : *H. felis* UreI

Second line : *H. pylori* UreI

```
                   .         .         .         .         .
  1    KGWMLGLVLLYVAVVLISNGVSGLANVDAKSKAIMNYFVGGDSPLCVMWS   50
          |||||||||::||||||::||..||:||.|:||:||||  |  :|  :
  1    ...MLGLVLLYVGIVLISNGICGLTKVDPKSTAVMNFFVGGLSIICNV.V   46

                   .         .         .         .         .
 51    LSSYSTFHPTPPATGPEDVAQVSQHLINFYGPATGLLFGFTYLYAAINNT  100
       :  .||.:::||:|..|:||:||||:||.|||||||||||||||||||||:|
 47    VITYSALNPTAPVEGAEDIAQVSHHLTNFYGPATGLLFGFTYLYAAINHT   96

                   .         .         .         .         .
101    FNLDWKPYGWYCLFVTINTIPAAILSHYSDALDDHRLLGITEGDWWAFIW  150
       |.|||:||:||:|||.|||||||||||||| ||||::||||||||||:||
 97    FGLDWRPYSWYSLFVAINTIPAAILSHYSDMLDDHKVLGITEGDWWAIIW  146

                   .         .         .         .         (SEQ. ID NO: 43)
151    LAWGVLWLTGWTECALGKSLGKFVPWLAIVEGVITAWIPAWLLFTQHWS   199
       |||||||||::||  |  .||||.|||||:||::||||||||||||| (SEQ. ID NO:44)
147    LAWGVLWLTAFIENILKIPLGKFTPWLAIIEGILTAWIPAWLLFIQHWV   195
```

FIG. 10

THE GENETIC CODE

| FIRST POSITION (5' END) | SECOND POSITION U | | C | | A | | G | | THIRD POSITION (3' END) |
|---|---|---|---|---|---|---|---|---|---|
| U | UUU | Phe | UCU | Ser | UAU | Tyr | UGU | Cys | U |
| | UUC | | UCC | | UAC | | UGC | | C |
| | UUA | Leu | UCA | | UAA* | Stop | UGA* | Stop | A |
| | UUG | | UCG | | UAG* | Stop | UGG | Trp | G |
| C | CUU | Leu | CCU | Pro | CAU | His | CGU | Arg | U |
| | CUC | | CCC | | CAC | | CGC | | C |
| | CUA | | CCA | | CAA | Gln | CGA | | A |
| | CUG | | CCG | | CAG | | CGG | | G |
| A | AUU | Ile | ACU | Thr | AAU | Asn | AGU | Ser | U |
| | AUC | | ACC | | AAC | | AGC | | C |
| | AUA | | ACA | | AAA | Lys | AGA | Arg | A |
| | AUG* | Met | ACG | | AAG | | AGG | | G |
| G | GUU | Val | GCU | Ala | GAU | Asp | GGU | Gly | U |
| | GUC | | GCC | | GAC | | GGC | | C |
| | GUA | | GCA | | GAA | Glu | GGA | | A |
| | GUG* | | GCG | | GAG | | GGG | | G |

FIG. 11

Abbreviations for amino acids

| *AMINO ACID* | *THREE-LETTER ABBREVIATION* | *ONE-LETTER SYMBOL* |
|---|---|---|
| Alanine | Ala | A |
| Arginine | Arg | R |
| Asparagine | Asn | N |
| Aspartic acid | Asp | D |
| Asparagine or aspartic acid | Asx | B |
| Cysteine | Cys | C |
| Glutamine | Gln | Q |
| Glutamic acid | Glu | E |
| Glutamine or glutamic acid | Glx | Z |
| Glycine | Gly | G |
| Histidine | His | H |
| Isoleucine | Ile | I |
| Leucine | Leu | L |
| Lysine | Lys | K |
| Methionine | Met | M |
| Phenylaianine | Phe | F |
| Proline | Pro | P |
| Serine | Ser | S |
| Threonine | Thr | T |
| Tryptophan | Trp | W |
| Tyrosine | Tyr | Y |
| Valine | Val | V |

FIG. 12

SEQUENCE LISTING ( 1 ) GENERAL INFORMATION:

( i i i ) NUMBER OF SEQUENCES: 44

( 2 ) INFORMATION FOR SEQ ID NO:1:

( i ) SEQUENCE CHARACTERISTICS:
( A ) LENGTH: 27 amino acids
( B ) TYPE: amino acid
( C ) STRANDEDNESS: unknown
( D ) TOPOLOGY: linear ( i i ) MOLECULE TYPE: protein ( x i ) SEQUENCE DESCRIPTION: SEQ ID NO:1:

```
Gly Ser Cys Cys His Thr Gly Asn His Asp His Lys His Ala Lys Glu
1               5                   10                  15

His Glu Ala Cys Cys His Asp His Lys Lys His
            20                  25
```

( 2 ) INFORMATION FOR SEQ ID NO:2:

( i ) SEQUENCE CHARACTERISTICS:
( A ) LENGTH: 27 base pairs
( B ) TYPE: nucleic acid
( C ) STRANDEDNESS: single
( D ) TOPOLOGY: linear ( i i ) MOLECULE TYPE: DNA (genomic)

( i x ) FEATURE:
( A ) NAME/KEY: misc_feature
( B ) LOCATION: one-of(6, 15, 24)
( D ) OTHER INFORMATION: /note= "N=(A or C or g or T/U) or (unknown or other)."

( i x ) FEATURE:
( A ) NAME/KEY: misc_feature
( B ) LOCATION: one-of(9, 12, 21)
( D ) OTHER INFORMATION: /note= "R=A or G."

( i x ) FEATURE:
( A ) NAME/KEY: misc_feature
( B ) LOCATION: one-of(13, 18, 22)
( D ) OTHER INFORMATION: /note= "Y=C or T/U."

( x i ) SEQUENCE DESCRIPTION: SEQ ID NO:2:

```
CAUCCNAARG ARYTNGAYAA RYTNATG                                   27
```

( 2 ) INFORMATION FOR SEQ ID NO:3:

( i ) SEQUENCE CHARACTERISTICS:
( A ) LENGTH: 30 base pairs
( B ) TYPE: nucleic acid
( C ) STRANDEDNESS: single
( D ) TOPOLOGY: linear ( i i ) MOLECULE TYPE: DNA (genomic)

( i x ) FEATURE:
( A ) NAME/KEY: misc_feature
( B ) LOCATION: one-of(1, 4, 19)
( D ) OTHER INFORMATION: /note= "Y=C or T/U."

( i x ) FEATURE:
( A ) NAME/KEY: misc_feature
( B ) LOCATION: one-of(7, 10, 13)
( D ) OTHER INFORMATION: /note= "N=(A or C or G or T/U) or (unknown or other)."

( i x ) FEATURE:
( A ) NAME/KEY: misc_feature
( B ) LOCATION: one-of(14)
( D ) OTHER INFORMATION: /note= "S= C or G."

( i x ) FEATURE:
( A ) NAME/KEY: misc_feature
( B ) LOCATION: one-of(15)
( D ) OTHER INFORMATION: /note= "W=A or T/U."

( x i ) SEQUENCE DESCRIPTION: SEQ ID NO:3:

YTCYTTNCGN CGNSWDATYT TYTTCATCUA 30

( 2 ) INFORMATION FOR SEQ ID NO:4:

( i ) SEQUENCE CHARACTERISTICS:
( A ) LENGTH: 38 base pairs
( B ) TYPE: nucleic acid
( C ) STRANDEDNESS: single
( D ) TOPOLOGY: linear ( i i ) MOLECULE TYPE: DNA (genomic)

( i x ) FEATURE:
( A ) NAME/KEY: misc_feature
( B ) LOCATION: 6..11
( D ) OTHER INFORMATION: /note= "Restriction site introduced in the amplified fragment (EcoRI)."

( x i ) SEQUENCE DESCRIPTION: SEQ ID NO:4:

CCGGAGAATT CATTAGCAGA AAAGAATATG TTTCTATG 38

( 2 ) INFORMATION FOR SEQ ID NO:5:

( i ) SEQUENCE CHARACTERISTICS:
( A ) LENGTH: 38 base pairs
( B ) TYPE: nucleic acid
( C ) STRANDEDNESS: single
( D ) TOPOLOGY: linear ( i i ) MOLECULE TYPE: DNA (genomic)

( i x ) FEATURE:
( A ) NAME/KEY: misc_feature
( B ) LOCATION: 6..11
( D ) OTHER INFORMATION: /note= "Restriction site introduced in the amplified fragment (PstI)."

( x i ) SEQUENCE DESCRIPTION: SEQ ID NO:5:

ACGTTCTGCA GCTTACGAAT AACTTTTGTT GCTTGAGC 38

( 2 ) INFORMATION FOR SEQ ID NO:6:

( i ) SEQUENCE CHARACTERISTICS:

( A ) LENGTH: 20 base pairs
( B ) TYPE: nucleic acid
( C ) STRANDEDNESS: single
( D ) TOPOLOGY: linear ( i i ) MOLECULE TYPE: DNA (genomic)

( i x ) FEATURE:
( A ) NAME/KEY: misc_feature
( B ) LOCATION: 1..6
( D ) OTHER INFORMATION: /note= "Restriction site introduced in the amplified fragment (BamHI)."

( x i ) SEQUENCE DESCRIPTION: SEQ ID NO:6:

GGATCCAAAA AGATTTCACG 20

( 2 ) INFORMATION FOR SEQ ID NO:7:

( i ) SEQUENCE CHARACTERISTICS:
( A ) LENGTH: 30 base pairs
( B ) TYPE: nucleic acid
( C ) STRANDEDNESS: single
( D ) TOPOLOGY: linear ( i i ) MOLECULE TYPE: DNA (genomic)

( i x ) FEATURE:
( A ) NAME/KEY: misc_feature
( B ) LOCATION: 3..8
( D ) OTHER INFORMATION: /note= "Restriction site introduced in the amplified fragment (HindIII)."

( i x ) FEATURE:
( A ) NAME/KEY: misc_feature
( B ) LOCATION: 9..14
( D ) OTHER INFORMATION: /note= "Restriction site introduced in the amplified fragment (PstI)."

( x i ) SEQUENCE DESCRIPTION: SEQ ID NO:7:

GGAAGCTTCT GCAGGTGTGC TTCCCCAGTC 30

( 2 ) INFORMATION FOR SEQ ID NO:8:

( i ) SEQUENCE CHARACTERISTICS:
( A ) LENGTH: 22 base pairs
( B ) TYPE: nucleic acid
( C ) STRANDEDNESS: single
( D ) TOPOLOGY: linear ( i i ) MOLECULE TYPE: DNA (genomic)

( i x ) FEATURE:
( A ) NAME/KEY: misc_feature
( B ) LOCATION: one-of(3, 21)
( D ) OTHER INFORMATION: /note= "N=the four nucleotides"

( i x ) FEATURE:
( A ) NAME/KEY: misc_feature
( B ) LOCATION: one-of(6, 9, 15)
( D ) OTHER INFORMATION: /note= "R= A and G."

( i x ) FEATURE:
( A ) NAME/KEY: misc_feature
( B ) LOCATION: one-of(18)
( D ) OTHER INFORMATION: /note= "Y= T and C."

( i x ) FEATURE:
( A ) NAME/KEY: misc_feature
( B ) LOCATION: one-of(12)
( D ) OTHER INFORMATION: /note= "H= T, C, and A."

( x i ) SEQUENCE DESCRIPTION: SEQ ID NO:8:

GCNAARGARA THAARTTYTC NG 22

( 2 ) INFORMATION FOR SEQ ID NO:9:

( i ) SEQUENCE CHARACTERISTICS:
( A ) LENGTH: 8 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:9:

Ala Lys Glu Ile Lys Phe Ser Asp
1 5

( 2 ) INFORMATION FOR SEQ ID NO:10:

( i ) SEQUENCE CHARACTERISTICS:
( A ) LENGTH: 22 base pairs
( B ) TYPE: nucleic acid
( C ) STRANDEDNESS: single
( D ) TOPOLOGY: linear ( i i ) MOLECULE TYPE: DNA (genomic)

( i x ) FEATURE:
( A ) NAME/KEY: misc_feature
( B ) LOCATION: one-of(7, 13)
( D ) OTHER INFORMATION: /note= "K= G and T."

( x i ) SEQUENCE DESCRIPTION: SEQ ID NO:10:

CRTTNCKNCC NCKNGGNCCC AT 22

( 2 ) INFORMATION FOR SEQ ID NO:11:

( i ) SEQUENCE CHARACTERISTICS:
( A ) LENGTH: 8 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:11:

Met Gly Pro Arg Gly Arg Asn Val
1 5

( 2 ) INFORMATION FOR SEQ ID NO:12:

( i ) SEQUENCE CHARACTERISTICS:
( A ) LENGTH: 14 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:12:

Met Gly Gly Met Gly Gly Met Gly Gly Met Gly Gly Met Met
1 5 10

( 2 ) INFORMATION FOR SEQ ID NO:13:

( i ) SEQUENCE CHARACTERISTICS:
( A ) LENGTH: 16 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:13:

-continued

C T T G T T C G C A   C C T T C C   1 6

( 2 ) INFORMATION FOR SEQ ID NO:14:

( i ) SEQUENCE CHARACTERISTICS:
( A ) LENGTH: 13 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:14:

T A A C T C G C T T   G A A   1 3

( 2 ) INFORMATION FOR SEQ ID NO:15:

( i ) SEQUENCE CHARACTERISTICS:
( A ) LENGTH: 38 base pairs
( B ) TYPE: nucleic acid
( C ) STRANDEDNESS: single
( D ) TOPOLOGY: linear ( i i ) MOLECULE TYPE: DNA (genomic)

( i x ) FEATURE:
( A ) NAME/KEY: misc_feature
( B ) LOCATION: 6..11
( D ) OTHER INFORMATION: /note= "Restriction site EcoRI."

( x i ) SEQUENCE DESCRIPTION: SEQ ID NO:15:

C C G G A G A A T T   C A A G T T T C A A   C C A T T A G G A G   A A A G G G T C   3 8

( 2 ) INFORMATION FOR SEQ ID NO:16:

( i ) SEQUENCE CHARACTERISTICS:
( A ) LENGTH: 38 base pairs
( B ) TYPE: nucleic acid
( C ) STRANDEDNESS: single
( D ) TOPOLOGY: linear ( i i ) MOLECULE TYPE: DNA (genomic)

( i x ) FEATURE:
( A ) NAME/KEY: misc_feature
( B ) LOCATION: 6..11
( D ) OTHER INFORMATION: /note= "Restriction site PstI."

( x i ) SEQUENCE DESCRIPTION: SEQ ID NO:16:

A C G T T C T G C A   G T T T A G T G T T   T T T T G T G A T C   A T G A C A G C   3 8

( 2 ) INFORMATION FOR SEQ ID NO:17:

( i ) SEQUENCE CHARACTERISTICS:
( A ) LENGTH: 38 base pairs
( B ) TYPE: nucleic acid
( C ) STRANDEDNESS: single
( D ) TOPOLOGY: linear ( i i ) MOLECULE TYPE: DNA (genomic)

( i x ) FEATURE:
( A ) NAME/KEY: misc_feature
( B ) LOCATION: 6..11
( D ) OTHER INFORMATION: /note= "Restriction site EcoRI."

( x i ) SEQUENCE DESCRIPTION: SEQ ID NO:17:

C C G G A G A A T T   C G C A A A A G A A   A T C A A A T T T T   C A G A T A G C   3 8

( 2 ) INFORMATION FOR SEQ ID NO:18:

-continued ( i ) SEQUENCE CHARACTERISTICS:
( A ) LENGTH: 38 base pairs
( B ) TYPE: nucleic acid
( C ) STRANDEDNESS: single
( D ) TOPOLOGY: linear ( i i ) MOLECULE TYPE: DNA (genomic)

( i x ) FEATURE:
( A ) NAME/KEY: misc_feature
( B ) LOCATION: 6..11
( D ) OTHER INFORMATION: /note= "Restriction site PstI."

( x i ) SEQUENCE DESCRIPTION: SEQ ID NO:18:

ACGTTCTGCA GATGATACCA AAAAGCAAGG GGGCTTAC 38

( 2 ) INFORMATION FOR SEQ ID NO:19:

( i ) SEQUENCE CHARACTERISTICS:
( A ) LENGTH: 2619 base pairs
( B ) TYPE: nucleic acid
( C ) STRANDEDNESS: double
( D ) TOPOLOGY: linear ( i i ) MOLECULE TYPE: DNA (genomic)

( i x ) FEATURE:
( A ) NAME/KEY: misc_feature
( B ) LOCATION: 31..36
( D ) OTHER INFORMATION: /standard_name= "Shine-Dalgarno sequence."

( i x ) FEATURE:
( A ) NAME/KEY: misc_feature
( B ) LOCATION: 756..759
( D ) OTHER INFORMATION: /standard_name= "Shine-Dalgarno sequence."

( x i ) SEQUENCE DESCRIPTION: SEQ ID NO:19:

TGATAGCTTG GCTACCAATA GAAATTCAAT AAGGAGTTTA GGATGAAACT AACGCCTAAA 60

GAACTAGACA AGTTAATGCT CCATTATGCG GGCAGATTGG CAGAAGAACG CTTGGCGCGT 120

GGTGTGAAAC TCAATTACAC CGAAGCGGTC GCGCTCATTA GCGGGCGTGT GATGGAAAAG 180

GCGCGTGATG GTAATAAAAG CGTGGCGGAT TTGATGCAAG AAGGCAGGAC TTGGCTTAAA 240

AAAGAAAATG TGATGGACGG CGTAGCAAGC ATGATTCATG AAGTGGGGAT TGAAGCTAAC 300

TTCCCCGATG GAACCAAGCT TGTAACTATC CACACTCCGG TAGAGGATAA TGGCAAATTA 360

GCCCCCGGCG AGGTCTTCTT AAAAAATGAG GACATTACTA TTAACGCCGG CAAAGAAGCC 420

ATTAGCTTGA AAGTGAAAAA TAAAGGCGAT CGTCCTGTGC AGGTGGGATC ACATTTCCAC 480

TTCTTCGAAG TGAATAAGCT CTTGGACTTC GATCGCGCAA AAAGCTTTTG CAAACGCCTA 540

GACATTGCAT CTGGAACAGC GGTGCGCTTT GAACCCGGGG AGGAAAAAAG TGTGGAACTC 600

ATTGACATCG GCGGGAATAA GCGCATCTAT GGCTTTAATT CTTTGGTGGA TCGCCAAGCC 660

GATGCCGATG GTAAAAAACT CGGCTTAAAA CGCGCTAAAG AAAAAGGTTT TGGGTCTGTA 720

AACTGCGGTT GTGAAGCGAC TAAAGATAAA CAATAAGGAA AAACCATGAA AAAGATTTCA 780

CGAAAAGAAT ATGTTTCTAT GTATGGTCCC ACTACCGGGG ATCGTGTTAG ACTCGGCGAC 840

ACTGATTTGA TCTTAGAAGT GGAGCATGAT TGCACCACTT ATGGTGAAGA GATCAAATTT 900

GGGGGCGGTA AAACTATCCG TGATGGGATG AGTCAAACCA ATAGCCCTAG CTCTTATGAA 960

TTAGATTTGG TGCTCACTAA CGCCCTCATT GTGGACTATA CGGGCATTTA CAAAGCCGAC 1020

ATTGGGATTA AAGACGGCAA GATTGCAGGC ATTGGCAAGG CAGGCAATAA GGACATGCAA 1080

GATGGCGTAG ATAATAATCT TTGCGTAGGT CCTGCTACAG AGGCTTTGGC AGCTGAGGGC 1140

-continued

```
TTGATTGTAA CCGCTGGTGG CATCGATACG CATATTCACT TTATCTCTCC CCAACAAATC   1200
CCTACTGCTT TTGCCAGCGG GGTTACAACC ATGATTGGAG GAGGCACAGG ACCTGCGGAT   1260
GGCACGAATG CGACCACCAT CACTCCCGGA CGCGCTAATC TAAAAAGTAT GTTGCGTGCA   1320
GCCGAAGAAT ACGCCATGAA TCTAGGCTTT TTGGCTAAGG GGAATGTGTC TTACGAACCC   1380
TCTTTACGCG ATCAGATTGA AGCAGGGGCG ATTGGTTTTA AAATCCACGA AGACTGGGGA   1440
AGCACACCTG CAGCTATTCA CCACTGCCTC AATGTCGCCG ATGAATACGA TGTGCAAGTG   1500
GCTATCCACA CCGATACCCT TAACGAGGCG GGCTGTGTAG AAGACACCCT AGAGGCGATT   1560
GCCGGGCGCA CCATCCATAC CTTCCACACT GAAGGGGCTG GGGGTGGACA CGCTCCAGAT   1620
GTTATCAAAA TGGCAGGGGA ATTTAACATT CTACCCGCCT CTACTAACCC GACCATTCCT   1680
TTCACCAAAA ACACTGAAGC CGAGCACATG GACATGTTAA TGGTGTGCCA CCACTTGGAT   1740
AAAAGTATCA AGGAAGATGT GCAGTTTGCC GATTCGAGGA TTCGCCCCCA AACTATCGCG   1800
GCTGAAGACC AACTCCATGA CATGGGGATC TTTTCTATCA CCAGCTCCGA CTCTCAGGCT   1860
ATGGGACGCG TAGGCGAGGT GATCACACGC ACTTGGCAGA CAGCAGACAA AAACAAAAAA   1920
GAGTTTGGGC GCTTGAAAGA GGAAAAAGGC GATAACGACA ACTTCCGCAT CAAACGCTAC   1980
ATCTCTAAAT ACACCATCAA CCCCGGGATC GCGCATGGGA TTTCTGACTA TGTGGGCTCT   2040
GTGGAAGTGG GCAAATACGC CGACCTCGTG CTTTGGAGTC CGGCTTTCTT TGGCATTAAG   2100
CCCAATATGA TTATTAAGGG CGGATTTATT GCGCTCTCTC AAATGGGCGA TGCCAATGCG   2160
TCTATTCCCA CCCCTCAGCC CGTCTATTAC CGTGAAATGT TTGGACACCA TGGGAAAAAC   2220
AAATTCGACA CCAATATCAC TTTCGTGTCC CAAGCGGCTT ACAAGGCAGG GATCAAAGAA   2280
GAACTAGGGC TAGATCGCGC GGCACCGCCA GTGAAAAACT GTCGCAATAT CACTAAAAAG   2340
GACCTCAAAT TCAACGATGT GACCGCACAT ATTGATGTCA ACCCTGAAAC CTATAAGGTG   2400
AAAGTGGATG GCAAAGAGGT AACCTCTAAA GCAGCAGATG AATTGAGCCT AGCGCAACTT   2460
TATAATTTGT TCTAGGAGGC TAAGGAGGGG GATAGAGGGG GTTAATTTAG AGGGGAGTCA   2520
TTGATTTACC TTTGCTAGTT TATAATGGAT TTAAGAGAGG TTTTTTTTCG TGTTTTATAC   2580
CGCGTTGAAA CCCTCAAATC TTTACCAAAA GGATGGTAA                          2619
```

( 2 ) INFORMATION FOR SEQ ID NO:20:

( i ) SEQUENCE CHARACTERISTICS:
( A ) LENGTH: 237 amino acids
( B ) TYPE: amino acid
( C ) STRANDEDNESS: single
( D ) TOPOLOGY: linear ( i i ) MOLECULE TYPE: peptide ( i x ) FEATURE:
( A ) NAME/KEY: Protein
( B ) LOCATION: 1..237
( D ) OTHER INFORMATION: /note= "URE A - FIGURE 3."

( x i ) SEQUENCE DESCRIPTION: SEQ ID NO:20:

```
Met Lys Leu Thr Pro Lys Glu Leu Asp Lys Leu Met Leu His Tyr Ala
1               5                   10                  15

Gly Arg Leu Ala Glu Glu Arg Leu Ala Arg Gly Val Lys Leu Asn Tyr
            20                  25                  30

Thr Glu Ala Val Ala Leu Ile Ser Gly Arg Val Met Glu Lys Ala Arg
        35                  40                  45

Asp Gly Asn Lys Ser Val Ala Asp Leu Met Gln Glu Gly Arg Thr Trp
    50                  55                  60
```

| | | | | | | | | | | | | | | |
|---|---|---|---|---|---|---|---|---|---|---|---|---|---|---|
| Leu | Lys | Lys | Glu | Asn | Val | Met | Asp | Gly | Val | Ala | Ser | Met | Ile | His | Glu |
| 65 | | | | | 70 | | | | 75 | | | | | | 80 |
| Val | Gly | Ile | Glu | Ala | Asn | Phe | Pro | Asp | Gly | Thr | Lys | Leu | Val | Thr | Ile |
| | | | | 85 | | | | | 90 | | | | | 95 | |
| His | Thr | Pro | Val | Glu | Asp | Asn | Gly | Lys | Leu | Ala | Pro | Gly | Glu | Val | Phe |
| | | | 100 | | | | | 105 | | | | | 110 | | |
| Leu | Lys | Asn | Glu | Asp | Ile | Thr | Ile | Asn | Ala | Gly | Lys | Glu | Ala | Ile | Ser |
| | | 115 | | | | | 120 | | | | | 125 | | | |
| Leu | Lys | Val | Lys | Asn | Lys | Gly | Asp | Arg | Pro | Val | Gln | Val | Gly | Ser | His |
| | 130 | | | | | 135 | | | | | 140 | | | | |
| Phe | His | Phe | Phe | Glu | Val | Asn | Lys | Leu | Leu | Asp | Phe | Asp | Arg | Ala | Lys |
| 145 | | | | | 150 | | | | | 155 | | | | | 160 |
| Ser | Phe | Cys | Lys | Arg | Leu | Asp | Ile | Ala | Ser | Gly | Thr | Ala | Val | Arg | Phe |
| | | | | 165 | | | | | 170 | | | | | 175 | |
| Glu | Pro | Gly | Glu | Glu | Lys | Ser | Val | Glu | Leu | Ile | Asp | Ile | Gly | Gly | Asn |
| | | | 180 | | | | | 185 | | | | | 190 | | |
| Lys | Arg | Ile | Tyr | Gly | Phe | Asn | Ser | Leu | Val | Asp | Arg | Gln | Ala | Asp | Ala |
| | | 195 | | | | | 200 | | | | | 205 | | | |
| Asp | Gly | Lys | Lys | Leu | Gly | Leu | Lys | Arg | Ala | Lys | Glu | Lys | Gly | Phe | Gly |
| | 210 | | | | | 215 | | | | | 220 | | | | |
| Ser | Val | Asn | Cys | Gly | Cys | Glu | Ala | Thr | Lys | Asp | Lys | Gln | | | |
| 225 | | | | | 230 | | | | | 235 | | | | | |

( 2 ) INFORMATION FOR SEQ ID NO:21:

( i ) SEQUENCE CHARACTERISTICS:
        ( A ) LENGTH: 569 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Protein
        ( B ) LOCATION: 1..569
        ( D ) OTHER INFORMATION: /note= "URE B - FIGURE 3."

( x i ) SEQUENCE DESCRIPTION: SEQ ID NO:21:

| | | | | | | | | | | | | | | | |
|---|---|---|---|---|---|---|---|---|---|---|---|---|---|---|---|
| Met | Lys | Lys | Ile | Ser | Arg | Lys | Glu | Tyr | Val | Ser | Met | Tyr | Gly | Pro | Thr |
| 1 | | | | 5 | | | | | 10 | | | | | 15 | |
| Thr | Gly | Asp | Arg | Val | Arg | Leu | Gly | Asp | Thr | Asp | Leu | Ile | Leu | Glu | Val |
| | | | 20 | | | | | 25 | | | | | 30 | | |
| Glu | His | Asp | Cys | Thr | Thr | Tyr | Gly | Glu | Glu | Ile | Lys | Phe | Gly | Gly | Gly |
| | | 35 | | | | | 40 | | | | | 45 | | | |
| Lys | Thr | Ile | Arg | Asp | Gly | Met | Ser | Gln | Thr | Asn | Ser | Pro | Ser | Ser | Tyr |
| | 50 | | | | | 55 | | | | | 60 | | | | |
| Glu | Leu | Asp | Leu | Val | Leu | Thr | Asn | Ala | Leu | Ile | Val | Asp | Tyr | Thr | Gly |
| 65 | | | | | 70 | | | | | 75 | | | | | 80 |
| Ile | Tyr | Lys | Ala | Asp | Ile | Gly | Ile | Lys | Asp | Gly | Lys | Ile | Ala | Gly | Ile |
| | | | | 85 | | | | | 90 | | | | | 95 | |
| Gly | Lys | Ala | Gly | Asn | Lys | Asp | Met | Gln | Asp | Gly | Val | Asp | Asn | Asn | Leu |
| | | | 100 | | | | | 105 | | | | | 110 | | |
| Cys | Val | Gly | Pro | Ala | Thr | Glu | Ala | Leu | Ala | Ala | Glu | Gly | Leu | Ile | Val |
| | | 115 | | | | | 120 | | | | | 125 | | | |
| Thr | Ala | Gly | Gly | Ile | Asp | Thr | His | Ile | His | Phe | Ile | Ser | Pro | Gln | Gln |
| | 130 | | | | | 135 | | | | | 140 | | | | |
| Ile | Pro | Thr | Ala | Phe | Ala | Ser | Gly | Val | Thr | Thr | Met | Ile | Gly | Gly | Gly |
| 145 | | | | | 150 | | | | | 155 | | | | | 160 |

-continued

```
Thr Gly Pro Ala Asp Gly Thr Asn Ala Thr Thr Ile Thr Pro Gly Arg
                165                 170                 175

Ala Asn Leu Lys Ser Met Leu Arg Ala Ala Glu Glu Tyr Ala Met Asn
            180                 185                 190

Leu Gly Phe Leu Ala Lys Gly Asn Val Ser Tyr Glu Pro Ser Leu Arg
        195                 200                 205

Asp Gln Ile Glu Ala Gly Ala Ile Gly Phe Lys Ile His Glu Asp Trp
    210                 215                 220

Gly Ser Thr Pro Ala Ala Ile His His Cys Leu Asn Val Ala Asp Glu
225                 230                 235                 240

Tyr Asp Val Gln Val Ala Ile His Thr Asp Thr Leu Asn Glu Ala Gly
                245                 250                 255

Cys Val Glu Asp Thr Leu Glu Ala Ile Ala Gly Arg Thr Ile His Thr
            260                 265                 270

Phe His Thr Glu Gly Ala Gly Gly Gly His Ala Pro Asp Val Ile Lys
        275                 280                 285

Met Ala Gly Glu Phe Asn Ile Leu Pro Ala Ser Thr Asn Pro Thr Ile
    290                 295                 300

Pro Phe Thr Lys Asn Thr Glu Ala Glu His Met Asp Met Leu Met Val
305                 310                 315                 320

Cys His His Leu Asp Lys Ser Ile Lys Glu Asp Val Gln Phe Ala Asp
                325                 330                 335

Ser Arg Ile Arg Pro Gln Thr Ile Ala Ala Glu Asp Gln Leu His Asp
            340                 345                 350

Met Gly Ile Phe Ser Ile Thr Ser Ser Asp Ser Gln Ala Met Gly Arg
        355                 360                 365

Val Gly Glu Val Ile Thr Arg Thr Trp Gln Thr Ala Asp Lys Asn Lys
    370                 375                 380

Lys Glu Phe Gly Arg Leu Lys Glu Glu Lys Gly Asp Asn Asp Asn Phe
385                 390                 395                 400

Arg Ile Lys Arg Tyr Ile Ser Lys Tyr Thr Ile Asn Pro Gly Ile Ala
                405                 410                 415

His Gly Ile Ser Asp Tyr Val Gly Ser Val Glu Val Gly Lys Tyr Ala
            420                 425                 430

Asp Leu Val Leu Trp Ser Pro Ala Phe Phe Gly Ile Lys Pro Asn Met
        435                 440                 445

Ile Ile Lys Gly Gly Phe Ile Ala Leu Ser Gln Met Gly Asp Ala Asn
    450                 455                 460

Ala Ser Ile Pro Thr Pro Gln Pro Val Tyr Tyr Arg Glu Met Phe Gly
465                 470                 475                 480

His His Gly Lys Asn Lys Phe Asp Thr Asn Ile Thr Phe Val Ser Gln
                485                 490                 495

Ala Ala Tyr Lys Ala Gly Ile Lys Glu Glu Leu Gly Leu Asp Arg Ala
            500                 505                 510

Ala Pro Pro Val Lys Asn Cys Arg Asn Ile Thr Lys Lys Asp Leu Lys
        515                 520                 525

Phe Asn Asp Val Thr Ala His Ile Asp Val Asn Pro Glu Thr Tyr Lys
    530                 535                 540

Val Lys Val Asp Gly Lys Glu Val Thr Ser Lys Ala Ala Asp Glu Leu
545                 550                 555                 560

Ser Leu Ala Gln Leu Tyr Asn Leu Phe
                565
```

-continued ( 2 ) INFORMATION FOR SEQ ID NO:22:

( i ) SEQUENCE CHARACTERISTICS:
( A ) LENGTH: 237 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:22:

Met Lys Leu Thr Pro Lys Glu Leu Asp Lys Leu Met His Tyr Ala Gly
1 5 10 15

Glu Leu Ala Lys Lys Arg Lys Glu Lys Gly Ile Lys Leu Asn Tyr Val
20 25 30

Glu Ala Val Ala Leu Ile Ser Ala His Ile Met Glu Glu Ala Arg Ala
35 40 45

Gly Lys Lys Thr Ala Ala Glu Leu Met Gln Glu Gly Arg Thr Leu Leu
50 55 60

Lys Pro Asp Asp Val Met Asp Gly Val Ala Ser Met Ile His Glu Val
65 70 75 80

Gly Ile Glu Ala Met Phe Pro Asp Gly Thr Lys Leu Val Thr Val His
85 90 95

Thr Pro Ile Glu Ala Asn Gly Lys Leu Val Pro Gly Glu Leu Phe Leu
100 105 110

Lys Asn Glu Asp Ile Thr Ile Asn Glu Gly Lys Lys Ala Val Ser Val
115 120 125

Lys Val Lys Asn Val Gly Asp Arg Pro Val Gln Ile Gly Ser His Phe
130 135 140

His Phe Phe Glu Val Asn Arg Cys Leu Asp Phe Asp Arg Glu Lys Thr
145 150 155 160

Phe Gly Lys Arg Leu Asp Ile Ala Ser Gly Thr Ala Val Arg Phe Glu
165 170 175

Pro Gly Glu Glu Lys Ser Val Glu Leu Ile Asp Ile Gly Gly Asn Arg
180 185 190

Arg Ile Phe Gly Phe Asn Ala Leu Val Asp Arg Gln Ala Asp Asn Glu
195 200 205

Ser Lys Lys Ile Ala Leu His Arg Ala Lys Glu Arg Gly Phe His Gly
210 215 220

Ala Lys Ser Asp Asp Asn Tyr Val Lys Thr Ile Lys Glu
225 230 235

( 2 ) INFORMATION FOR SEQ ID NO:23:

( i ) SEQUENCE CHARACTERISTICS:
( A ) LENGTH: 100 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:23:

Met Glu Leu Thr Pro Arg Glu Lys Asp Lys Leu Leu Leu Phe Thr Ala
1 5 10 15

Gly Leu Val Ala Glu Arg Arg Leu Ala Lys Gly Leu Lys Leu Asn Tyr
20 25 30

Pro Glu Arg Val Ala Leu Ile Ser Cys Ala Ile Met Glu Gly Ala Arg
35 40 45

Glu Gly Lys Thr Val Ala Gln Leu Met Ser Glu Gly Arg Thr Val Leu

-continued 50 55 60

Thr Ala Glu Gln Val Met Glu Gly Val Pro Glu Met Ile Lys Asp Val
65 70 75 80

Gln Val Glu Cys Thr Phe Pro Asp Gly Thr Lys Leu Val Ser Ile His
85 90 95

Ser Pro Ile Val
100

( 2 ) INFORMATION FOR SEQ ID NO:24:

( i ) SEQUENCE CHARACTERISTICS:
( A ) LENGTH: 109 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:24:

Met Ile Pro Gly Glu Ile Arg Val Asn Ala Ala Leu Gly Asp Ile Glu
1 5 10 15

Leu Asn Ala Gly Arg Glu Thr Lys Thr Ile Gln Val Ala Asn His Gly
20 25 30

Asp Arg Pro Val Gln Cys Gly Ser His Tyr His Phe Tyr Glu Val Asn
35 40 45

Glu Ala Leu Arg Phe Ala Arg Lys Glu Thr Leu Gly Phe Arg Leu Asn
50 55 60

Ile Pro Ala Gly Met Ala Val Arg Phe Glu Pro Gly Gln Ser Arg Thr
65 70 75 80

Val Asp Glu Leu Val Ala Phe Ala Gly Lys Arg Glu Ile Tyr Gly Phe
85 90 95

His Gly Lys Val Met Gly Lys Leu Glu Ser Glu Lys Lys
100 105

( 2 ) INFORMATION FOR SEQ ID NO:25:

( i ) SEQUENCE CHARACTERISTICS:
( A ) LENGTH: 840 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:25:

Met Lys Leu Ser Pro Arg Glu Val Glu Lys Leu Gly Leu His Asn Ala
1 5 10 15

Gly Tyr Leu Ala Gln Lys Arg Leu Ala Arg Gly Val Arg Leu Asn Tyr
20 25 30

Thr Glu Ala Val Ala Leu Ile Ala Ser Gln Ile Met Glu Tyr Ala Arg
35 40 45

Asp Gly Glu Lys Thr Val Ala Gln Leu Met Cys Leu Gly Gln His Leu
50 55 60

Leu Gly Arg Arg Gln Val Leu Pro Ala Val Pro His Leu Leu Asn Ala
65 70 75 80

Val Gln Val Glu Ala Thr Glu Pro Asp Gly Thr Lys Leu Val Thr Val
85 90 95

His Asp Pro Ile Ser Arg Glu Asn Gly Glu Leu Gln Glu Ala Leu Phe
100 105 110

Gly Ser Leu Leu Pro Val Pro Ser Leu Asp Lys Phe Ala Glu Thr Lys

-continued 115 120 125

Glu Asp Asn Arg Ile Pro Gly Glu Ile Leu Cys Glu Asp Glu Cys Leu
130 135 140

Thr Leu Asn Ile Gly Arg Lys Ala Val Ile Leu Lys Val Thr Ser Lys
145 150 155 160

Gly Asp Arg Pro Ile Gln Val Gly Ser His Tyr His Phe Ile Glu Val
165 170 175

Asn Pro Tyr Leu Thr Phe Asp Arg Arg Lys Ala Tyr Gly Met Arg Leu
180 185 190

Asn Ile Ala Ala Gly Thr Ala Val Arg Phe Glu Pro Gly Asp Cys Lys
195 200 205

Ser Val Thr Leu Val Ser Ile Glu Gly Asn Lys Val Ile Arg Gly Gly
210 215 220

Asn Ala Ile Ala Asp Gly Pro Val Asn Glu Thr Asn Leu Glu Ala Ala
225 230 235 240

Met His Ala Val Arg Ser Arg Gly Phe Gly His Glu Glu Glu Lys Asp
245 250 255

Ala Pro Glu Gly Phe Thr Lys Glu Asp Pro Asn Cys Ser Phe Asn Thr
260 265 270

Phe Ile His Arg Lys Glu Tyr Ala Asn Lys Tyr Gly Pro Thr Thr Gly
275 280 285

Asp Lys Ile Arg Leu Gly Asp Thr Asn Leu Leu Ala Glu Ile Glu Lys
290 295 300

Asp Tyr Ala Leu Tyr Gly Asp Glu Cys Val Phe Gly Gly Gly Lys Val
305 310 315 320

Ile Arg Asp Gly Met Gly Gln Ser Cys Gly His Pro Pro Ala Ile Ser
325 330 335

Leu Asp Thr Val Ile Thr Asn Ala Val Ile Ile Asp Tyr Thr Gly Ile
340 345 350

Ile Lys Ala Asp Ile Gly Ile Lys Asp Gly Leu Ile Ala Ser Ile Gly
355 360 365

Lys Ala Gly Asn Pro Asp Ile Met Asn Gly Val Phe Ser Asn Met Ile
370 375 380

Ile Gly Ala Asn Thr Glu Val Ile Ala Gly Glu Gly Leu Ile Val Thr
385 390 395 400

Ala Gly Gly Ile Asp Cys His Ile His Tyr Ile Cys Pro Gln Leu Val
405 410 415

Tyr Glu Ala Ile Ser Ser Gly Ile Thr Thr Leu Val Gly Gly Gly Thr
420 425 430

Gly Pro Ala Ala Gly Thr Arg Ala Thr Thr Cys Thr Pro Ser Pro Thr
435 440 445

Gln Met Arg Leu Met Leu Gln Ser Thr Asp Asp Leu Pro Leu Asn Phe
450 455 460

Gly Phe Thr Gly Lys Gly Ser Ser Ser Lys Pro Asp Glu Leu His Glu
465 470 475 480

Ile Ile Lys Ala Gly Ala Met Gly Leu Lys Leu His Glu Asp Trp Gly
485 490 495

Ser Thr Pro Ala Ala Ile Asp Asn Cys Leu Thr Ile Ala Glu His His
500 505 510

Asp Ile Gln Ile Asn Ile His Thr Asp Thr Leu Asn Glu Ala Gly Phe
515 520 525

Val Glu His Ser Ile Ala Ala Phe Lys Gly Arg Thr Ile His Thr Tyr
530 535 540

-continued

His Ser Glu Gly Ala Gly Gly Gly His Ala Pro Asp Ile Ile Lys Val
545 550 555 560

Cys Gly Ile Lys Asn Val Leu Pro Ser Ser Thr Asn Pro Thr Arg Pro
565 570 575

Leu Thr Ser Asn Thr Ile Asp Glu His Leu Asp Met Leu Met Val Cys
580 585 590

His His Leu Asp Arg Glu Ile Pro Glu Asp Val Ala Phe Ala His Ser
595 600 605

Arg Ile Arg Lys Lys Thr Ile Ala Ala Glu Asp Val Leu His Asp Ile
610 615 620

Gly Ala Ile Ser Ile Ile Ser Ser Asp Ser Gln Ala Met Gly Arg Val
625 630 635 640

Gly Glu Val Ile Ser Arg Thr Trp Gln Thr Ala Asp Lys Asn Lys Ala
645 650 655

Gln Thr Gly Pro Leu Lys Cys Asp Ser Ser Asp Asn Asp Asn Phe Arg
660 665 670

Ile Lys Arg Tyr Ile Ala Lys Tyr Thr Ile Asn Pro Ala Ile Ala His
675 680 685

Gly Ile Ser Gln Tyr Val Gly Ser Val Glu Val Gly Lys Leu Ala Asp
690 695 700

Leu Val Leu Trp Lys Pro Ser Phe Phe Gly Thr Lys Pro Glu Met Val
705 710 715 720

Ile Lys Gly Gly Met Val Ala Trp Ala Asp Ile Gly Asp Pro Asn Ala
725 730 735

Ser Ile Pro Thr Pro Gln Pro Val Lys Met Arg Pro Met Tyr Gly Thr
740 745 750

Leu Gly Lys Ala Gly Gly Ala Leu Ser Ile Ala Phe Val Ser Lys Ala
755 760 765

Ala Leu Asp Gln Arg Val Asn Val Leu Tyr Gly Leu Asn Lys Arg Val
770 775 780

Glu Ala Val Ser Asn Val Arg Lys Leu Thr Lys Leu Asp Met Lys Leu
785 790 795 800

Asn Asp Ala Leu Pro Glu Ile Thr Val Asp Pro Glu Ser Tyr Thr Val
805 810 815

Lys Ala Asp Gly Lys Leu Leu Cys Val Ser Glu Ala Thr Thr Val Pro
820 825 830

Leu Ser Arg Asn Tyr Phe Leu Phe
835 840

( 2 ) INFORMATION FOR SEQ ID NO:26:

( i ) SEQUENCE CHARACTERISTICS:
( A ) LENGTH: 569 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:26:

Met Lys Lys Ile Ser Arg Lys Glu Tyr Val Ser Met Tyr Gly Pro Thr
1 5 10 15

Thr Gly Asp Lys Val Arg Leu Gly Asp Thr Asp Leu Ile Ala Glu Val
20 25 30

Glu His Asp Tyr Thr Ile Tyr Gly Glu Glu Leu Lys Phe Gly Gly Gly
35 40 45

Lys Thr Leu Arg Glu Gly Met Ser Gln Ser Asn Asn Pro Ser Lys Glu

-continued 50 55 60

Glu Leu Asp Leu Ile Ile Thr Asn Ala Leu Ile Val Asp Tyr Thr Gly
65 70 75 80

Ile Tyr Lys Ala Asp Ile Gly Ile Lys Asp Gly Lys Ile Ala Gly Ile
85 90 95

Gly Lys Gly Gly Asn Lys Asp Met Gln Asp Gly Val Lys Asn Asn Leu
100 105 110

Ser Val Gly Pro Ala Thr Glu Ala Leu Ala Gly Glu Gly Leu Ile Val
115 120 125

Thr Ala Gly Gly Ile Asp Thr His Ile His Phe Ile Ser Pro Gln Gln
130 135 140

Ile Pro Thr Ala Phe Ala Ser Gly Val Thr Thr Met Ile Gly Gly Gly
145 150 155 160

Thr Gly Pro Ala Asp Gly Thr Asn Ala Thr Thr Ile Thr Pro Gly Arg
165 170 175

Arg Asn Leu Lys Trp Met Leu Arg Ala Ala Glu Glu Tyr Ser Met Asn
180 185 190

Leu Gly Phe Leu Ala Lys Gly Asn Ala Ser Asn Asp Ala Ser Ala Arg
195 200 205

Asp Gln Ile Glu Ala Gly Ala Ile Gly Phe Lys Ile His Glu Asp Trp
210 215 220

Gly Thr Thr Pro Ser Ala Ile Asn His Ala Leu Asp Val Ala Asp Lys
225 230 235 240

Tyr Asp Val Gln Val Ala Ile His Thr Asp Thr Leu Asn Glu Ala Gly
245 250 255

Cys Val Glu Asp Thr Met Ala Ala Ile Ala Gly Arg Thr Met His Thr
260 265 270

Phe His Thr Glu Gly Ala Gly Gly Gly His Ala Pro Asp Ile Ile Lys
275 280 285

Val Ala Gly Glu His Asn Ile Leu Pro Ala Ser Thr Asn Pro Thr Ile
290 295 300

Pro Phe Thr Val Asn Thr Glu Ala Glu His Met Asp Met Leu Met Val
305 310 315 320

Cys His His Leu Asp Lys Ser Ile Lys Glu Asp Val Gln Phe Ala Asp
325 330 335

Ser Arg Ile Arg Pro Gln Thr Ile Ala Ala Glu Asp Thr Leu His Asp
340 345 350

Met Gly Ile Phe Ser Ile Thr Ser Ser Asp Ser Gln Ala Met Gly Arg
355 360 365

Val Gly Glu Val Ile Thr Arg Thr Trp Gln Thr Ala Asp Lys Asn Lys
370 375 380

Lys Glu Phe Gly Arg Leu Lys Glu Glu Lys Gly Asp Asn Asp Asn Phe
385 390 395 400

Arg Ile Lys Arg Tyr Leu Ser Lys Tyr Thr Ile Asn Pro Ala Ile Ala
405 410 415

His Gly Ile Ser Glu Tyr Val Gly Ser Val Glu Val Gly Lys Val Ala
420 425 430

Asp Leu Val Leu Trp Ser Pro Ala Phe Phe Gly Val Lys Pro Asn Met
435 440 445

Ile Ile Lys Gly Gly Phe Ile Ala Leu Ser Gln Met Gly Asp Ala Asn
450 455 460

Ala Ser Ile Pro Thr Pro Gln Pro Val Tyr Tyr Arg Glu Met Phe Gly
465 470 475 480

-continued

His His Gly Lys Ala Lys Tyr Asp Arg Asn Ile Thr Phe Val Ser Gln
485 490 495

Ala Ala Tyr Asp Lys Gly Ile Lys Glu Glu Leu Gly Leu Glu Arg Gln
500 505 510

Val Leu Pro Val Lys Asn Cys Arg Asn Ile Thr Lys Lys Asp Met Gln
515 520 525

Phe Asn Asp Thr Thr Ala His Ile Glu Val Asn Pro Glu Thr Tyr His
530 535 540

Val Phe Val Asp Gly Lys Glu Val Thr Ser Lys Pro Ala Asn Lys Val
545 550 555 560

Ser Leu Ala Gln Leu Phe Ser Ile Phe
565

( 2 ) INFORMATION FOR SEQ ID NO:27:

( i ) SEQUENCE CHARACTERISTICS:
( A ) LENGTH: 569 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:27:

Met Lys Thr Ile Ser Arg Gln Ala Tyr Ala Asp Met Phe Gly Pro Thr
1 5 10 15

Thr Gly Asp Arg Leu Arg Leu Ala Asp Thr Glu Leu Phe Leu Glu Ile
20 25 30

Glu Lys Asp Phe Thr Thr Tyr Gly Glu Glu Val Lys Phe Gly Gly Gly
35 40 45

Lys Val Ile Arg Asp Gly Met Gly Gln Ser Gln Val Val Ser Ala Glu
50 55 60

Cys Val Asp Val Leu Ile Thr Asn Ala Ile Ile Leu Asp Tyr Trp Gly
65 70 75 80

Ile Val Lys Ala Asp Ile Gly Ile Lys Asp Gly Arg Ile Val Gly Ile
85 90 95

Gly Lys Ala Gly Asn Pro Asp Val Gln Pro Asn Val Asp Ile Val Ile
100 105 110

Gly Pro Gly Thr Glu Val Val Ala Gly Glu Gly Lys Ile Val Thr Ala
115 120 125

Gly Gly Ile Asp Thr His Ile His Phe Ile Cys Pro Gln Gln Ala Gln
130 135 140

Glu Gly Leu Val Ser Gly Val Thr Thr Phe Ile Gly Gly Gly Thr Gly
145 150 155 160

Pro Val Ala Gly Thr Asn Ala Thr Thr Val Thr Pro Gly Ile Trp Asn
165 170 175

Met Tyr Arg Met Leu Glu Ala Val Asp Glu Leu Pro Ile Asn Val Gly
180 185 190

Leu Phe Gly Lys Gly Cys Val Ser Gln Pro Glu Ala Ile Arg Glu Gln
195 200 205

Ile Thr Ala Gly Ala Ile Gly Leu Lys Ile His Glu Asp Trp Gly Ala
210 215 220

Thr Pro Met Ala Ile His Asn Cys Leu Asn Val Ala Asp Glu Met Asp
225 230 235 240

Val Gln Val Ala Ile His Ser Asp Thr Leu Asn Glu Gly Gly Phe Tyr
245 250 255

Glu Glu Thr Val Lys Ala Ile Ala Gly Arg Val Ile His Thr Phe His

-continued 260 265 270

Thr Glu Gly Ala Gly Gly Gly His Ala Pro Asp Val Ile Lys Ser Val
275 280 285

Gly Glu Pro Asn Ile Leu Pro Ala Ser Thr Asn Pro Thr Met Pro Tyr
290 295 300

Thr Ile Asn Thr Val Asp Glu His Leu Asp Met Leu Met Val Cys His
305 310 315 320

His Leu Asp Pro Ser Ile Pro Glu Asp Val Ala Phe Ala Glu Ser Arg
325 330 335

Ile Arg Arg Glu Thr Ile Ala Ala Glu Asp Ile Leu His Asp Met Gly
340 345 350

Ala Ile Ser Val Met Ser Ser Asp Ser Gln Ala Met Gly Arg Val Gly
355 360 365

Glu Val Ile Leu Arg Thr Trp Gln Cys Ala His Lys Asn Lys Leu Gln
370 375 380

Arg Gly Thr Leu Ala Gly Asp Ser Ala Asp Asn Asp Asn Asn Arg Ile
385 390 395 400

Lys Arg Tyr Ile Ala Lys Tyr Thr Ile Asn Pro Ala Leu Ala His Gly
405 410 415

Ile Ala His Thr Val Gly Ser Ile Glu Lys Gly Lys Leu Ala Asp Ile
420 425 430

Val Leu Trp Asp Pro Ala Phe Phe Gly Val Lys Pro Ala Leu Ile Ile
435 440 445

Lys Gly Gly Met Val Arg Tyr Ala Pro Met Gly Asp Ile Asn Ala Ala
450 455 460

Ile Pro Thr Pro Gln Pro Val His Tyr Arg Pro Met Tyr Ala Cys Leu
465 470 475 480

Gly Lys Ala Lys Tyr Gln Thr Ser Met Ile Phe Met Ser Lys Ala Gly
485 490 495

Ile Glu Ala Gly Val Pro Glu Lys Leu Gly Leu Lys Ser Leu Ser Leu
500 505 510

Ile Gly Arg Val Glu Gly Cys Arg His Ile Thr Lys Ala Ser Met Ile
515 520 525

His Asn Asn Tyr Val Pro His Ile Glu Leu Asp Pro Gln Thr Tyr Ile
530 535 540

Val Lys Ala Asp Gly Val Pro Leu Val Cys Glu Pro Ala Thr Glu Leu
545 550 555 560

Pro Met Ala Gln Arg Tyr Phe Leu Phe
565

( 2 ) INFORMATION FOR SEQ ID NO:28:

( i ) SEQUENCE CHARACTERISTICS:
( A ) LENGTH: 2284 base pairs
( B ) TYPE: nucleic acid
( C ) STRANDEDNESS: double
( D ) TOPOLOGY: linear ( i i ) MOLECULE TYPE: DNA (genomic)

( x i ) SEQUENCE DESCRIPTION: SEQ ID NO:28:

ACAAACATGA TCTCATATCA GGGACTTGTT CGCACCTTCC CTAAAAATGC GCTATAGTTG 60

TGTCGCTTAA GAATACTAAG CGCTAAATTT CTATTTTATT TATCAAAACT TAGGAGAACT 120

GAAATGAAGT TTCAACCATT AGGAGAAAGG GTCTTAGTAG AAAGACTTGA AGAAGAGAAC 180

AAAACCAGTT CAGGCATCAT CATCCCTGAT AACGCTAAAG AAAAGCCTTT AATGGGCGTA 240

-continued

```
GTCAAAGCGG TTAGCCATAA AATCAGTGAG GGTTGCAAAT GCGTTAAAGA AGGCGATGTG   300
ATCGCTTTTG GCAAATACAA AGGCGCAGAA ATCGTTTTAG ATGGCGTTGA ATACATGGTG   360
CTAGAACTAG AAGACATTCT AGGTATTGTG GGCTCAGGCT CTTGCTGTCA TACAGGTAAT   420
CATGATCATA AACATGCTAA AGAGCATGAA GCTTGCTGTC ATGATCACAA AAAACACTAA   480
AAAACATTAT TATTAAGGAT ACAAAATGGC AAAAGAAATC AAATTTTCAG ATAGCGCAAG   540
AAACCTTTTA TTTGAAGGCG TAAGACAACT CCATGACGCT GTCAAAGTAA CCATGGGGCC   600
AAGAGGCAGG AACGTGTTGA TCCAAAAAAG CTATGGCGCT CCAAGCATCA CCAAAGACGG   660
CGTGAGCGTG GCTAAAGAGA TTGAATTAAG TTGCCCCGTG GCTAACATGG GCGCTCAGCT   720
CGTTAAAGAA GATGCGAGCA AAACCGCTGA TGCCGCCGGC GATGGCACGA CCACAGCGAC   780
CGTGCTGGCT TATAGCATTT TTAAAGAGGG CTTGAGGAAT ATCACGGCTG GGGCTAACCC   840
TATTGAAGTG AAACGAGGCA TGGATAAAGC GCCTGAAGCG ATCATTAATG AGCTTAAAAA   900
AGCGAGCAAA AAAGTGGGCG GTAAAGAAGA AATCACCCAA GTAGCGACCA TTTCTGCAAA   960
CTCCGATCAC AATATCGGGA AACTCATCGC TGACGCTATG GAAAAAGTGG GTAAAGACGG  1020
CGTGATCACC GTTGAAGAAG CTAAGGGCAT TGAAGATGAA TTAGATGTCG TAGAAGGCAT  1080
GCAATTTGAT AGAGGCTACC TCTCCCCTTA CTTTGTAACC AACGCTGAGA AAATGACCGC  1140
TCAATTGGAT AACGCTTACA TCCTTTTAAC GGATAAAAAA ATCTCTAGCA TGAAAGACAT  1200
TCTCCCGCTA CTAGAAAAAA CCATGAAAGA GGGCAAACCG CTTTTAATCA TCGCTGAAGA  1260
CATTGAGGGC GAAGCTTTAA CGACTCTAGT GGTGAATAAA TTAAGAGGCG TGTTGAATAT  1320
CGCAGCGGTT AAAGCTCCAG GCTTTGGGGA CAGGAGAAAA GAAATGCTCA AAGACATCGC  1380
TGTTTTAACC GGCGGTCAAG TCATTAGCGA AGAATTGGGC TTGAGTCTAG AAAACGCTGA  1440
AGTGGAGTTT TTAGGCAAAG CGAAGATTGT GATTGACAAA GACAACACCA CGATCGTAGA  1500
TGGCAAAGGC CATAGCCATG ACGTCAAAGA CAGAGTCGCG CAAATCAAAA CCCAAATTGC  1560
AAGCACGACA AGCGATTACG ACAAAGAAAA ATTGCAAGAA AGATTGGCCA AACTCTCTGG  1620
CGGTGTGGCT GTGATTAAAG TGGGCGCTGC GAGTGAAGTG GAAATGAAAG AGAAAAAAGA  1680
CCGGGTGGAT GACGCGTTGA GCGCGACTAA AGCGGCGGTT GAAGAAGGCA TTGTGATTGG  1740
GGGCGGTGCG GCCCTCATTC GCGCGGCCCA AAAAGTGCAT TTGAATTTAC ACGATGATGA  1800
AAAAGTGGGC TATGAAATCA TCATGCGCGC CATTAAAGCC CCATTAGCTC AAATCGCTAT  1860
CAATGCCGGT TATGATGGCG GTGTGGTCGT GAATGAAGTA GAAAAACACG AAGGGCATTT  1920
TGGTTTTAAC GCTAGCAATG GCAAGTATGT GGACATGTTT AAAGAAGGCA TTATTGACCC  1980
CTTAAAAGTA GAAAGGATCG CTTTACAAAA TGCGGTTTCG GTTTCAAGCC TGCTTTTAAC  2040
CACAGAAGCC ACCGTGCATG AAATCAAAGA AGAAAAAGCG GCCCCAGCAA TGCCTGATAT  2100
GGGTGGCATG GGCGGAATGG GAGGCATGGG CGGCATGATG TAAGCCCCCT TGCTTTTTGG  2160
TATCATCTGC TTTTAAAATC CATCTTCTAG AATCCCCCCT TCTAAAATCC CTTTTTTGGG  2220
GGGTGCTTTT GGTTTGATAA AACCGCTCGC TTTTAAAAAC GCGCAACAAA AAACTCTGTT  2280
AAGC                                                               2284
```

( 2 ) INFORMATION FOR SEQ ID NO:29:

( i ) SEQUENCE CHARACTERISTICS:
( A ) LENGTH: 118 amino acids
( B ) TYPE: amino acid
( C ) STRANDEDNESS: single
( D ) TOPOLOGY: linear ( i i ) MOLECULE TYPE: protein -continued ( i x ) FEATURE:
( A ) NAME/KEY: Protein
( B ) LOCATION: 1..118
( D ) OTHER INFORMATION: /product="H. pylori - Hsp A."

( x i ) SEQUENCE DESCRIPTION: SEQ ID NO:29:

Met Lys Phe Gln Pro Leu Gly Glu Arg Val Leu Val Glu Arg Leu Glu
1 5 10 15

Glu Glu Asn Lys Thr Ser Ser Gly Ile Ile Ile Pro Asp Asn Ala Lys
20 25 30

Glu Lys Pro Leu Met Gly Val Val Lys Ala Val Ser His Lys Ile Ser
35 40 45

Glu Gly Cys Lys Cys Val Lys Glu Gly Asp Val Ile Ala Phe Gly Lys
50 55 60

Tyr Lys Gly Ala Glu Ile Val Leu Asp Gly Val Glu Tyr Met Val Leu
65 70 75 80

Glu Leu Glu Asp Ile Leu Gly Ile Val Gly Ser Gly Ser Cys Cys His
85 90 95

Thr Gly Asn His Asp His Lys His Ala Lys Glu His Glu Ala Cys Cys
100 105 110

His Asp His Lys Lys His
115

( 2 ) INFORMATION FOR SEQ ID NO:30:

( i ) SEQUENCE CHARACTERISTICS:
( A ) LENGTH: 545 amino acids
( B ) TYPE: amino acid
( C ) STRANDEDNESS: single
( D ) TOPOLOGY: linear ( i i ) MOLECULE TYPE: protein ( i x ) FEATURE:
( A ) NAME/KEY: Protein
( B ) LOCATION: 1..545
( D ) OTHER INFORMATION: /product="H. pylori - Hsp B."

( x i ) SEQUENCE DESCRIPTION: SEQ ID NO:30:

Met Ala Lys Glu Ile Lys Phe Ser Asp Ser Ala Arg Asn Leu Leu Phe
1 5 10 15

Glu Gly Val Arg Gln Leu His Asp Ala Val Lys Val Thr Met Gly Pro
20 25 30

Arg Gly Arg Asn Val Leu Ile Gln Lys Ser Tyr Gly Ala Pro Ser Ile
35 40 45

Thr Lys Asp Gly Val Ser Val Ala Lys Glu Ile Glu Leu Ser Cys Pro
50 55 60

Val Ala Asn Met Gly Ala Gln Leu Val Lys Glu Asp Ala Ser Lys Thr
65 70 75 80

Ala Asp Ala Ala Gly Asp Gly Thr Thr Thr Ala Thr Val Leu Ala Tyr
85 90 95

Ser Ile Phe Lys Glu Gly Leu Arg Asn Ile Thr Ala Gly Ala Asn Pro
100 105 110

Ile Glu Val Lys Arg Gly Met Asp Lys Ala Pro Glu Ala Ile Ile Asn
115 120 125

Glu Leu Lys Lys Ala Ser Lys Lys Val Gly Gly Lys Glu Glu Ile Thr
130 135 140

Gln Val Ala Thr Ile Ser Ala Asn Ser Asp His Asn Ile Gly Lys Leu
145 150 155 160

-continued

Ile Ala Asp Ala Met Glu Lys Val Gly Lys Asp Gly Val Ile Thr Val
165 170 175

Glu Glu Ala Lys Gly Ile Glu Asp Glu Leu Asp Val Val Glu Gly Met
180 185 190

Gln Phe Asp Arg Gly Tyr Leu Ser Pro Tyr Phe Val Thr Asn Ala Glu
195 200 205

Lys Met Thr Ala Gln Leu Asp Asn Ala Tyr Ile Leu Leu Thr Asp Lys
210 215 220

Lys Ile Ser Ser Met Lys Asp Ile Leu Pro Leu Leu Glu Lys Thr Met
225 230 235 240

Lys Glu Gly Lys Pro Leu Leu Ile Ile Ala Glu Asp Ile Glu Gly Glu
245 250 255

Ala Leu Thr Thr Leu Val Val Asn Lys Leu Arg Gly Val Leu Asn Ile
260 265 270

Ala Ala Val Lys Ala Pro Gly Phe Gly Asp Arg Arg Lys Glu Met Leu
275 280 285

Lys Asp Ile Ala Val Leu Thr Gly Gly Gln Val Ile Ser Glu Glu Leu
290 295 300

Gly Leu Ser Leu Glu Asn Ala Glu Val Glu Phe Leu Gly Lys Ala Lys
305 310 315 320

Ile Val Ile Asp Lys Asp Asn Thr Thr Ile Val Asp Gly Lys Gly His
325 330 335

Ser His Asp Val Lys Asp Arg Val Ala Gln Ile Lys Thr Gln Ile Ala
340 345 350

Ser Thr Thr Ser Asp Tyr Asp Lys Glu Lys Leu Gln Glu Arg Leu Ala
355 360 365

Lys Leu Ser Gly Gly Val Ala Val Ile Lys Val Gly Ala Ala Ser Glu
370 375 380

Val Glu Met Lys Glu Lys Lys Asp Arg Val Asp Asp Ala Leu Ser Ala
385 390 395 400

Thr Lys Ala Ala Val Glu Glu Gly Ile Val Ile Gly Gly Gly Ala Ala
405 410 415

Leu Ile Arg Ala Ala Gln Lys Val His Leu Asn Leu His Asp Asp Glu
420 425 430

Lys Val Gly Tyr Glu Ile Ile Met Arg Ala Ile Lys Ala Pro Leu Ala
435 440 445

Gln Ile Ala Ile Asn Ala Gly Tyr Asp Gly Gly Val Val Val Asn Glu
450 455 460

Val Glu Lys His Glu Gly His Phe Gly Phe Asn Ala Ser Asn Gly Lys
465 470 475 480

Tyr Val Asp Met Phe Lys Glu Gly Ile Ile Asp Pro Leu Lys Val Glu
485 490 495

Arg Ile Ala Leu Gln Asn Ala Val Ser Val Ser Ser Leu Leu Leu Thr
500 505 510

Thr Glu Ala Thr Val His Glu Ile Lys Glu Glu Lys Ala Ala Pro Ala
515 520 525

Met Pro Asp Met Gly Gly Met Gly Gly Met Gly Gly Met Gly Gly Met
530 535 540

Met

545

( 2 ) INFORMATION FOR SEQ ID NO:31:

( i ) SEQUENCE CHARACTERISTICS:

-continued ( A ) LENGTH: 548 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:31:

Met Ala Lys Glu Leu Arg Phe Gly Asp Asp Ala Arg Leu Gln Met Leu
1 5 10 15

Ala Gly Val Asn Ala Leu Ala Asp Ala Val Gln Val Thr Met Gly Pro
20 25 30

Arg Gly Arg Asn Val Val Leu Glu Lys Ser Tyr Gly Ala Pro Thr Val
35 40 45

Thr Lys Asp Gly Val Ser Val Ala Lys Glu Ile Glu Phe Glu His Arg
50 55 60

Phe Met Asn Met Gly Ala Gln Met Val Lys Glu Val Ala Ser Lys Thr
65 70 75 80

Ser Asp Thr Ala Gly Asp Gly Thr Thr Thr Ala Thr Val Leu Ala Arg
85 90 95

Ser Ile Leu Val Glu Gly His Lys Ala Val Ala Ala Gly Met Asn Pro
100 105 110

Met Asp Leu Lys Arg Gly Ile Asp Lys Ala Val Leu Ala Val Thr Lys
115 120 125

Lys Leu Gln Ala Met Ser Lys Pro Cys Lys Asp Ser Lys Ala Ile Ala
130 135 140

Gln Val Gly Thr Ile Ser Ala Asn Ser Asp Glu Ala Ile Gly Ala Ile
145 150 155 160

Ile Ala Glu Ala Met Glu Lys Val Gly Lys Glu Gly Val Ile Thr Val
165 170 175

Glu Asp Gly Asn Gly Leu Glu Asn Glu Leu Tyr Val Val Glu Gly Met
180 185 190

Gln Phe Asp Arg Gly Tyr Ile Ser Pro Tyr Phe Ile Asn Asn Gln Gln
195 200 205

Asn Met Ser Cys Glu Leu Glu His Pro Phe Ile Leu Leu Val Asp Lys
210 215 220

Lys Val Ser Ser Ile Arg Glu Met Leu Ser Val Leu Glu Gly Val Ala
225 230 235 240

Lys Ser Gly Arg Pro Leu Leu Ile Ile Ala Glu Asp Ile Glu Gly Glu
245 250 255

Ala Leu Ala Thr Leu Val Val Asn Asn Met Arg Gly Ile Val Lys Val
260 265 270

Cys Ala Val Lys Ala Pro Gly Phe Gly Asp Arg Arg Lys Ala Met Leu
275 280 285

Gln Asp Ile Ala Ile Leu Thr Lys Gly Gln Val Ile Ser Glu Glu Ile
290 295 300

Gly Lys Ser Leu Glu Gly Ala Thr Leu Glu Asp Leu Gly Ser Ala Lys
305 310 315 320

Arg Ile Val Val Thr Lys Glu Asn Thr Thr Ile Ile Asp Gly Glu Gly
325 330 335

Lys Ala Thr Glu Ile Asn Ala Arg Ile Ala Gln Ile Arg Ala Gln Met
340 345 350

Glu Glu Thr Thr Ser Asp Tyr Asp Arg Glu Lys Leu Gln Glu Arg Val
355 360 365

Ala Lys Leu Ala Gly Gly Val Ala Val Ile Lys Val Gly Ala Ala Thr
370 375 380

Glu Val Glu Met Lys Glu Lys Lys Ala Arg Val Glu Asp Ala Leu His
385 390 395 400

Ala Thr Arg Ala Ala Val Glu Glu Gly Ile Val Ala Gly Gly Gly Val
405 410 415

Ala Leu Ile Arg Ala Gln Lys Ala Leu Asp Ser Leu Lys Gly Asp Asn
420 425 430

Asp Asp Gln Asn Met Gly Ile Asn Ile Leu Arg Arg Ala Ile Glu Ser
435 440 445

Pro Met Arg Gln Ile Val Thr Asn Ala Gly Tyr Glu Ala Ser Val Val
450 455 460

Val Asn Lys Val Ala Glu His Lys Asp Asn Tyr Gly Phe Asn Ala Ala
465 470 475 480

Thr Gly Glu Tyr Gly Asp Met Val Glu Met Gly Ile Leu Asp Pro Thr
485 490 495

Lys Val Thr Arg Met Ala Leu Gln Asn Ala Ala Ser Val Ala Ser Leu
500 505 510

Met Leu Thr Thr Glu Cys Met Val Ala Asp Leu Pro Lys Lys Glu Glu
515 520 525

Gly Val Gly Ala Gly Asp Met Gly Gly Met Gly Gly Met Gly Gly Met
530 535 540

Gly Gly Met Met
545

( 2 ) INFORMATION FOR SEQ ID NO:32:

( i ) SEQUENCE CHARACTERISTICS:
( A ) LENGTH: 548 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:32:

Met Ala Ala Lys Asp Val Lys Phe Gly Asn Asp Ala Arg Val Lys Met
1 5 10 15

Leu Arg Gly Val Asn Val Leu Ala Asp Ala Val Lys Val Thr Leu Gly
20 25 30

Pro Lys Gly Arg Asn Val Val Leu Asp Lys Ser Phe Gly Ala Pro Thr
35 40 45

Ile Thr Lys Asp Gly Val Ser Val Ala Arg Glu Ile Glu Leu Glu Asp
50 55 60

Lys Phe Glu Asn Met Gly Ala Gln Met Val Lys Glu Val Ala Ser Lys
65 70 75 80

Ala Asn Asp Ala Ala Gly Asp Gly Thr Thr Thr Ala Thr Val Leu Ala
85 90 95

Gln Ala Ile Ile Thr Glu Gly Leu Lys Ala Val Ala Ala Gly Met Asn
100 105 110

Pro Met Asp Leu Lys Arg Gly Ile Asp Lys Ala Val Thr Ala Ala Val
115 120 125

Glu Glu Leu Lys Ala Leu Ser Val Pro Cys Ser Asp Ser Lys Ala Ile
130 135 140

Ala Gln Val Gly Thr Ile Ser Ala Asn Ser Asp Glu Thr Val Gly Lys
145 150 155 160

Leu Ile Ala Glu Ala Met Asp Lys Val Gly Lys Glu Gly Val Ile Thr
165 170 175

-continued

Val Glu Asp Gly Thr Gly Leu Gln Asp Glu Leu Asp Val Val Glu Gly
180 185 190

Met Gln Phe Asp Arg Gly Tyr Leu Ser Pro Tyr Phe Ile Asn Lys Pro
195 200 205

Glu Thr Gly Ala Val Glu Leu Glu Ser Pro Phe Ile Leu Leu Ala Asp
210 215 220

Lys Lys Ile Ser Asn Ile Arg Glu Met Leu Pro Val Leu Glu Ala Val
225 230 235 240

Ala Lys Ala Gly Lys Pro Leu Leu Ile Ile Ala Glu Asp Val Glu Gly
245 250 255

Glu Ala Leu Ala Thr Ala Val Val Asn Thr Ile Arg Gly Ile Val Lys
260 265 270

Val Ala Ala Val Lys Ala Pro Gly Phe Gly Asp Arg Arg Lys Ala Met
275 280 285

Leu Gln Asp Ile Ala Thr Leu Thr Gly Gly Thr Val Ile Ser Glu Glu
290 295 300

Ile Gly Met Glu Leu Glu Lys Ala Thr Leu Glu Asp Leu Gly Gln Ala
305 310 315 320

Lys Arg Val Val Ile Asn Lys Asp Thr Thr Thr Ile Ile Asp Gly Val
325 330 335

Gly Glu Glu Ala Ala Ile Gln Gly Arg Val Ala Gln Ile Arg Gln Gln
340 345 350

Ile Glu Glu Ala Thr Ser Asp Tyr Asp Arg Glu Lys Leu Gln Glu Arg
355 360 365

Val Ala Lys Leu Ala Gly Gly Val Ala Val Ile Lys Val Gly Ala Ala
370 375 380

Thr Glu Val Glu Met Lys Glu Lys Lys Ala Arg Val Glu Asp Ala Leu
385 390 395 400

His Ala Thr Arg Ala Ala Val Glu Glu Gly Val Val Ala Gly Gly Gly
405 410 415

Val Ala Leu Ile Arg Val Ala Ser Lys Leu Ala Asp Leu Arg Gly Gln
420 425 430

Asn Glu Asp Gln Asn Val Gly Ile Lys Val Ala Leu Arg Ala Met Glu
435 440 445

Ala Pro Leu Arg Gln Ile Val Leu Asn Cys Gly Glu Glu Pro Ser Val
450 455 460

Val Ala Asn Thr Val Lys Gly Gly Asp Gly Asn Tyr Gly Tyr Asn Ala
465 470 475 480

Ala Thr Glu Glu Tyr Gly Asn Met Ile Asp Met Gly Ile Leu Asp Pro
485 490 495

Thr Lys Val Thr Arg Ser Ala Leu Gln Tyr Ala Ala Ser Val Ala Gly
500 505 510

Leu Met Ile Thr Thr Glu Cys Met Val Thr Asp Leu Pro Lys Asn Asp
515 520 525

Ala Ala Asp Leu Gly Ala Ala Gly Gly Met Gly Gly Met Gly Gly Met
530 535 540

Gly Gly Met Met
545

( 2 ) INFORMATION FOR SEQ ID NO:33:

( i ) SEQUENCE CHARACTERISTICS:

( A ) LENGTH: 544 amino acids ( B ) TYPE: amino acid ( C ) STRANDEDNESS: single ( D ) TOPOLOGY: linear ( i i ) MOLECULE TYPE: protein ( x i ) SEQUENCE DESCRIPTION: SEQ ID NO:33:

Met Ala Ala Lys Asn Ile Lys Tyr Asn Glu Asp Ala Arg Lys Lys Ile
1 5 10 15

His Lys Gly Val Lys Thr Leu Ala Glu Ala Val Lys Val Thr Leu Gly
20 25 30

Pro Lys Gly Arg His Val Val Ile Asp Lys Ser Phe Gly Ser Pro Gln
35 40 45

Val Thr Lys Asp Gly Val Thr Val Ala Lys Glu Ile Glu Leu Glu Asp
50 55 60

Lys His Glu Asn Met Gly Ala Gln Met Val Lys Glu Val Ala Ser Lys
65 70 75 80

Thr Ala Asp Lys Ala Gly Asp Gly Thr Thr Thr Ala Thr Val Leu Ala
85 90 95

Glu Ala Ile Tyr Ser Glu Gly Leu Arg Asn Val Thr Ala Gly Ala Asn
100 105 110

Pro Met Leu Asp Lys Arg Gly Ile Asp Lys Ala Val Lys Val Val Val
115 120 125

Asp Glu Ile Lys Lys Ile Ser Lys Pro Val Gln His His Lys Glu Ile
130 135 140

Ala Gln Val Ala Thr Ile Ser Ala Asn Asn Asp Ala Glu Ile Gly Asn
145 150 155 160

Leu Ile Ala Glu Ala Met Glu Lys Val Gly Lys Asn Gly Ser Ile Thr
165 170 175

Val Glu Glu Ala Lys Gly Phe Glu Thr Val Leu Asp Val Val Glu Gly
180 185 190

Met Asn Phe Asn Arg Gly Tyr Leu Ser Ser Tyr Phe Ser Thr Asn Pro
195 200 205

Glu Thr Gln Glu Cys Val Leu Glu Glu Ala Leu Val Leu Ile Tyr Asp
210 215 220

Lys Lys Ile Ser Gly Ile Lys Asp Phe Leu Pro Val Leu Gln Gln Val
225 230 235 240

Ala Glu Ser Gly Arg Pro Leu Leu Ile Ile Ala Glu Asp Ile Glu Gly
245 250 255

Glu Ala Leu Ala Thr Leu Val Val Asn Arg Leu Arg Ala Gly Phe Arg
260 265 270

Val Cys Ala Val Lys Ala Pro Gly Phe Gly Asp Arg Arg Lys Ala Met
275 280 285

Leu Glu Asp Ile Ala Ile Leu Thr Gly Gly Gln Leu Ile Ser Glu Glu
290 295 300

Leu Gly Met Lys Leu Glu Asn Thr Thr Leu Ala Met Leu Gly Lys Ala
305 310 315 320

Lys Lys Val Ile Val Ser Lys Glu Asp Thr Thr Ile Val Glu Gly Leu
325 330 335

Gly Ser Lys Glu Asp Ile Glu Ser Arg Cys Glu Ser Ile Lys Lys Gln
340 345 350

Ile Glu Asp Ser Thr Ser Asp Tyr Asp Lys Glu Lys Leu Gln Glu Arg
355 360 365

Leu Ala Lys Leu Ser Gly Gly Val Ala Val Ile Arg Val Gly Ala Ala
370 375 380

Thr Glu Ile Glu Met Lys Glu Lys Lys Asp Arg Val Asp Asp Ala Gln
385 390 395 400

-continued

```
His Ala Thr Leu Ala Ala Val Glu Glu Gly Ile Leu Pro Gly Gly Gly
                405                 410                 415

Thr Ala Leu Val Arg Cys Ile Pro Thr Leu Glu Ala Phe Ile Pro Ile
            420                 425                 430

Leu Thr Asn Glu Asp Glu Gln Ile Gly Ala Arg Ile Val Leu Lys Ala
        435                 440                 445

Leu Ser Ala Pro Leu Lys Gln Ile Ala Ala Asn Ala Gly Lys Glu Gly
    450                 455                 460

Ala Ile Ile Cys Gln Gln Val Leu Ser Arg Ser Ser Ser Glu Gly Tyr
465                 470                 475                 480

Asp Ala Leu Arg Asp Ala Tyr Thr Asp Met Ile Glu Ala Gly Ile Leu
                485                 490                 495

Asp Pro Thr Lys Val Thr Arg Cys Ala Leu Glu Ser Ala Ala Ser Val
            500                 505                 510

Ala Gly Leu Leu Leu Thr Thr Glu Ala Leu Ile Ala Asp Ile Pro Glu
        515                 520                 525

Glu Lys Ser Ser Ser Ala Pro Ala Met Pro Gly Ala Gly Met Asp Tyr
    530                 535                 540
```

( 2 ) INFORMATION FOR SEQ ID NO:34:

( i ) SEQUENCE CHARACTERISTICS:
( A ) LENGTH: 541 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:34:

```
Met Ala Lys Thr Ile Ala Tyr Asp Glu Glu Ala Arg Arg Gly Leu Glu
1               5                   10                  15

Arg Gly Leu Asn Ser Leu Ala Asp Ala Val Lys Val Thr Leu Gly Pro
            20                  25                  30

Lys Gly Arg Asn Val Val Leu Glu Lys Lys Trp Gly Ala Pro Thr Ile
        35                  40                  45

Thr Asn Asp Gly Val Ser Ile Ala Lys Glu Ile Glu Leu Glu Asp Pro
    50                  55                  60

Tyr Glu Lys Ile Gly Ala Glu Leu Val Lys Glu Val Ala Lys Lys Thr
65                  70                  75                  80

Asp Asp Val Ala Gly Asp Gly Thr Thr Thr Ala Thr Val Leu Ala Gln
                85                  90                  95

Ala Leu Val Lys Glu Gly Leu Arg Asn Val Ala Ala Gly Ala Asn Pro
            100                 105                 110

Leu Gly Leu Lys Arg Gly Ile Glu Lys Ala Val Asp Lys Val Thr Glu
        115                 120                 125

Thr Leu Leu Lys Asp Ala Lys Glu Val Glu Thr Lys Glu Gln Ile Ala
    130                 135                 140

Ala Thr Ala Ala Ile Ser Ala Gly Asp Gln Ser Ile Gly Asp Leu Ile
145                 150                 155                 160

Ala Glu Ala Met Asp Lys Val Gly Asn Glu Gly Val Ile Thr Val Glu
                165                 170                 175

Glu Ser Asn Thr Phe Gly Leu Gln Leu Glu Leu Thr Glu Gly Met Arg
            180                 185                 190

Phe Asp Lys Gly Tyr Ile Ser Gly Tyr Phe Val Thr Asp Ala Glu Arg
        195                 200                 205

Gln Glu Ala Val Leu Glu Glu Pro Tyr Ile Leu Leu Val Ser Ser Lys
```

210 215 220

Val Ser Thr Val Lys Asp Leu Leu Pro Leu Leu Glu Lys Val Ile Gln
225 230 235 240

Ala Gly Lys Ser Leu Leu Ile Ile Ala Glu Asp Val Glu Gly Glu Ala
245 250 255

Leu Ser Thr Leu Val Val Asn Lys Ile Arg Gly Thr Phe Lys Ser Val
260 265 270

Ala Val Lys Ala Pro Gly Phe Gly Asp Arg Arg Lys Ala Met Leu Gln
275 280 285

Asp Met Ala Ile Leu Thr Gly Ala Gln Val Ile Ser Glu Glu Val Gly
290 295 300

Leu Thr Leu Glu Asn Thr Asp Leu Ser Leu Leu Gly Lys Ala Arg Lys
305 310 315 320

Val Val Met Thr Lys Asp Glu Thr Thr Ile Val Glu Gly Ala Gly Asp
325 330 335

Thr Asp Ala Ile Ala Gly Arg Val Ala Gln Ile Arg Thr Glu Ile Glu
340 345 350

Asn Ser Asp Ser Asp Tyr Asp Arg Glu Lys Leu Gln Glu Arg Leu Ala
355 360 365

Lys Leu Ala Gly Gly Val Ala Val Ile Lys Ala Gly Ala Ala Thr Glu
370 375 380

Val Glu Leu Lys Glu Arg Lys His Arg Ile Glu Asp Ala Val Arg Asn
385 390 395 400

Ala Lys Ala Ala Val Glu Glu Gly Ile Val Ala Gly Gly Gly Val Thr
405 410 415

Leu Leu Gln Ala Ala Pro Ala Leu Asp Lys Leu Lys Leu Thr Gly Asp
420 425 430

Glu Ala Thr Gly Ala Asn Ile Val Lys Val Ala Leu Glu Ala Pro Leu
435 440 445

Lys Gln Ile Ala Phe Asn Ser Gly Met Glu Pro Gly Val Val Ala Glu
450 455 460

Lys Val Arg Asn Leu Ser Val Gly His Gly Leu Asn Ala Ala Thr Gly
465 470 475 480

Glu Tyr Glu Asp Leu Leu Lys Ala Gly Val Ala Asp Pro Val Lys Val
485 490 495

Thr Arg Ser Ala Leu Gln Asn Ala Ala Ser Ile Ala Gly Leu Phe Leu
500 505 510

Thr Thr Glu Ala Val Val Ala Asp Lys Pro Glu Lys Thr Ala Ala Pro
515 520 525

Ala Ser Asp Pro Thr Gly Gly Met Gly Gly Met Asp Phe
530 535 540

( 2 ) INFORMATION FOR SEQ ID NO:35:

( i ) SEQUENCE CHARACTERISTICS:
( A ) LENGTH: 547 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:35:

Tyr Met Ala Asp Val Lys Phe Gly Ala Asp Ala Arg Ala Leu Met Leu
1 5 10 15

Gln Gly Val Asp Leu Leu Ala Asp Ala Val Ala Val Thr Met Gly Pro
20 25 30

-continued

Lys Gly Arg Thr Val Ile Ile Glu Gln Ser Trp Gly Ser Pro Lys Val
        35                  40                  45

Thr Lys Asp Gly Val Thr Val Ala Lys Ser Ile Asp Leu Lys Asp Lys
    50                  55                  60

Tyr Lys Asn Ile Gly Ala Lys Leu Val Gln Asp Val Ala Asn Asn Thr
65                  70                  75                  80

Asn Glu Glu Ala Gly Asp Gly Thr Thr Thr Ala Thr Val Leu Ala Arg
                85                  90                  95

Ser Ile Ala Lys Glu Gly Phe Glu Lys Ile Ser Lys Gly Ala Asn Pro
            100                 105                 110

Val Glu Ile Arg Arg Gly Val Asp Leu Ala Val Asp Ala Val Ile Ala
        115                 120                 125

Glu Leu Lys Lys Gln Ser Lys Pro Val Thr Thr Pro Glu Glu Ile Ala
    130                 135                 140

Gln Val Ala Thr Ile Ser Ala Asn Gly Asp Lys Glu Ile Gly Asn Ile
145                 150                 155                 160

Ile Ser Asp Ala Met Lys Lys Val Gly Arg Lys Gly Val Ile Thr Val
                165                 170                 175

Lys Asp Gly Lys Thr Leu Asn Asp Glu Leu Glu Ile Ile Glu Gly Met
            180                 185                 190

Lys Phe Asp Arg Gly Tyr Ile Ser Pro Tyr Phe Ile Asn Thr Ser Lys
        195                 200                 205

Gly Gln Lys Cys Glu Phe Gln Asp Ala Tyr Val Leu Leu Ser Glu Lys
    210                 215                 220

Lys Ile Ser Ser Ile Gln Ser Ile Val Pro Ala Leu Glu Ile Ala Asn
225                 230                 235                 240

Leu Val Leu Asn Arg Leu Lys Val Gly Leu Gln Val Val Ala Val Lys
                245                 250                 255

Ala Pro Gly Phe Leu Val Leu Asn Arg Leu Lys Val Gly Leu Gln Val
            260                 265                 270

Val Ala Val Lys Ala Pro Gly Phe Gly Asp Asn Arg Lys Asn Gln Leu
        275                 280                 285

Lys Asp Met Ala Ile Ala Thr Gly Gly Ala Val Phe Gly Glu Glu Gly
    290                 295                 300

Leu Thr Leu Asn Leu Glu Asp Val Gln Pro His Asp Leu Gly Lys Val
305                 310                 315                 320

Gly Glu Val Ile Val Thr Lys Asp Asp Ala Met Leu Leu Lys Gly Lys
                325                 330                 335

Gly Asp Lys Ala Gln Ile Glu Lys Arg Ile Gln Glu Ile Ile Glu Gln
            340                 345                 350

Leu Asp Val Thr Thr Ser Glu Tyr Glu Lys Glu Lys Leu Asn Glu Arg
        355                 360                 365

Leu Ala Lys Leu Ser Asp Gly Val Ala Val Leu Lys Val Gly Gly Thr
    370                 375                 380

Ser Asp Val Glu Val Asn Glu Lys Lys Asp Arg Val Thr Asp Ala Leu
385                 390                 395                 400

Asn Ala Thr Arg Ala Ala Val Glu Glu Gly Ile Val Leu Gly Gly Gly
                405                 410                 415

Cys Ala Leu Leu Arg Cys Ile Pro Ala Leu Asp Ser Leu Thr Pro Ala
            420                 425                 430

Asn Glu Asp Gln Lys Ile Gly Ile Glu Ile Ile Lys Arg Thr Leu Lys
        435                 440                 445

Ile Pro Ala Met Thr Ile Ala Lys Asn Ala Gly Val Asp Gly Ser Leu

-continued

```
            450                         455                         460

Ile Val Glu Lys Ile Met Gln Ser Ser Ser Glu Val Gly Tyr Asp Ala
465                     470                     475                     480

Met Ala Gly Asp Phe Val Asn Met Val Glu Lys Gly Ile Ile Asp Pro
                485                     490                     495

Thr Lys Val Val Arg Thr Ala Leu Leu Asp Ala Ala Ser Val Ala Ser
            500                     505                     510

Leu Leu Thr Thr Ala Glu Val Val Val Thr Glu Ile Pro Glu Glu Lys
        515                     520                     525

Asp Pro Gly Met Gly Ala Met Gly Gly Met Gly Gly Gly Met Gly Gly
    530                     535                     540

Gly Met Phe
545
```

( 2 ) INFORMATION FOR SEQ ID NO:36:

( i ) SEQUENCE CHARACTERISTICS:
( A ) LENGTH: 93 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:36:

```
Pro Leu Glu Asp Lys Ile Leu Val Gln Ala Gly Glu Ala Glu Thr Met
1               5                   10                  15

Thr Pro Ser Gly Leu Val Ile Pro Glu Asp Ala Lys Glu Lys Pro Gln
            20                  25                  30

Glu Gly Thr Val Val Ala Val Gly Pro Gly Arg Trp Asp Glu Asp Gly
        35                  40                  45

Ala Lys Arg Ile Pro Val Asp Val Ser Glu Gly Asp Ile Val Ile Tyr
    50                  55                  60

Ser Lys Tyr Gly Gly Thr Glu Ile Lys Tyr Asn Gly Glu Glu Tyr Leu
65                  70                  75                  80

Ile Leu Ser Ala Arg Asp Val Leu Ala Val Val Ser Lys
                85                  90
```

( 2 ) INFORMATION FOR SEQ ID NO:37:

( i ) SEQUENCE CHARACTERISTICS:
( A ) LENGTH: 94 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:37:

```
Met Lys Ile Arg Pro Leu His Asp Arg Val Val Val Arg Arg Met Glu
1               5                   10                  15

Glu Glu Arg Thr Thr Ala Gly Gly Ile Val Ile Pro Asp Ser Ala Thr
            20                  25                  30

Glu Lys Pro Met Arg Gly Glu Ile Ile Ala Val Gly Ala Gly Lys Val
        35                  40                  45

Leu Glu Asn Gly Asp Val Arg Ala Val Lys Val Gly Asp Val Val Leu
    50                  55                  60

Phe Gly Lys Tyr Ser Gly Thr Glu Val Val Val Asp Gly Lys Glu Leu
65                  70                  75                  80

Val Val Met Arg Glu Asp Asp Ile Met Gly Val Ile Glu Lys
```

85 90

( 2 ) INFORMATION FOR SEQ ID NO:38:

( i ) SEQUENCE CHARACTERISTICS:
( A ) LENGTH: 94 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:38:

Met Leu Lys Pro Leu Gly Asp Arg Ile Val Ile Glu Val Val Glu Thr
1 5 10 15

Glu Asn Lys Thr Ala Ser Gly Ile Val Leu Pro Asp Thr Ala Lys Glu
20 25 30

Lys Pro Gln Glu Gly Arg Val Val Ala Val Gly Ala Gly Arg Val Leu
35 40 45

Asp Asn Gly Gln Arg Ile Gly Arg Lys Ser Lys Val Gly Asp Arg Val
50 55 60

Ile Phe Ser Lys Tyr Ala Gly Thr Glu Val Lys Tyr Asp Gly Lys Glu
65 70 75 80

Tyr Met Ile Leu Arg Glu Ser Asp Ile Leu Ala Val Ile Arg
85 90

( 2 ) INFORMATION FOR SEQ ID NO:39:

( i ) SEQUENCE CHARACTERISTICS:
( A ) LENGTH: 94 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:39:

Met Ser Ile Lys Pro Leu Gly Asp Arg Val Val Ile Lys Arg Leu Glu
1 5 10 15

Ala Glu Glu Thr Thr Lys Ser Gly Ile Ile Val Thr Gly Thr Ala Lys
20 25 30

Glu Arg Pro Gln Glu Ala Glu Val Val Ala Val Gly Pro Gly Ala Ile
35 40 45

Val Asp Gly Lys Arg Thr Glu Met Glu Val Lys Ile Gly Asp Lys Val
50 55 60

Leu Tyr Ser Lys Tyr Ala Gly Thr Glu Val Lys Phe Glu Gly Glu Glu
65 70 75 80

Tyr Thr Ile Leu Arg Gln Asp Asp Ile Leu Ala Ile Val Glu
85 90

( 2 ) INFORMATION FOR SEQ ID NO:40:

( i ) SEQUENCE CHARACTERISTICS:
( A ) LENGTH: 97 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:40:

Met Asn Ile Arg Pro Leu His Asp Arg Val Ile Val Lys Arg Lys Glu
1 5 10 15

-continued

Val Glu Thr Lys Ser Ala Gly Gly Ile Val Leu Thr Gly Ser Ala Ala
20 25 30

Ala Lys Ser Thr Arg Gly Glu Val Leu Ala Val Gly Asn Gly Arg Ile
35 40 45

Leu Glu Asn Gly Glu Val Lys Pro Leu Asp Val Lys Val Gly Asp Ile
50 55 60

Val Ile Phe Asn Asp Gly Tyr Gly Val Lys Ser Glu Lys Ile Asp Asn
65 70 75 80

Glu Glu Val Leu Ile Met Ser Glu Ser Asp Ile Leu Ala Ile Val Glu
85 90 95

Ala ( 2 ) INFORMATION FOR SEQ ID NO:41:

( i ) SEQUENCE CHARACTERISTICS:
( A ) LENGTH: 591 base pairs
( B ) TYPE: nucleic acid
( C ) STRANDEDNESS: double
( D ) TOPOLOGY: linear ( i i ) MOLECULE TYPE: DNA (genomic)

( x i ) SEQUENCE DESCRIPTION: SEQ ID NO:41:

ATGTTAGGTC TTGTGTTATT GTATGTTGCG GTCGTGCTGA TCAGCAACGG AGTTAGTGGG 60

CTTGCAAATG TGGATGCCAA AAGCAAAGCC ATCATGAACT ACTTTGTGGG GGGGGACTCT 120

CCATTGTGTG TAATGTGGTC GCTATCATCT TATTCCACTT TCCACCCCAC CCCCCCTGCA 180

ACTGGTCCAG AAGATGTCGC GCAGGTGTCT CAACACCTCA TTAACTTCTA TGGTCCAGCG 240

ACTGGTCTAT TGTTTGGTTT TACCTACTTG TATGCTGCCA TCAACAACAC TTTCAATCTC 300

GATTGGAAAC CCTATGGCTG GTATTGCTTG TTTGTAACCA TCAACACTAT CCCAGCGGCC 360

ATTCTTTCTC ACTATTCCGA TGCGCTTGAT GATCACCGCC TCTTAGGAAT CACTGAGGGC 420

GATTGGTGGG CTTTCATTTG GCTTGCTTGG GGTGTTTTGT GGCTCACTGG TTGGATTGAA 480

TGCGCACTTG GTAAGAGTCT AGGTAAATTT GTTCCATGGC TTGCCATCGT CGAGGGCGTG 540

ATCACCGCTT GGATTCCTGC TTGGCTACTC TTTATCCAAC ACTGGTCTTG A 591

( 2 ) INFORMATION FOR SEQ ID NO:42:

( i ) SEQUENCE CHARACTERISTICS:
( A ) LENGTH: 196 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:42:

Met Leu Gly Leu Val Leu Leu Tyr Val Ala Val Val Leu Ile Ser Asn
1 5 10 15

Gly Val Ser Gly Leu Ala Asn Val Asp Ala Lys Ser Lys Ala Ile Met
20 25 30

Asn Tyr Phe Val Gly Gly Asp Ser Pro Leu Cys Val Met Trp Ser Leu
35 40 45

Ser Ser Tyr Ser Thr Phe His Pro Thr Pro Pro Ala Thr Gly Pro Glu
50 55 60

Asp Val Ala Gln Val Ser Gln His Leu Ile Asn Phe Tyr Gly Pro Ala
65 70 75 80

Thr Gly Leu Leu Phe Gly Phe Thr Tyr Leu Tyr Ala Ala Ile Asn Asn
85 90 95

-continued

Thr Phe Asn Leu Asp Trp Lys Pro Tyr Gly Trp Tyr Cys Leu Phe Val
100 105 110

Thr Ile Asn Thr Ile Pro Ala Ala Ile Leu Ser His Tyr Ser Asp Ala
115 120 125

Leu Asp Asp His Arg Leu Leu Gly Ile Thr Glu Gly Asp Trp Trp Ala
130 135 140

Phe Ile Trp Leu Ala Trp Gly Val Leu Trp Leu Thr Gly Trp Ile Glu
145 150 155 160

Cys Ala Leu Gly Lys Ser Leu Gly Lys Phe Val Pro Trp Leu Ala Ile
165 170 175

Val Glu Gly Val Ile Thr Ala Trp Ile Pro Ala Trp Leu Leu Phe Ile
180 185 190

Gln His Trp Ser
195

( 2 ) INFORMATION FOR SEQ ID NO:43:

( i ) SEQUENCE CHARACTERISTICS:
( A ) LENGTH: 199 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:43:

Lys Gly Trp Met Leu Gly Leu Val Leu Leu Tyr Val Ala Val Val Leu
1 5 10 15

Ile Ser Asn Gly Val Ser Gly Leu Ala Asn Val Asp Ala Lys Ser Lys
20 25 30

Ala Ile Met Asn Tyr Phe Val Gly Gly Asp Ser Pro Leu Cys Val Met
35 40 45

Trp Ser Leu Ser Ser Tyr Ser Thr Phe His Pro Thr Pro Pro Ala Thr
50 55 60

Gly Pro Glu Asp Val Ala Gln Val Ser Gln His Leu Ile Asn Phe Tyr
65 70 75 80

Gly Pro Ala Thr Gly Leu Leu Phe Gly Phe Thr Tyr Leu Tyr Ala Ala
85 90 95

Ile Asn Asn Thr Phe Asn Leu Asp Trp Lys Pro Tyr Gly Trp Tyr Cys
100 105 110

Leu Phe Val Thr Ile Asn Thr Ile Pro Ala Ala Ile Leu Ser His Tyr
115 120 125

Ser Asp Ala Leu Asp Asp His Arg Leu Leu Gly Ile Thr Glu Gly Asp
130 135 140

Trp Trp Ala Phe Ile Trp Leu Ala Trp Gly Val Leu Trp Leu Thr Gly
145 150 155 160

Trp Ile Glu Cys Ala Leu Gly Lys Ser Leu Gly Lys Phe Val Pro Trp
165 170 175

Leu Ala Ile Val Glu Gly Val Ile Thr Ala Trp Ile Pro Ala Trp Leu
180 185 190

Leu Phe Ile Gln His Trp Ser
195

( 2 ) INFORMATION FOR SEQ ID NO:44:

( i ) SEQUENCE CHARACTERISTICS:
( A ) LENGTH: 195 amino acids
( B ) TYPE: amino acid ( C ) STRANDEDNESS: single
( D ) TOPOLOGY: linear ( i i ) MOLECULE TYPE: protein ( x i ) SEQUENCE DESCRIPTION: SEQ ID NO:44:

| | | | | | | | | | | | | | | | |
|---|---|---|---|---|---|---|---|---|---|---|---|---|---|---|---|
| Met | Leu | Gly | Leu | Val | Leu | Leu | Tyr | Val | Gly | Ile | Val | Leu | Ile | Ser | Asn |
| 1 | | | | 5 | | | | | 10 | | | | | 15 | |
| Gly | Ile | Cys | Gly | Leu | Thr | Lys | Val | Asp | Pro | Lys | Ser | Thr | Ala | Val | Met |
| | | | 20 | | | | | 25 | | | | | 30 | | |
| Asn | Phe | Phe | Val | Gly | Gly | Leu | Ser | Ile | Ile | Cys | Asn | Val | Val | Val | Ile |
| | | 35 | | | | | 40 | | | | | 45 | | | |
| Thr | Tyr | Ser | Ala | Leu | Asn | Pro | Thr | Ala | Pro | Val | Glu | Gly | Ala | Glu | Asp |
| | 50 | | | | | 55 | | | | | 60 | | | | |
| Ile | Ala | Gln | Val | Ser | His | His | Leu | Thr | Asn | Phe | Tyr | Gly | Pro | Ala | Thr |
| 65 | | | | | 70 | | | | | 75 | | | | | 80 |
| Gly | Leu | Leu | Phe | Gly | Phe | Thr | Tyr | Leu | Tyr | Ala | Ala | Ile | Asn | His | Thr |
| | | | | 85 | | | | | 90 | | | | | 95 | |
| Phe | Gly | Leu | Asp | Trp | Arg | Pro | Tyr | Ser | Trp | Tyr | Ser | Leu | Phe | Val | Ala |
| | | | 100 | | | | | 105 | | | | | 110 | | |
| Ile | Asn | Thr | Ile | Pro | Ala | Ala | Ile | Leu | Ser | His | Tyr | Ser | Asp | Met | Leu |
| | | 115 | | | | | 120 | | | | | 125 | | | |
| Asp | Asp | His | Lys | Val | Leu | Gly | Ile | Thr | Glu | Gly | Asp | Trp | Trp | Ala | Ile |
| | 130 | | | | | 135 | | | | | 140 | | | | |
| Ile | Trp | Leu | Ala | Trp | Gly | Val | Leu | Trp | Leu | Thr | Ala | Phe | Ile | Glu | Asn |
| 145 | | | | | 150 | | | | | 155 | | | | | 160 |
| Ile | Leu | Lys | Ile | Pro | Leu | Gly | Lys | Phe | Thr | Pro | Trp | Leu | Ala | Ile | Ile |
| | | | | 165 | | | | | 170 | | | | | 175 | |
| Glu | Gly | Ile | Leu | Thr | Ala | Trp | Ile | Pro | Ala | Trp | Leu | Leu | Phe | Ile | Gln |
| | | | 180 | | | | | 185 | | | | | 190 | | |
| His | Trp | Val | | | | | | | | | | | | | |
| | | 195 | | | | | | | | | | | | | |

IMMUNOGENIC COMPOSITIONS AGAINST HELICOBACTER INFECTION, POLYPEPTIDES FOR USE IN THE COMPOSITIONS, AND NUCLEIC ACID SEQUENCES ENCODING SAID POLYPEPTIDES

CROSS-REFERENCE TO RELATED APPLICATIONS

This application is a continuation of application Ser. No. 08/447,177 filed May 19, 1995, which is a continuation-in-part of application Ser. No. 08/432,697, filed May 2, 1995, which is a continuation-in-part of International Application PCT/EP94/01625, filed 19 May 1994, which is based on International Application PCT/EP93/03259, filed 19 Nov. 1993, and European Application No. 93 401 309.5, filed 19 May 1993. Applicants claim the benefits of the International filing dates and priority of the European filing date. The entire disclosure of each of these applications is relied upon and incorporated by reference herein.

BACKGROUND OF THE INVENTION

The present invention relates to immunogenic compositions for inducing protective antibodies against Helicobacter spp. infection. It also relates to proteinaceous material derived from Helicobacter, and to nucleic acid sequences encoding them. Antibodies to these proteinaceous materials are also included in the invention.

*H. pylori* is a microorganism, which infects human gastric mucosa and is associated with active chronic gastritis. It has been shown to be an aetiological agent in gastroduodenal ulceration (Peterson, 1991), and two recent studies have reported that persons infected with *H. pylori* had a higher risk of developing gastric cancer (Nomura et al., 1991; Parsonnet et al., 1991).

In vivo studies of the bacterium, and consequently, work on the development of appropriate preventive or therapeutic agents, has been severely hindered by the fact that *Helicobacter pylori* only associates with gastric-type epithelium from very few animal hosts, none of which are suitable for use as laboratory models.

A mouse model of gastric colonization has been developed using a helical bacterium isolated from cat gastric mucus (Lee et al., 1988, 1990) and identified as a member of the genus Helicobacter. It has been named *H. felis* (Paster et al., 1990).

To date, only limited information concerning *H. felis* and the extent of its similarities and differences with *H. pylori* is available. The reliability of the mouse model for the development of treatments for *H. pylori* infection is, therefore, uncertain. Recently, it was shown that *H. pylori* urease is a protective antigen in the *H. felis*/mouse model (Davin et al., 1993; Corthesy-Theulaz et al., 1993).

It is, therefore, an aim of the present invention to provide therapeutic and preventive compositions for use in Helicobacter infection, which furthermore can be tested in laboratory animals.

It is known that *H. pylori* expresses urease activity and that urease plays an important role in bacterial colonization and mediation of certain pathogenic processes (Ferrero and Lee, 1991; Hazel et al., 1991).

The genes coding for the urease structural polypeptides of *H. pylori* (UreA (SEQ ID NO:22), UreB (SEQ ID NO:26)) have been cloned and sequenced (Labigne et al., 1991; and French Patent Application FR 8813135), as have the genes coding the "accessory" polypeptides necessary for urease activity in *H. pylori* (International patent application WO 93/07273).

Attempts have been made to use nucleic acid sequences from the *H. pylori* urease gene cluster as probes to identify urease sequences in *H. felis*. However, none of these attempts have been successful. Furthermore, the establishment and maintenance of *H. felis* cultures in vitro is extremely difficult, and the large quantities of nucleases present in the bacteria complicates the extraction of DNA.

SUMMARY OF THE INVENTION

The present inventors have, however, succeeded in cloning and sequencing the genes of the urease structural polypeptides of *H. felis*, and of the accessory polypeptides. This has enabled, in the context of the invention, the comparison of the amino acid sequence data for the *H. felis* Ure gene products with that for *Helicobacter pylori*, and a high degree of conservation between the urease sub-units has been found. An immunological relationship between the two ureases exists, and protective antibodies to Helicobacter infection can be induced using the urease sub-units or fragments thereof as immunogens.

Indeed, to elucidate the efficiency of individual urease subunits to act as mucosal immunogens, the genes encoding the respective urease sub-units (UreA (SEQ ID NOS: 20,22) and UreB (SEQ ID NOS:21,26) of *Helicobacter pylori* and *Helicobacter felis* have been cloned in an expression vector (pMAL) and expressed in *Escherichia coli* cells as translational fusion proteins. The recombinant UreA (SEQ ID NOS:20,22) and UreB (SEQ ID NOS:21,26) proteins have been purified by affinity and anion exchange chromatography techniques, and have predicted molecular weights of approximately 68 and 103 kDa, respectively. Western blotting studies indicated that the urease components of the fusion proteins are strongly immunogenic and are specifically recognized by polyclonal rabbit anti-Helicobacter sera. Orogastric immunization of mice with 50 μg of recombinant *H. felis* UreB (SEQ ID NO:21), administered in combination with a mucosal adjuvant (cholera toxin), protected 60% (n=7; p<0.005) of mice from gastric colonization by *H. felis* bacteria at over 4 months. This compared with a value of 25% (n=8; p>0.05) for the heterologous *H. pylori* UreB (SEQ ID NO:26) antigen. For the first time, a recombinant subunit antigen has been shown to induce an immunoprotective response against gastric Helicobacter infection.

The inventors have also identified, in the context of the invention, new heat shock proteins or chaperonins in Helicobacter, which have an enhancing effect on urease activity. Use of the chaperonins in an immunogenic composition may induce therefore an enhancement of protection.

Indeed, the genes encoding each of the HspA (SEQ ID NO:29) and HspB (SEQ ID NO:30) polypeptides of *Helicobacter pylori* have been cloned, expressed independently as fused proteins to the Maltose-Binding-Protein (MBP), and purified on a large scale. These proteins have been used as recombinant antigens to immunize rabbits, and in Western immunoblotting assays as well as ELISA, to determine their immunogenicity in patients infected with HP (HP+). The MBP-HspA (SEQ ID NO:29) and MBP-HspB (SEQ ID NO:30) fusion proteins have been shown to retain their antigenic properties. Comparison of the humoral immune response against HspA (SEQ ID NO:29) and/or HspB (SEQ ID NO:30) in (HP+) patient sera demonstrated that not only HspB (SEQ ID NO:30) but also HspA (SEQ ID NO:29) was recognized by (HP+) patient sera (29/38 and 15/38, respectively). None of the 14 uninfected patients had antibodies reacting with the Hsps.

BRIEF DESCRIPTION OF THE DRAWINGS

This invention will be described in greater detail by reference to the following drawings.

A) Extracts were of *E. coli* cells harboring: plasmid vector pILL570 (lane 1); recombinant plasmid pILL205, described in Molec. Microb. 1993, 9:323–333 (lane 2); and pILL205 derivative plasmids disrupted in loci "a", "b", "c", "d", and "e" (lanes 3–7).

B) Extracts were of *E. coli* cells harboring: recombinant plasmid pILL753 containing the *H. pylori* ure A and ure B genes (Labigne et al., 1991) (lane 1); and pILL205 derivative plasmids disrupted in loci "f", "g", "h", and "i" (lanes 2–5). The small arrow heads indicate polypeptides of approximately 30 and 66 kilodaltons, which represent putative UreA (SEQ ID NO:20) and UreB (SEQ ID NO:21) gene products of *H. felis*. The large arrow heads in panel B indicate the corresponding gene products of *H. pylori*, which cross-reacted with the anti-*H. felis* serum. The numbers indicate the molecular weights (in thousands) of the protein standards.

FIG. 3. Nucleotide sequence of the *H. felis* structural urease genes (SEQ ID NO:19). Numbers above the sequence indicate the nucleotide positions as well as the amino acid position in each of the two UreA (SEQ ID NO:20) and UreB (SEQ ID NO:21) polypeptides. Predicted amino acid sequences for UreA (bp 43 to 753) and UreB (766 to 2616) are shown below the sequence. The putative ribosome-binding site (Shine-Dalgarno sequence, SD) is underlined.

FIG. 4. Comparison of sequences for the structural urease genes of *H. felis* (SEQ ID NOS:20–21) to:

a) the sequence of the two subunits of *H. pylori* urease (SEQ ID NOS:22,26) (Labigne et al., 1991);

b) the sequence of the three subunits of *Proteus mirabilis* urease (SEQ ID NOS:23–24,27) (Jones and Mobley, 1989);

c) the sequence of the single subunit of jack bean urease (SEQ ID NO:25). Margin gaps (shown by dashes) have been introduced to ensure the best alignment. *, amino acids identical to those of the *H. felis* sequence; =, amino acids shared by the various ureases; , amino acids unique to the Helicobacter ureases. The percentages relate to the number of amino acids that are identical to those of the *H. felis* urease subunits. H.f., *Helicobacter felis*; H.p., *Helicobacter pylori*; P.m., *Proteus mirabilis*; J.b., Jack bean.

Figure 5:
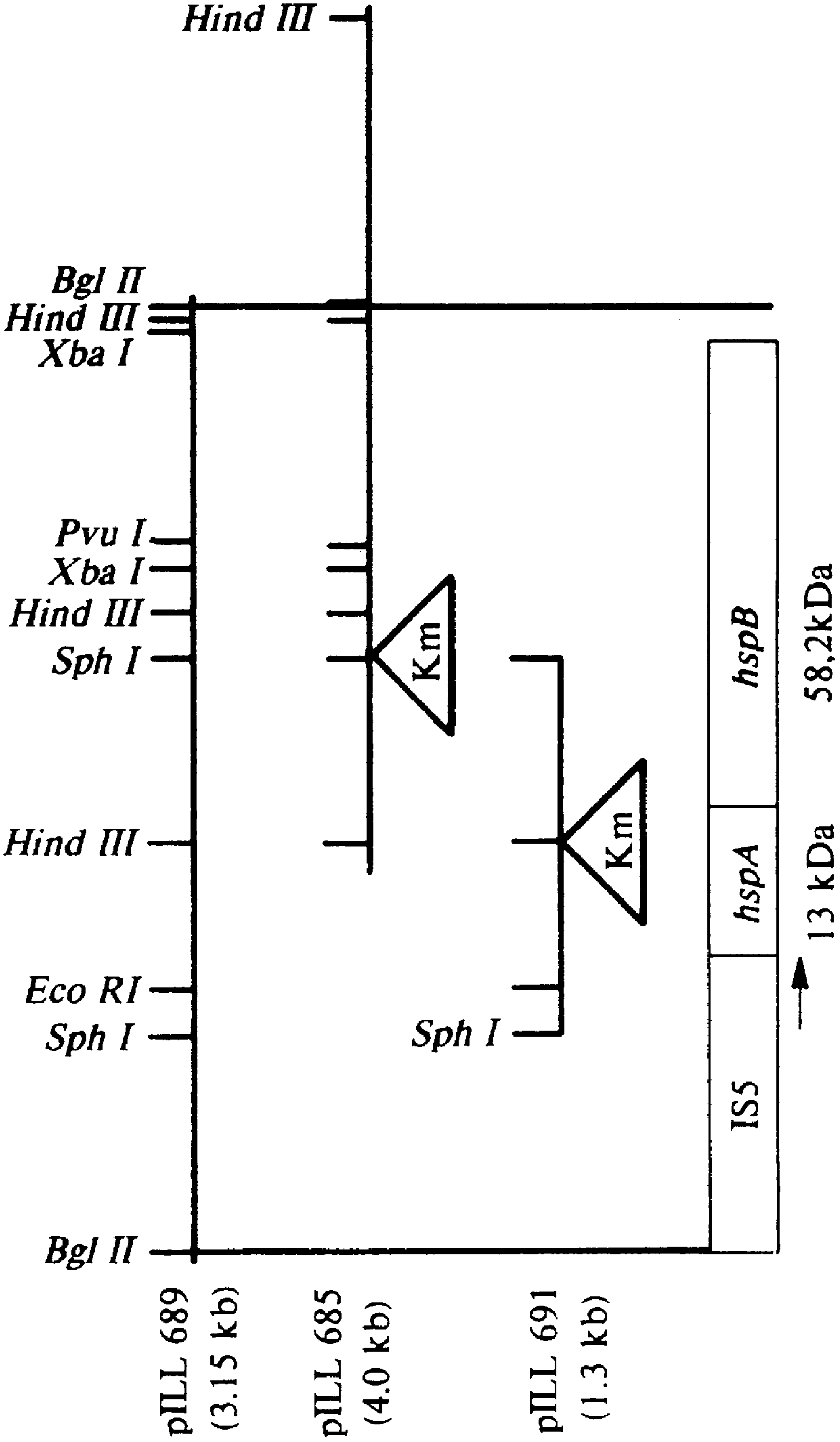

FIG. 5. Restriction map of the recombinant plasmids pILL689, pILL685, and pILL691. The construction of these plasmids is described in detail in Table 5. Km within triangles depicts the site of insertion of the kanamycin cassette, which led to the construction of plasmids pILL687, pILL688, and pILL696 (Table 5). Boxes underneath the maps indicate the position of the three genetic elements deduced from the nucleotide sequence, namely IS5, hsp A and hsp B.

FIG. 6. Nucleotide sequence of the *Helicobacter pylori* heat shock protein gene cluster (SEQ ID NO:28). The first number above the sequence indicates the nucleotide positions, whereas the second one numbers the amino acid residue position for each of the HspA (SEQ ID NO:29) and HspB (SEQ ID NO:30) protein. The putative ribosome-binding sequences (Shine-Dalgarno [SD] sites) are underlined.

FIG. 7. Comparison of the deduced amino-acid sequence of *Helicobacter pylori* HspA (SEQ ID NO:29) (A) or HspB (SEQ ID NO:30) (B) with that of other GroEL-like (SEQ ID NOS:31–35) (A) or GroES-like (SEQ ID NO:36–40) (B) proteins. Asterisks mark amino acids identical with those in the *Helicobacter pylori* HspA (SEQ ID NO:29) or HspB (SEQ ID NO:30) sequences.

Figure 8:
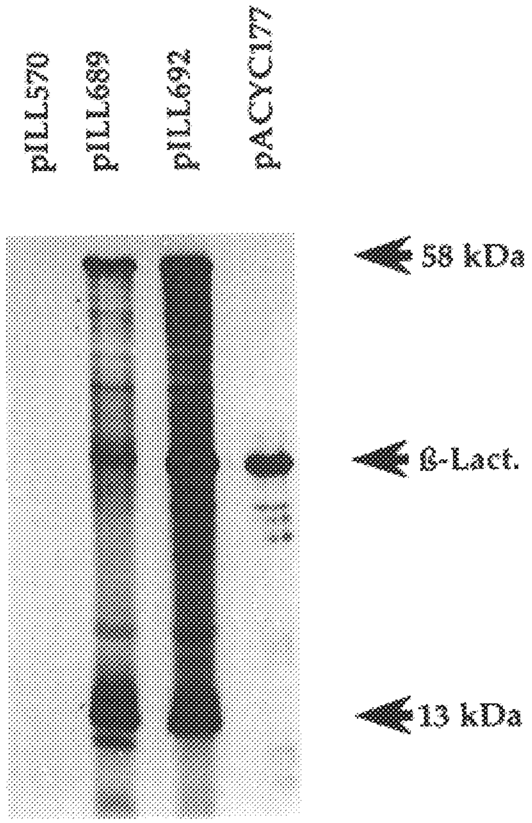

FIG. 8. Expression of the *Helicobacter pylori* HspA heat shock proteins (SEQ ID NO:29) in *E. coli* minicells. The protein bands with apparent molecular masses of 58 and 13 kDA, corresponding to the *Helicobacter pylori* HspA (SEQ ID NO:29) and HspB (SEQ ID NO:30) heat shock proteins are clearly visible in the lanes corresponding to plasmids pILL689 and pILL692 and absent in the vector controls (pILL570 and pACYC177, respectively).

FIG. 9. Nucleotide sequence of the *Helicobacter felis* Ure I gene (SEQ ID NO:41) and deduced amino acid sequence (SEQ ID NO:42).

FIG. 10. Comparison of the amino acid sequence of the Ure I proteins deduced from the nucleotide sequence of the Ure I gene of *Helicobacter felis* (SEQ ID NO:43) and that of *Helicobacter pylori* (SEQ ID NO:44).

FIG. 11. Genetic code. Chain-terminating, or "nonsense", codons. Also used to specify the initiator formyl-Met-tRNA$^{Met}_{F}$. The Val triplet GUG is therefore "ambiguous" in that it codes both valine and methionine.

FIG. 12. Signification of the one-letter and three-letter amino-acid abbreviations.

Figure 13:
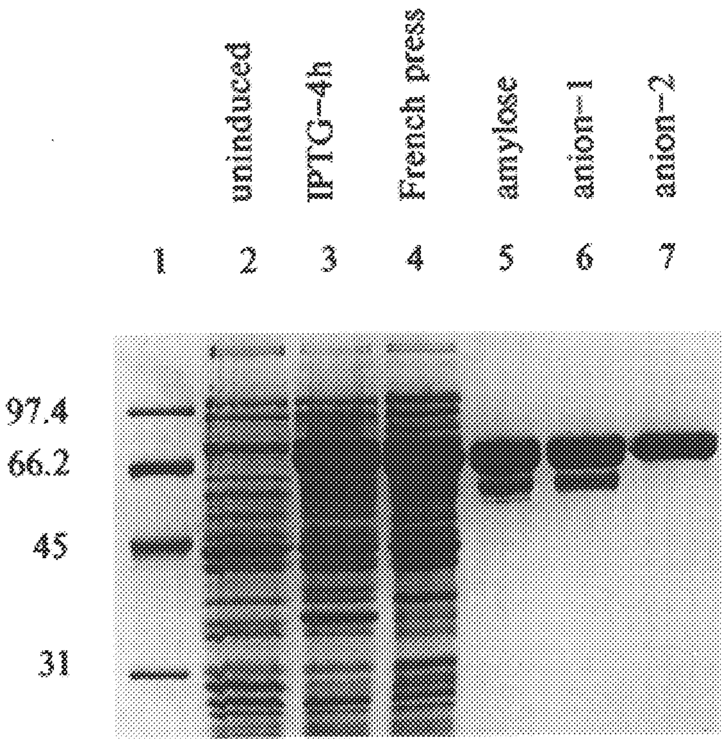

FIG. 13. Purification of *H. pylori* UreA-MBP (SEQ ID NO:22) recombinant protein using the pMAL expression vector system. Extracts from the various stages of protein purification were migrated on a 10% resolving SDS-polyacrylamide gel. Following electrophoresis, the gel was stained with Coomassie blue. The extracts were: 1) non-induced cells; 2) IPTG-induced cells; French press lysate of induced cell extract; 5) eluate from amylose resin column; 6) eluate from anion exchange column (first passage); 7) eluate from anion exchange column (second passage); and 8) SDS-PAGE standard marker proteins.

Figure 14:
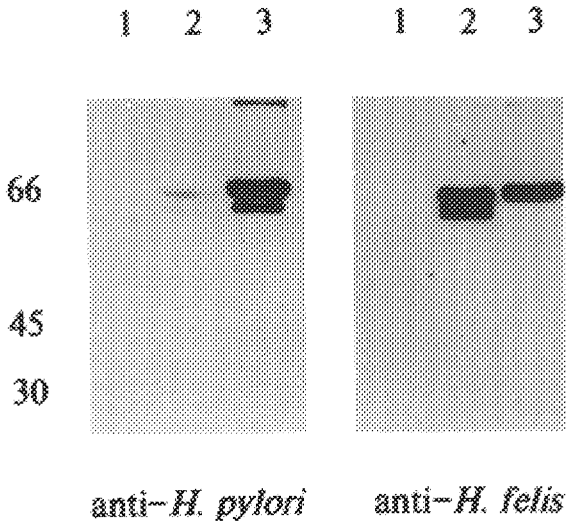

FIG. 14. Recognition of UreA recombinant fusion proteins by polyclonal rabbit anti-Helicobacter sera. Protein extracts of maltose-binding protein (MBP, lane 1), *H. felis* UreA-MBP (SEQ ID NO:20) (lane 2), and *H. pylori* UreA-MBP (SEQ ID NO:22) (lane 3) were Western blotted using rabbit polyclonal antisera (diluted 1:5000) raised against whole cell extracts of *H. pylori* and *H. felis*. The purified fusion proteins are indicated by an arrow. Putative degradation products of the proteins are shown by an asterisk.

Figure 15:
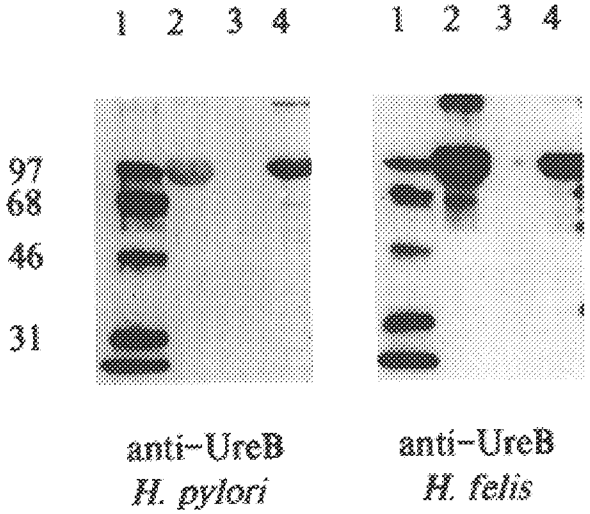

FIG. 15. Recognition of UreB recombinant fusion proteins by rabbit antisera raised against purified homologous and heterologous UreB proteins. Nitrocellulose membranes were blotted with the following extracts: 1) standard protein markers; 2) *H. felis* UreA-MBP (SEQ ID NO:20); 3) MBP; 4) *H. pylori* UreA-MBP (SEQ ID NO:22). The membranes were reacted with polyclonal rabbit antisera (diluted 1:5000) raised against MBP-fused *H. pylori* and *H. felis* UreB (SEQ ID NOS:26,21) sub-units, respectively. The molecular weights of standard proteins are presented on the left-hand side of the blots.

Figure 16:
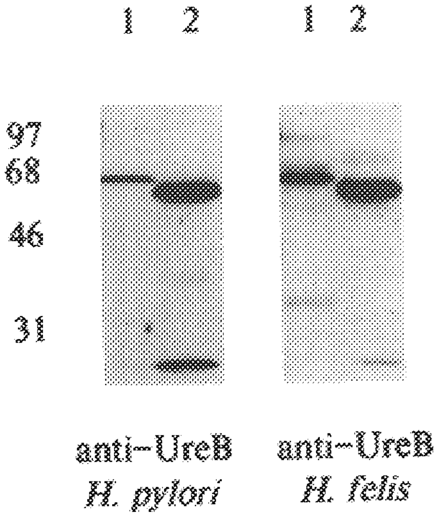

FIG. 16. Western blot analysis of *H. pyloni* and *H. felis* whole cell extracts with antisera raised against purified UreB MBP-fused recombinant proteins. SDS-PAGE whole extracts of *H. Felis* (lane 1) and *H. pylori* (lane 2) cells were reacted with polyclonal rabbit antisera raised against purified *H. pylori* UreB (SEQ ID NO:26) and *H. felis* UreB (SEQ ID NO:21) MBP-fused proteins (sera diluted 1:5000). The difference in gel mobility of the respective non-recombinant UreB sub-units of *H. felis* and *H. pylori* can be seen. The numbers on the left refer to the molecular weights of standard marker proteins.

Figure 17:
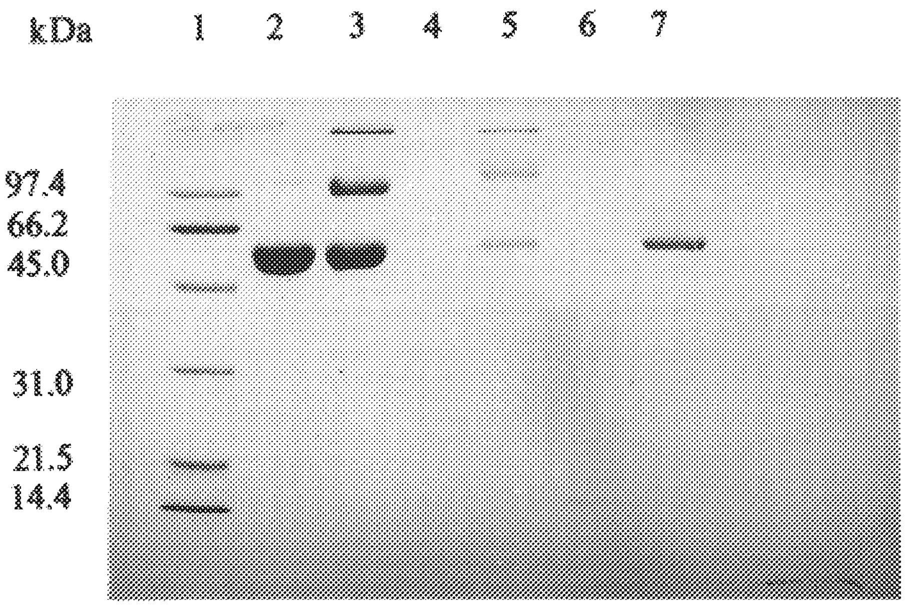

FIG. 17. SDS-PAGE analysis of material eluted from the amylose column (lanes 2 and 3) or from the Ni-NTA column following elution: with buffer E (pH 4.5), lanes 4 and 5; or buffer C (pH 6.3), lanes 6 and 7. Material eluted from a lysate of MC1061 (PILL933) (lanes 2, 3, 5, and 7) and material eluted from a lysate of MC1061 (PMAL-c2) (lanes 4 and 6). Lane 3 contains the same material as in lane 2 except that it was resuspended in buffer E, thus demonstrating that buffer E is responsible for dimer formation of the MBP-HspA subunit, as seen in lanes 3 and 5.

Figure 18A:
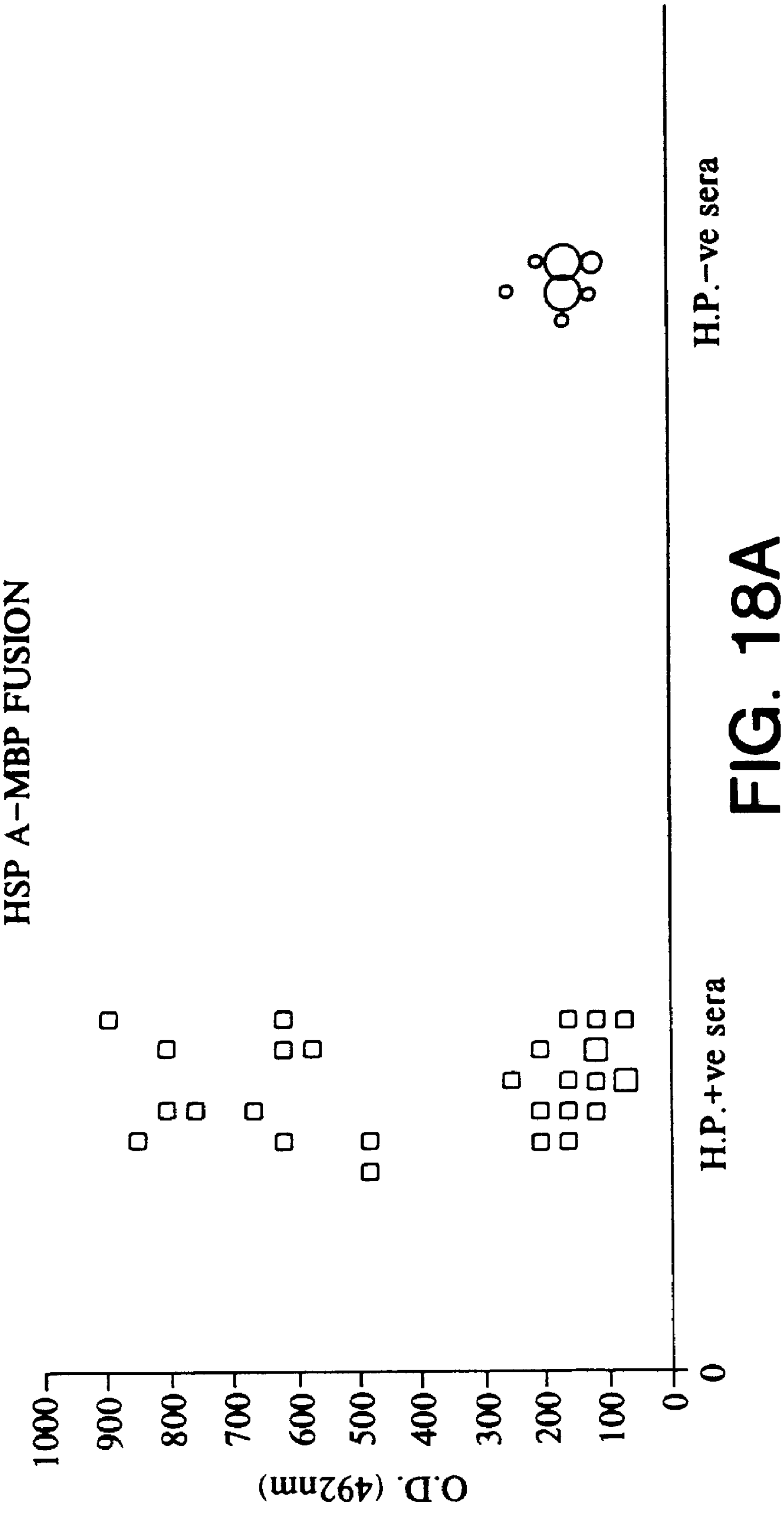
Figure 18B:
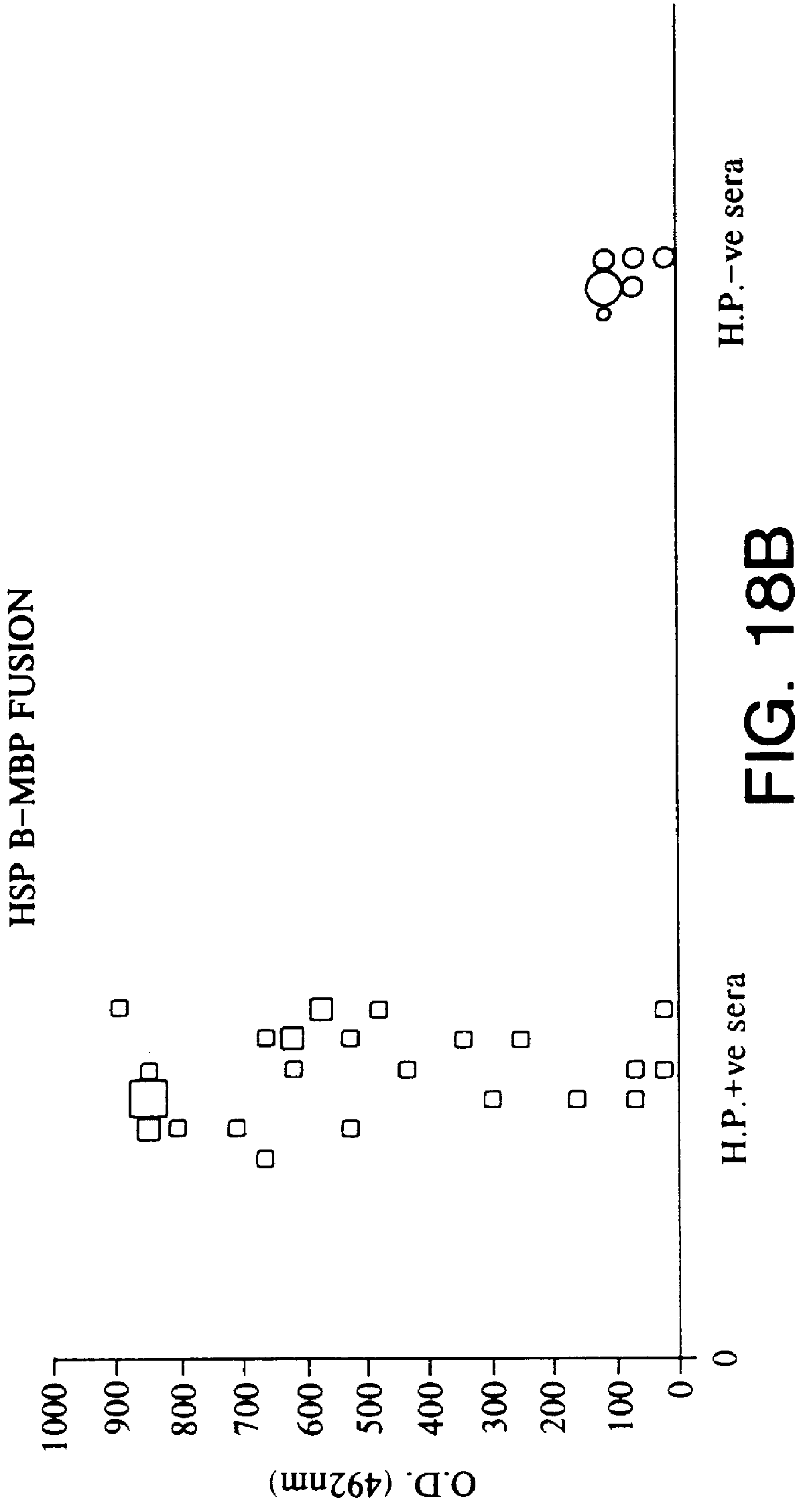
Figure 18C:
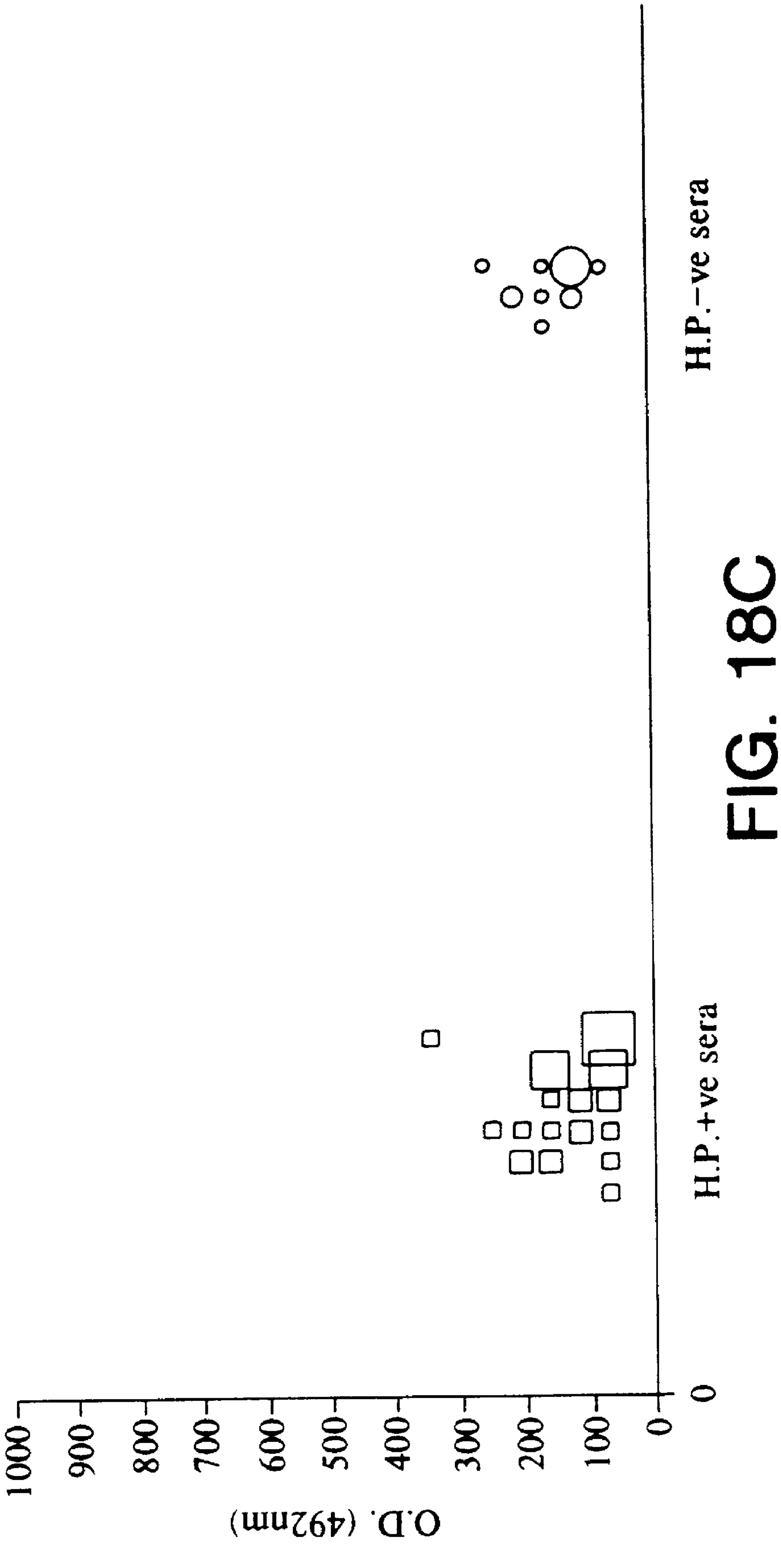

FIG. 18. Serum IgG responses to MBP (bottom), MBP-HspA (SEQ ID NO:29) (top) and MBP-HspB (SEQ ID NO:30) (middle) of 28 *H. pylori* infected patients (squares, left) and 12 uninfected patients (circles, right). The optical density of each serum in the ELISA assay described in Experimental Procedures was read at 492 nm, after a 30 mn incubation. The sizes of the symbols are proportional to the number of sera giving the same optical density value.

Figure 19:
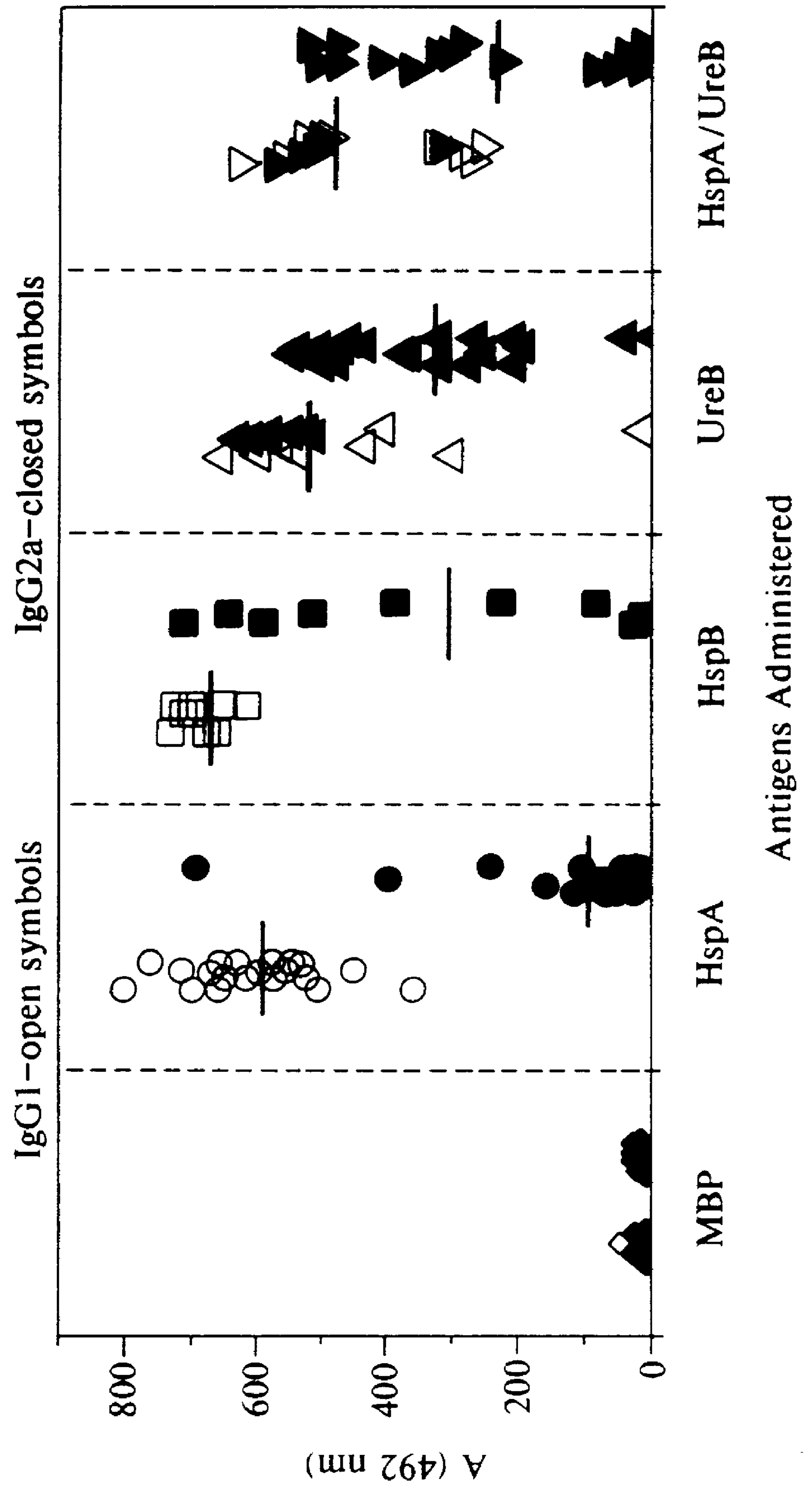

FIG. 19. Measurement by ELISA of serum antibodies ($IgG_1$ and $IgG_{2a}$ isotypes) in mice immunized with recombinant *H. pylori* antigens. $A_{492}$ values for individual serum samples (diluted 1:100) are presented. Horizontal lines represent the mean $A_{492}$ values for each set of data.

Figure 20A:
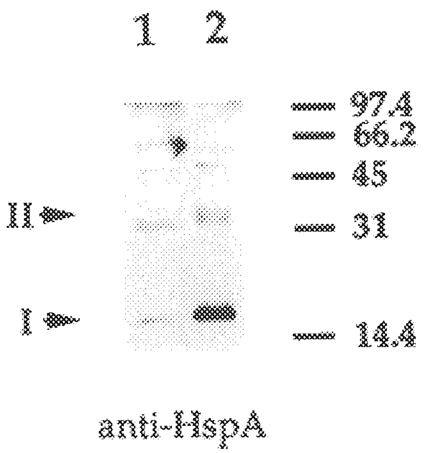
Figure 20B:
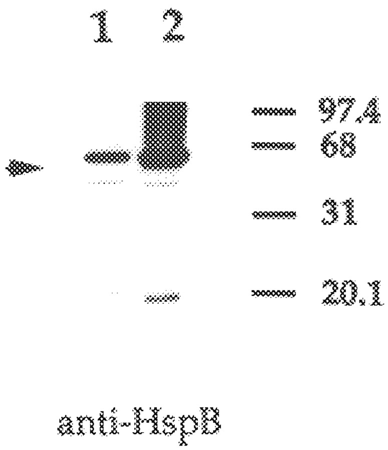

FIG. 20. Immunoblot analyses of total cell extracts of *H. felis* (lane 1) and *H. pylori* (lane 2) using rabbit antisera raised against recombinant *H. pylori* HspA (SEQ ID NO:29) and HspB (SEQ ID NO:30) antigens (dilution 1:5000). Arrows refer to cross-reactive proteins: (I) monomeric and (II) dimeric forms of HspA antibody-reactive proteins are indicated. Protein standards are indicated on the right-hand side of each of the blots (numbers are in kDa). Immunoreactants on the anti-HspA blotted membrane were revealed directly with a peroxidase-labelled secondary antibody, whilst antigens on the anti-HspB were detected using a biotinylated secondary antibody/streptavidin-peroxidase procedure. The latter was found to give higher background staining and when used to detect immunoreactants on membranes blotted with the anti-HspA antibody, produced very weak signals.

DETAILED DESCRIPTION OF PREFERRED EMBODIMENT

The present invention concerns an immunogenic composition capable of inducing antibodies against Helicobacter infection characterized in that it comprises:

i) at least one sub-unit of a urease structural polypeptide from *Helicobacter pylori* (SEQ ID NOS:22,26), or a fragment thereof, defined by two restriction sites or comprised between 6 to 100 amino acids or delineated by two specific oligonucleotides targeting any sequence of 300 bp, said fragment being recognized by antibodies reacting with *Helicobacter felis* urease (SEQ ID NOS:20–21), and/or at least one sub-unit of a urease structural polypeptide from *Helicobacter felis* (SEQ ID NOS:20–21), or a fragment thereof, said fragment being recognized by antibodies reacting with *Helicobacter pylori* urease (SEQ ID NOS:22,26);

ii) and/or a Heat Shock protein (Hsp), or chaperonin, from Helicobacter, or a fragment of said protein.

Preferably, the immunogenic composition is capable of inducing protective antibodies.

According to a preferred embodiment, the immunogenic composition of the invention contains, as the major active ingredient, at least one sub-unit of a urease structural polypeptide from *Helicobacter pylori* (SEQ ID NOS:22,26) and/or *Helicobacter felis* (SEQ ID NOS:20–21). The expression "urease structural polypeptide" signifies, in the context of the present invention, the enzyme of *Helicobacter pylori* (SEQ ID NOS:22,26) or *Helicobacter felis* (SEQ ID NOS:20–21), probably a major surface antigen composed of two repeating monomeric sub-units, a major sub-unit (product of the UreB (SEQ ID NOS:21,26) gene) and a minor sub-unit product of the UreA (SEQ ID NOS:20,22) gene, and which, when complemented by the presence of the products of the accessory genes of the urease gene cluster, are responsible for urease activity i.e., the hydrolysis of urea to liberate $NH_4^+$ in the two Helicobacter species. It is to be understood that in the absence of the accessory gene products, the urease structural polypeptides do not exhibit enzymatic activity, but are recognized by antibodies reacting with *H. felis* or *H. pylori* urease.

The term "immunogenic composition" signifies, in the context of the invention, a composition comprising a major active ingredient as defined above, together with any necessary ingredients to ensure or to optimize an immunogenic response, for example adjuvants, such as mucosal adjuvant, etc.

The *Helicobacter pylori* urease structural polypeptide has been described and sequenced by Labigne et al., 1991. The polypeptide described in this paper is particularly appropriate for use in the composition of the present invention. However, variants showing functional homology with this published sequence may be used, which comprise amino acid substitutions, deletions or insertions provided that the immunological characteristics of the polypeptide insofar as its cross-reactivity with anti-*Helicobacter felis* urease antibodies is concerned, are maintained. Generally speaking, thy polypeptide variant will show a homology of at least 75% and preferably about 90% with the included sequence.

A fragment of the *Helicobacter pylori* urease structural polypeptide may also be used in the immunogenic composition of the invention, or at least one sub-unit of a urease structural polypeptide from *Helicobacter pylori*, or a fragment thereof, defined by two restriction sites or comprised between 6 to 100 amino acids or delineated by two specific oligonucleotides targeting any sequence of 300 bp, provided that the fragments are recognized by antibodies reacting with *Helicobacter felis* urease. Such a fragment will generally be comprised of at least 6 amino acids, for example, from 6 to 100 amino acids, preferably about 20–25. Advantageously, the fragment carries epitopes unique to Helicobacter.

Nucleic acid and amino-acid sequences may be interpreted in the context of the present invention by reference to FIGS. 11 and 12, showing the genetic code and amino acid abbreviations respectively.

The *Helicobacter felis* urease structural polypeptide suitable for use in the present invention is preferably that encoded by part of the plasmid pILL205 (deposited at the CNCM on 25th Aug. 1993, under number: CNCM I-1355), and whose amino acid sequence is shown in FIG. 3 (SEQ ID NOS:20–21) (subunits A and B). Again, a variant of this polypeptide comprising amino acid substitutions, deletions or insertions with respect to the FIG. 3 sequence may be used provided that the immunological cross-relationship with *Helicobacter pylori* urease is maintained. Such a variant normally exhibits at least 90% homology or identity with the FIG. 3 sequence. An example of such variants are the urease A (SEQ ID NO:20) and B (SEQ ID NO:21) sub-units from *Helicobacter heilmannii* (Solnick et al., 1994), shown to have 80% and 92% identity with the *H. felis* urease A and B sub-units, respectively.

Fragments of this urease or variants may be used in the immunogenic composition provided that the fragments are recognized by antibodies reacting with *Helicobacter pylori* urease. Again, the length of such a fragment is usually at least 6 amino acids, for example, from 6 to 100, preferably about 20 to 25. Preferably, the fragment carries epitopes unique to Helicobacter.

If variants or fragments of the native urease sequences are employed in the immunogenic composition of the invention, their cross-reactivity with antibodies reacting with urease from the other Helicobacter species can be tested by contacting the fragment or the variant with antibodies, preferably polyclonal raised to either the native or the recombinant urease or, alternatively, to whole Helicobacter. Preferably, the variants and fragments give rise to antibodies which are also capable of reacting with *H. heilmannii* urease. Cross protection to infection by *H. heilmannii* is therefore also obtained by the immunogenic composition of the invention.

The use of fragments of the urease structural genes is particularly preferred since the immunological properties of the whole polypeptide may be conserved whilst minimizing risk of toxicity.

The active component of the immunogenic composition of the invention may be comprised of one sub-unit only of the urease structural polypeptide, that is either sub-unit A or sub-unit B products of the UreA (SEQ ID NOS:20,22) and UreB (SEQ ID NOS:21,26) genes, respectively. Compositions comprising only the urease sub-unit UreB, of either *H. pylori* or *H. felis*, or variants and fragments as defined above, are particularly advantageous. Most preferred are homologous systems wherein the urease sub-unit, particularly sub-unit B, is derived from the organism against which protection is sought, e.g., *H. felis* sub-unit B against *H. felis* infection. However, the composition may contain both A and B sub-units, which are normally present as distinct polypeptides. However, it is possible, when the polypeptide is produced by recombinant means, to use a fusion protein comprising the entire sequences of the A and B gene products by the suppression of the stop-codon separating the two adjacent coding sequences.

The urease component of the immunogenic composition, whether sub-unit A or sub-unit B, may be used in the form of translational fusion proteins, for example with the Maltose-Binding-Protein (MBP). Other suitable fusions are exemplified in International Patent Application WO 90/11360. Another example of a suitable fusion protein is the "QIAexpress" system commercialized by QIAGEN, USA, which allows the 6xHis tag sequence to be placed at the 5' or 3' end of the protein coding sequence. The use of the active ingredients in the form of fusion proteins is, however, entirely optional.

According to a further preferred embodiment, the immunogenic composition of the invention may comprise in addition to or instead of the urease structural polypeptide defined above, a Heat Shock Protein also known as a "chaperonin" from Helicobacter. These chaperonins have been elucidated by the inventors in the context of the present invention. Preferably, the chaperonin is from *Helicobacter pylori*. Such an Hsp may be the urease-associated HspA (SEQ ID NO:29) or HspB (SEQ ID NO:30) or a mixture of the two, having the amino acid sequence illustrated in FIG. 6. These polypeptides are encoded by the plasmid pILL689 (deposited at CNCM on 25th Aug. 1993, under number: CNCM I-1356). Particularly preferred is the *H. pylori* HspA (SEQ ID NO:29) protein, either alone or in combination with HspB (SEQ ID NO:30).

It is also possible to use, as Hsp component, according to the invention, a polypeptide variant in which amino acids of the FIG. 6 sequence (SEQ ID NOS:29–30) have been replaced, inserted or deleted, the said variant normally exhibiting at least 75%, and preferably at least 85% homology with the native Hsp. The variants preferably exhibit at least 75%, for example at least 85% identity with the native Hsp.

The variants may further exhibit functional homology with the native polypeptide. In the case of the Hsp components, "functional homology" means the capacity to enhance urease activity in a microorganism capable of expressing active urease, and/or the capacity to block infection by Helicobacter, particularly *H. felis* and *H. pylori*. The property of enhancing urease activity may be tested using the quantitative urease activity assay described below in the examples. Fragments of either or both of the HspA and HspB polypeptides, preferably having at least 6 amino acids, may be used in the composition. The fragments or variants of the Hsp component used in the immunogenic composition of the invention are preferably capable of generating antibodies, which block the infection against *H. pylori* or *H. felix*. The presence of the chaperonins in the composition enhances the protection against *Helicobacter pylori* and *felis*.

The Hsp component of the immunogenic composition, whether HspA or HspB, can be used in the form of a translational fusion protein, for example with the Maltose-Binding-Protein (MBP). As for the urease component, other suitable fusion partners are described in International patent application WO 90/11360. The "QIAexpress" system of QIAGEN, USA, may also be used. Again, the use of the proteins in the form of fusion proteins is entirely optional.

According to the invention, therefore, the immunogenic composition may comprise either a urease structural polypeptide as defined above, or a Helicobacter Hsp, particularly HspA or a combination of these immunogens.

According to a preferred embodiment, the immunogenic composition comprises, as urease component or a fragment thereof, both the A (SEQ ID NO:20) and/or B (SEQ ID NO:21) sub-units or fragments of urease of *Helicobacter felis* (i.e., without *H. pylori* urease) the urease component can be associated or not to the HspA (SEQ ID NO:29) and/or HspB (SEQ ID NO:30) of *Helicobacter pylori*. Alternatively, the A (SEQ ID NO:20) and B (SEQ ID NO:21) sub-units of the *Helicobacter felis* urease may be used together with those of *H. pylori* (SEQ ID NOS:22,26), but without chaperonin component.

The immunological cross-reactivity between the ureases of the two different Helicobacter species enables the use of one urease only in the composition, preferably that of *Helicobacter felis*. The protective antibodies induced by the common epitopes will, however, be active against both *Helicobacter pylori* and *Helicobacter felis*. It is also possible that the composition induce protective antibodies to other species of Helicobacter if the urease polypeptide or fragment carries epitopes occurring also on those other species.

The composition of the invention is advantageously used as an immunogenic composition or a vaccine, together with physiologically acceptable excipients and carriers and, optionally, with adjuvants, haptens, carriers, stabilizers, etc. Suitable adjuvants include muramyl dipeptide (MDP), complete and incomplete Freund's adjuvants (CFA and IFA) and alum. The vaccine compositions are normally formulated for oral administration.

The vaccines are preferably for use in man, but may also be administered in non-human animals, for example for veterinary purposes, or for use in animals such as mice, cats and dogs.

The immunogenic compositions administered by suitable routes into animals raises the synthesis in vivo of specific antibodies, which can be used for therapeutic purposes, for example in passive immunity.

The invention also relates to the proteinaceous materials used in the immunogenic composition and to proteinaceous material encoded by the urease gene clusters other than the A and B urease structural sub-units. "Proteinaceous material" means any molecule comprised of chains of amino acids, e.g., peptides, polypeptides or proteins, fusion or mixed proteins (i.e. an, association of 2 or more proteinaceous materials, all or some of which may have immunogenic or immunomodulation properties), either purified or in a mixture with other proteinaceous or non-proteinaceous material. "Polypeptide" signifies a chain of amino acids whatever its length and englobes the term "peptide". The term "fragment" means any amino acid sequence shorter by at least one amino acid than the parent sequence and comprising a length of amino acids, e.g., at least 6 residues, consecutive in the parent sequence.

The peptide sequences of the invention, may for example, be obtained by chemical synthesis, using a technique such as the Merrifield technique and synthesizer of the type commercialize by Applied Biosystems.

In particular, the invention relates to proteinaceous material characterized in that it comprises at least one of the *Helicobacter felis* polypeptides encoded by the urease gene cluster of the plasmid pILL205 (CNCM I-1355), including the structural and accessory urease polypeptides, or a polypeptide having at least 90% homology with said polypeptides, or a fragment thereof. Of particular interest are the gene products of the ureA (SEQ ID NO:20) and ureB (SEQ ID NO:21) genes, as illustrated in FIG. 3, or a variant thereof having at least 90% homology or a fragment having at least 6 amino acids. The fragments and the variants are recognized by antibodies reacting with *Helicobacter pylori* urease.

Amongst the polypeptides encoded by the accessory genes of the urease gene cluster is the gene product of Ure I (SEQ ID NO:42), as illustrated in FIG. 9, which also forms part of the invention. Also included is a variant of the Ure I product having at least 75% homology, preferably at least 85%, or a fragment of the gene product or of the variant having at least 6 amino acids. The variant preferably has the capacity to modulate the expression of urease activity. The urease activity can be detected by using the following test: $10^9$ bacteria containing the Ure I gene product variant are suspended in 1 ml of urea-indole medium and incubated at 37° C. The hydrolysis of the urea leads to the release of ammonium, which increases pH and induces a color change from orange to fuscia-red.

It is also possible that a fragment of the Ure I gene product (SEQ ID NO:42), if it has a length of, for example, at least 70 or 100 amino acids, may also exhibit this functional homology with the entire polypeptide (SEQ ID NO:42).

The fragments of Ure I polypeptide or of the variant preferably are capable of inducing the formation of antibodies, which interfere with the activation process of the urease apoenyzme.

The invention also relates to the proteinaceous material comprising at least one of the heat shock proteins or chaperonins of *Helicobacter pylori* or a fragment thereof. Particularly preferred are the HspA and HspB polypeptides as illustrated in FIG. 6 or a polypeptide having at least 75%, and preferably at least 80 or 90%, homology or identity with the said polypeptide. A particularly preferred fragment of the *Helicobacter pylori* HspA polypeptide is the C-terminal sequence SEQ ID NO:1 or a sub-fragment of this sequence having at least 6 consecutive amino acids. This C-terminal sequence is thought to act as a metal binding domain allowing binding of, for example, nickel or divalent cations.

*E. coli* strains containing various subsets of the *H. pylori* urease subunits:

- *E. coli* MC1061 (pILL918) [CNCM registration number I-1336] expressing a UreA peptide (AA N°19 to AA N°238) fused to MalE
- *E. coli* MC1061 (pILL923) [CNCM registration number I-1338] expressing a UreA peptide (AA N°58 to AA N°238) fused to MalE
- *E. coli* MC1061 (pILL924) [CNCM registration number I-1339] expressing a UreA peptide (AA N°184 to AA N°238) fused to MalE
- *E. coli* MC1061 (pILL928) [CNCM registration number I-1341] expressing a UreA peptide (AA N°205 to AA N°569) fused to MalE
- *E. coli* MC1061 (pILL931) [CNCM registration number I-1342] expressing a UreA peptide (AA N°400 to AA N°569) fused to MalE HspA and HspB of *H. felis* are detected as shown in FIG. 20. Antibodies raised against MBP HspA or MBP HspB of *H. pylori* recognized HspA and HspB of *H. felis*.

The proteinaceous material of the invention may also comprise or consist of a fusion or mixed protein including at least one of the sub-units of the urease structural polypeptide of *H. pylori* and/or of *H. felis*, or fragments or variants thereof as defined above. Particularly preferred fusion proteins are the Mal-E fusion proteins and QIAexpress system fusion proteins (QIAGEN, USA) as detailed above. The fusion or mixed protein may include, either instead of or in addition to the urease sub-unit, a Heat Shock Protein, or fragment or variant thereof, as defined above.

The invention also relates to monoclonal or polyclonal antibodies to the proteinaceous materials described above. More particularly, the invention relates to antibodies or fragments thereof to any one of the *Helicobacter felis* polypeptides encoded by the urease gene cluster of the plasmid pILL205 (CNCM I-1355), including the structural and accessory urease polypeptides, that is, structural genes UreA (SEQ ID NO:20) and UreB (SEQ ID NO:21) and the accessory genes known as Ure E, Ure F, Ure G, Ure H and Ure I. The antibodies may also be directed to a polypeptide having at least 90% homology with any of the above urease polypeptides or to a fragment thereof preferably having at least 6 amino acids. The antibodies of the invention may specifically recognize *Helicobacter felis* polypeptides expressed by the urease gene cluster. In this case, the epitopes recognized by the antibodies are unique to *Helicobacter felis*. Alternatively, the antibodies may include or consist of antibodies directed to epitopes common to *Helicobacter felis* urease polypeptides and to *Helicobacter pylori* urease polypeptides. If the antibodies recognize the accessory gene products, it is particularly advantageous that they cross-react with the *Helicobacter pylori* accessory gene product. In this way, the antibodies may be used in therapeutic treatment of *Helicobacter pylori* infection in man by blocking the urease maturation process.

Particularly preferred antibodies of the invention recognize the *Helicobacter felis* UreA (SEQ ID NO:20) and/or UreB (SEQ ID NO:21) gene products, that is the A and B urease sub-units. Advantageously, these antibodies also cross-react with the *Helicobacter pylori* A (SEQ ID NO:22) and B (SEQ ID NO:26) urease sub-units, but do not cross-react with other ureolytic bacteria. Such antibodies may be prepared against epitopes unique to Helicobacter (see FIG. 4), or alternatively, against the whole polypeptides followed by screening out of any antibodies reacting with other ureolytic bacteria.

The invention also concerns monoclonal or polyclonal antibodies to the Hsps or fragments thereof, particularly to the HspA (SEQ ID NO:29) and/or HspB (SEQ ID NO:30) protein illustrated in FIG. 6. Polypeptides having at least 75%, and preferably at least 80%, or 90%, homology with the Hsps may also be used to induce antibody formation. These antibodies may be specific for the *Helicobacter pylori* or *H. felis* chaperonins or, alternatively, they may cross-react with GroEL-like proteins or GroES-like proteins from bacteria other than Helicobacter, depending upon the epitopes recognized. FIG. 7 shows the homologous regions of HspA (SEQ ID NO:29) and HspB (SEQ ID NO:30) with GroES-like proteins (SEQ ID NOS:31–35) and GroEL-like proteins (SEQ ID NOS:31–35), respectively, from various bacteria. Particularly preferred antibodies are those specific for either the HspA or HspB chaperonins or those specifically recognizing the HspA C-terminal sequence having the metal binding function. Again, use of specific fragments for the induction of the antibodies ensures production of Helicobacter-specific antibodies.

The antibodies of the invention may be prepared using classical techniques. For example, monoclonal antibodies may be produced by the hybridoma technique, or by known techniques for the preparation of human antibodies, or by the technique described by Marks et al. (Journal of Molecular Biology, 1991, 222, p. 581–597).

The invention also includes fragments of any of the above antibodies produced by enzyme digestion. Of particular interest are the Fab and $F(ab')_2$ fragments. Also of interest are the Facb fragments.

The invention also relates to purified antibodies or serum obtained by immunization of an animal, e.g., a mammal, with the immunogenic composition, the proteinaceous material or fragment, or the fusion or mixed protein(s) of the invention, followed by purification of the antibodies or serum. Such protein can be the product of one of the genes of urease cluster either *H. pylori* or *H. felis* associated or not with the product of HspA or HspB of *H. pylori* or *H. felis* genes. Also concerned is a reagent for the in vitro detection of *H. pylori* infection containing at least these antibodies or serum, optionally with reagents for labelling the antibodies, e.g., anti-antibodies etc.

The invention further relates to nucleic acid sequences coding for any of the above proteinaceous materials including peptides. In particular, the invention relates to a nucleic acid sequence characterized in that it comprises:

i) a sequence coding for the *Helicobacter felis* and/or *H. pylori* urease and/or accessory polypeptides as defined above, and/or a sequence coding for the Hsp of *H. pylori* or *H. felis* as defined above; or ii) a sequence complementary to sequence (i); or iii) a sequence capable of hybridizing to sequence (i) or (ii) under stringent conditions; or iv) a fragment of any of sequences (i), (ii) or (iii) comprising at least 10 nucleotides.

Preferred nucleic acid sequences are those comprising all or part of the sequence of plasmid pILL205 (CNCM I-1355), for example the sequence (SEQ ID NO:19) of FIG. 3, in particular that coding for the gene product of UreA (SEQ ID NO:20) and for Urea (SEQ ID NO:21) or the sequence of FIG. 9 (Ure I) (SEQ ID NO:41), or a sequence capable of hybridizing with these sequences under stringent conditions, or a sequence complementary to these sequences, or a fragment comprising at least 10 consecutive nucleotides of these sequences.

Other preferred sequences are those comprising all or part of the sequence of plasmid pILL689 (CNCM I-1356), for example the sequence of FIG. 6, in particular that coding for HspA (SEQ ID NO:29) and/or HSpB (SEQ ID NO:30), or a sequence complementary to this sequence, or a sequence capable of hybridizing to this sequence under stringent conditions, or a fragment thereof.

High stringency hybridization conditions in the context of the invention are the following:

5×SSC;

50% formamide at 37° C.;

or:

6×SSC;

Denhard medium at 68° C.

The sequences of the invention also include those hybridizing to any of sequences (i), (ii) and (iii) defined above under non-stringent conditions, that is:

5×SSC;

0.1% SDS;

30 or 40% formamide at 42° C., preferably 30%.

The term "complementary sequences" in the context of the invention signifies "complementary" and "reverse" or "inverse" sequences.

The nucleic acid sequences may be DNA or RNA.

The sequences of the invention may be used as nucleotide probes in association with appropriate labelling means. Such means include radioactive isotopes, enzymes, chemical or chemico-luminescent markers, fluorochromes, haptens, or antibodies. The markers may optionally be fixed to a solid support, for example a membrane or particles.

As a preferred marker, radioactive phosphorous ($^{32}P$) is incorporated at the 5'-end of the probe sequence. The probes of the invention comprise any fragment of the described nucleic acid sequences and may have a length for example of at least 45 nucleotides, for example 60, 80 or 100 nucleotides or more. Preferred probes are those derived from the UreA, UreB, Ure I, HspA and HspB genes.

The probes of the invention may be used in the in vitro detection of Helicobacter infection in a biological sample, optionally after a gene amplification reaction. Most advantageously, the probes are used to detect *Helicobacter felis* or *Helicobacter pylori*, or both, depending on whether the sequence chosen as the probe is specific to one or the other, or whether it can hybridize to both. Generally, the hybridization conditions are stringent in carrying out such a detection.

The invention also relates to a kit for the in vitro detection of Helicobacter infection, characterized in that it comprises:

a nucleotide probe according to the invention, as defined above;

an appropriate medium for carrying out a hybridization reaction between the nucleic acid of Helicobacter and the probe; and reagents for the detection of any hybrids formed.

The nucleotide sequences of the invention may also serve as primers in a nucleic acid amplification reaction. The primers normally comprise at least 10 consecutive nucleotides of the sequences described above and preferably at least 18. Typical lengths are from 25 to 30 and may be as high as 100 or more consecutive nucleotides. Such primers are used in pairs and are chosen to hybridize with the 5'- and 3'-ends of the fragment to be amplified. Such an amplification reaction may be performed using for example the PCR technique (European patent applications EP200363, 201184 and 229701). The Q-β-replicase technique (*Biotechnology*, vol. 6, October 1988) may also be used in the amplification reaction.

The invention also relates to expression vectors characterized in that they contain any of the nucleic acid sequences of the invention. Particularly preferred expression vectors are plasmids pILL689 and pILL205 (CNCM I-1356 and CNCM I-1355, respectively). The expression vectors will normally contain suitable promoters, terminators and marker genes, and any other regulatory signals necessary for efficient expression.

The invention further relates to prokaryotic or eukaryotic host cells stably transformed by the nucleic acid sequences of the invention. As examples of hosts, mention may be made of higher eukaryotes such as CHO cells and cell-lines; yeast; prokaryotes including bacteria such as *E. coli*, e.g, *E. coli* HB 101, Shigellae or Salmonella, *Mycobacterium tuberculosis*, viruses including baculovirus and vaccinia. Usually the host cells will be transformed by vectors. However, it is also possible within the context of the invention to insert the nucleic acid sequences by homologous recombination, using conventional techniques. For example, WO 90.11354 (Brulet et al.) describes the technology to carry out an homologous recombination in eukaryotic cells.

By culturing the stably transformed hosts of the invention, the Helicobacter urease polypeptide material and, where applicable, the Hsp material can be produced by recombinant means. The recombinant proteinaceous materials are then collected and purified. Pharmaceutical compositions are prepared by combining the recombinant materials with suitable excipients, adjuvants, and optionally, any other additives, such as stabilizers.

The invention also relates to plasmids pILL920 (deposited at CNCM on 20.07.1993, under accession number I-1337) and pILL927 (CNCM I-1340, deposited on 20.07.1993) constructed as described in the examples below.

The invention covers also the DNA (or RNA derived from such DNA) purified from the expression vectors and used as immunogen capable of inducing an immune response in a host (cellular or antibody response).

EXAMPLES

I. CLONING, EXPRESS AND SEQUENCING OF *H. FELIS* UREASE GENE

A. EXPERIMENTAL PROCEDURES FOR PART I

1. Bacterial strains and culture conditions:

*H. felis* (ATCC 49179) was grown on blood agar base no. 2 (Oxoid) supplemented with 5% (v/v) lysed horse blood (BioMerieux) and an antibiotic supplement consisting of 10 ng $ml^{-1}$ vancomycin (Lederle Laboratories), 2.5 $\mu$g $ml^{-1}$ polymyxin B (Pfizer), 5 $\mu$g $ml^{-1}$ trimethoprim (Sigma Chemical Co.) and 2.5 $\mu$g $ml^{-1}$ amphotericin B (E. R Squibb and Sons, Inc.). Bacteria were cultured on freshly prepared agar plates and incubated, lid uppermost, under microaerobic conditions at 37° C. for 2–3 days. *E. coli* strains HB101 (Boyer and Roulland-Dussoix, 1969) and MC1061 (Maniatis et al., 1983), used in the cloning experiments, were grown routinely in Luria broth without glucose added or on Luria agar medium, at 37° C. Bacteria grown under nitrogen-limiting solid medium consisting of ammonium-free M9 minimal medium (pH 7.4) supplemented with 0.4% (w/v) D-glucose and 10 mM L-arginine (Cussac et al., 1992).

2. DNA manipulations:

All standard DNA manipulations and analyses, unless mentioned otherwise, were performed according to the procedures described by Maniatis et al. (1983).

3. Isolation of *H. felis* DNA:

Total genomic DNA was extracted by an sarkosyl-proteinase K lysis procedure (Labigne-Roussel et al., 1988). Twelve blood agar plates inoculated with *H. felis* were incubated in an anaerobic jar (BBL) with an anaerobic gaspak (BBL 70304) without catalyst, for 1–2 days at 37° C. The plates were harvested in 50 ml of a 15% (v/v) glycerol –9% (w/v) sucrose solution and centrifuged at 5,000 rpm (in a Sorvall centrifuge), for 30 min at 4° C. The pellet was resuspended in 0.2 ml 50 mM D-glucose in 25 mM Tris-10 mM EDTA (pH 8.0) containing 5 mg $ml^{-1}$ lysozyme and transferred to a VTi65 polyallomer quick seal tube. A 0.2 ml aliquot of 20 mg $ml^{-1}$ proteinase K and 0.02 ml of 5M sodium perchlorate were added to the suspension. Cells were lysed by adding 0.65 ml of 0.5M EDTA –10% (w/v) Sarkosyl, and incubated at 65° C. until the suspension cleared (approximately 5 min). The volume of the tube was completed with a CsCl solution consisting (per 100 ml) of 126 g CsCl, 1 ml aprotinine, 99 ml TES buffer (30 mM Tris, 5 mM EDTA, 50 mM NaCl (pH 7.5). Lysates were centrifuged at 45,000 rpm, for 15–18 h at 180° C. Total DNA was collected and dialyzed against TE buffer (10 mM Tris, 1 mM EDTA), at 4° C.

4. Cosmid cloning:

Chromosomal DNA from *H. felis* was cloned into cosmid vector pILL575, as previously described (Labigne et al., 1991). Briefly, DNA fragments arising from a partial digestion with Sau3A were sized on a (10 to 40% ) sucrose density gradient and then ligated into a BamHI-digested and dephosphorylated pILL575 DNA preparation. Cosmids were packaged into phage lambda particles (Amersham, In Vitro packaging kit) and used to infect *E. coli* HB101. To screen for urease expression, kanamycin-resistant transductants were replica-plated onto solid nitrogen-mimiting medium (see above) containing (20 $\mu$g $ml^{-1}$) kanamycin that had been dispensed into individual wells of microtitre plates (Becton Dickinson). The microtiter plates were incubated aerobically at 37° C. for 2 days before adding 0.1 ml urease reagent (Hazell et al., 1987) to each of the wells. Ureolysis was detected within 5–6 h, at 37° C. by a color change in the reagent. Several urease-positive cosmid clones were restriction mapped and one was selected for subcloning.

5. Subcloning of *H. felis* DNA:

A large-scale CsCl plasmid preparation of cosmid DNA was partially digested Sau3A. DNA fragments (7–11 kb) were electroeluted from an agarose gel and purified using phenol-chloroform extractions. Following precipitation in cold ethanol, the fragments were ligated into Bg/III-digested plasmid pILL570 (Labigne et al., 1991) and the recombinant plasmids used to transform competent *E. coli* MC1061 cells. Spectinomycin-resistant transformants were selected and screened for urease expression under nitrogen-rich (Luria agar) and nitrogen-limiting conditions.

6. Quantitative urease activity:

Cultures grown aerobically for 2.5 days at 37° C. were harvested and washed twice in 0.85% (w/v) NaCl. Pellets were resuspended in PEB buffer (0.1M sodium phosphate buffer (pH 7.4) containing 0.01M EDTA) and then sonicated by four 30-sec bursts using a Branson Sonifier Model 450 set at 30 W, 50% cycle. Cell debris was removed from the sonicates by centrifugation. Urease activities of the sonicates were measured in a 0.05M urea solution prepared in PEB by a modification of the Berthelot reaction (Cussac et al., 1992). Urease activity was expressed as $\mu$mol urea $min^{-1}mg^{-1}$ bacterial protein.

7. Protein determination:

Protein concentrations were estimated with a commercial version of the Bradford assay (Sigma Chemicals).

8. Transposon mutagenesis:

Random insertional mutations were generated within cloned *H. felis* via a MiniTn3-Km delivery system (Labigne et al., 1992). In brief, *E. coli* HB101 cells containing the transposase-encoding plasmid pTCA were transformed with plasmid pILL570 containing cloned *H. felis* DNA. Transposition of the MiniTn3-Km element into the pILL570 derivative plasmids was effected via conjugation. The resulting cointegrates were then selected for resolved structures in the presence of high concentrations of kanamycin (500 mg1-1) and spectinomycin (300 mg $1^{-1}$).

9. SDS-PAGE and Western Blotting:

Solubilized cell extracts were analyzed on slab gels, comprising a 4.5% acrylamide stacking gel and 12.5% resolving gel, according to the procedure of Laemmli (Laemmli, 1970). Electrophoresis was performed at 200V on a mini-slab gel apparatus (Bio-Rad).

Proteins were transferred to nitrocellulose paper (Towbin et al., 1979) in a Mini Trans-Blot transfer cell (Bio-Rad) set at 100 V for 1 h (with cooling). Nitrocellulose membranes were blocked with 5% (w/v) purified casein (BDH) in phosphate-buffered saline (PBS, pH 7.4) at room temperature, for 2 h (Ferrero et al., 1992). Membranes were reacted at 4° C. overnight with antisera diluted in 1% (w/v) casein prepared in PBS. Immunoreactants were then detected using a biotinylated secondary antibody (Kirkegaard and Perry Lab.) in combination with avidin-peroxidase (KPL). A substrate solution composed of 0.3% (w/v) 4-chloro-1-naphthol (Bio-Rad) was used to visualize reaction products.

10. DNA Sequencing:

DNA fragments to be sequenced were cloned into M13mp18 and M13mp19 (Meissing and Vieira, 1982) bacteriophage vectors (Pharmacia). Competent *E. coli* JM101 cells were transfected with recombinant phage DNA and plated on media containing X-gal (5-bromo-4-chloro-3-indolyl-β-D-galactopyranoside) and isopropyl-β-D-thiogalactopyranoside. Plaques arising from bacteria infected with recombinant phage DNA were selected for the preparation of single-stranded DNA templates by polyethylene glycol treatment (Sanger et al., 1977). Single-stranded DNA sequenced according to the dideoxynucleotide chain termination method using a Sequenase kit (United States Biochemical Corp.).

11. Nucleotide sequence accession number:

The nucleotide accession number is X69080 (EMBL Data Library).

B. RESULTS OF PART I EXPERIMENTS

1. Expression of urease activity by *H. felis* cosmid clones:

Cloning of partially digested fragments (30 to 45 kb in size) of *H. felis* chromosomal DNA into the cosmid vector pILL575 resulted in the isolation of approximately 700 cosmid clones. The clones were subcultured on nitrogen-limiting medium in order to induce urease expression (Cussac et al., 1992). Six of these were identified as being urease-positive after 5–6 h incubation (as described in the Experimental procedures section). No other urease-positive cosmid clones were identified, even after a further overnight incubation. Restriction enzyme analysis of 3 clones harboring the urease-encoding cosmids revealed a common 28 kd DNA fragment. A cosmid (designated pILL199) containing DNA regions at both extremities of the common fragment was selected for subcloning.

2. Identification of *H. felis* genes required for urease expression when cloned in *E. coli* cells:

To define the minimum DNA region necessary for urease expression in *E. coli* cells, the urease-encoding cosmid pILL199 was partially digested with Sau3A and the fragments were subcloned into plasmid pILL570. The transformants were subcultured on nitrogen-rich and nitrogen-limiting media and screened for an urease-positive phenotype. Five transformants expressed urease activity when grown under nitrogen-limiting conditions, whereas no activity was detected following growth on nitrogen-rich medium. Restriction mapping analyses indicated that the urease-encoding plasmids contained inserts of between 7 and 11 kb. The plasmid designated pILL205 was chosen for further studies.

Figure 1:
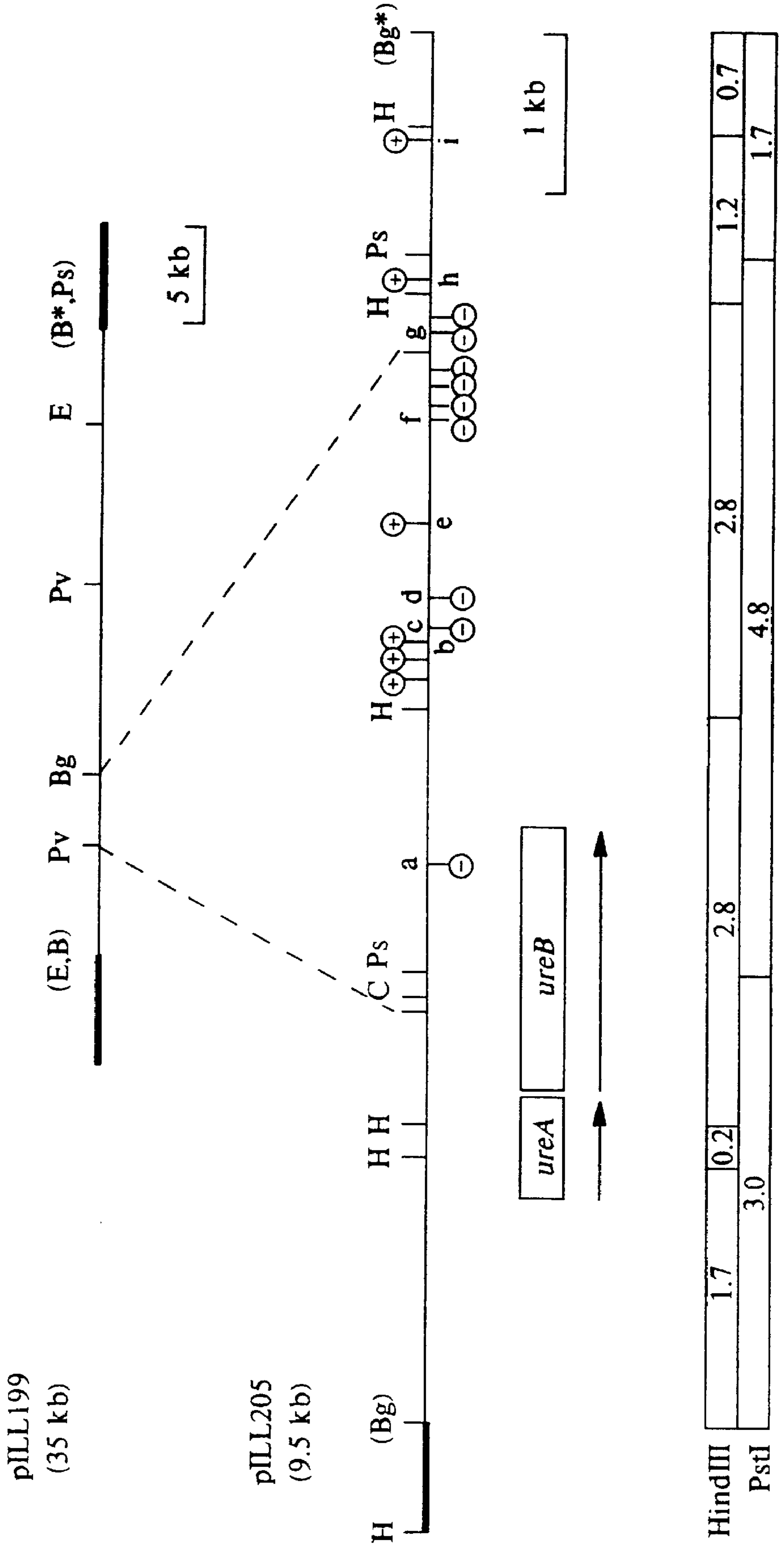
FIG. 1. Transposon mutagenesis and sequencing of pILL205. Linear restriction maps of recombinant cosmid pILL199 and recombinant plasmid pILL205 (and the respective scale markers) are presented. Numbers in parentheses indicate the sizes of *H. felis* DNA fragments inserted into one of the cloning vectors (pILL575 described in J. Bact. 1991, 173:1920–1931 or pILL570, described in Res. Microb. 1992, 143:1526, respectively). The "plus" and "minus" signs within circles correspond to the insertion sites of the MiniTn3-Km transposon in pILL205; "plus" signs indicate that the transposon did not inactivate urease expression, whereas negative signs indicate that urease expression was abolished. The letters refer to mutant clones, which were further characterized for quantitative urease activity and for the synthesis of urease gene products. The location of the structural urease genes (UreA and UreB) on pILL205 are represented by boxes, the lengths of which are proportional to the sizes of the respective open-reading frames. The arrows refer to the orientation of transcription. The scale at the bottom of the Figure indicates the sizes (in kilobases) of the HindIII and PstI restriction fragments. Restriction sites are represented as follows: B, BamHI; Pv, PvuII; Bg, BglII; E, EcoRI; H, HindIII; C, ClaI; Ps, PstI. Letters within parentheses indicate that the sites originated from the cloning vector.

Random mutagenesis of cloned *H. felis* DNA was performed to investigate putative regions essential for urease expression in *E. coli* and to localize the region of cloned DNA that contained the structural urease genes. Random insertion mutants of the prototype plasmid pILL205 were thus generated using the MiniTn3-Km element (Labigne et al., 1992). The site of insertion was restriction mapped for each of the mutated copies of pILL205 and cells harboring these plasmids were assessed qualitatively for urease activity (FIG. 1). A selection of *E. coli* HB101 cells harboring the mutated derivatives of pILL205 (designated "a" to "i") were then used both for quantitative urease activity determinations, as well as for the detection of the putative urease subunits by Western blotting.

The urease activity of *E. coli* HB101 cells harboring pILL205 was 1.2±0.5 $\mu$mol urea $min^{-1}mg^{-1}$ bacterial protein (Table 1), which is approximately a fifth that of the parent *H. felis* strain used for the cloning. Insertion of the transposon at sites "a", "c", "d", "f" and "g" resulted in a negative phenotype, whilst mutations at sites "b", "e", "h" and "i" had no significant effect on the urease activities of clones harboring these mutated copies of pILL205 (Table 1). Thus mutagenesis of pILL205 with the MiniTn3-Km element identified three domains as being required for *H. felis* urease gene expression in *E. coli* cells.

Figure 2A:
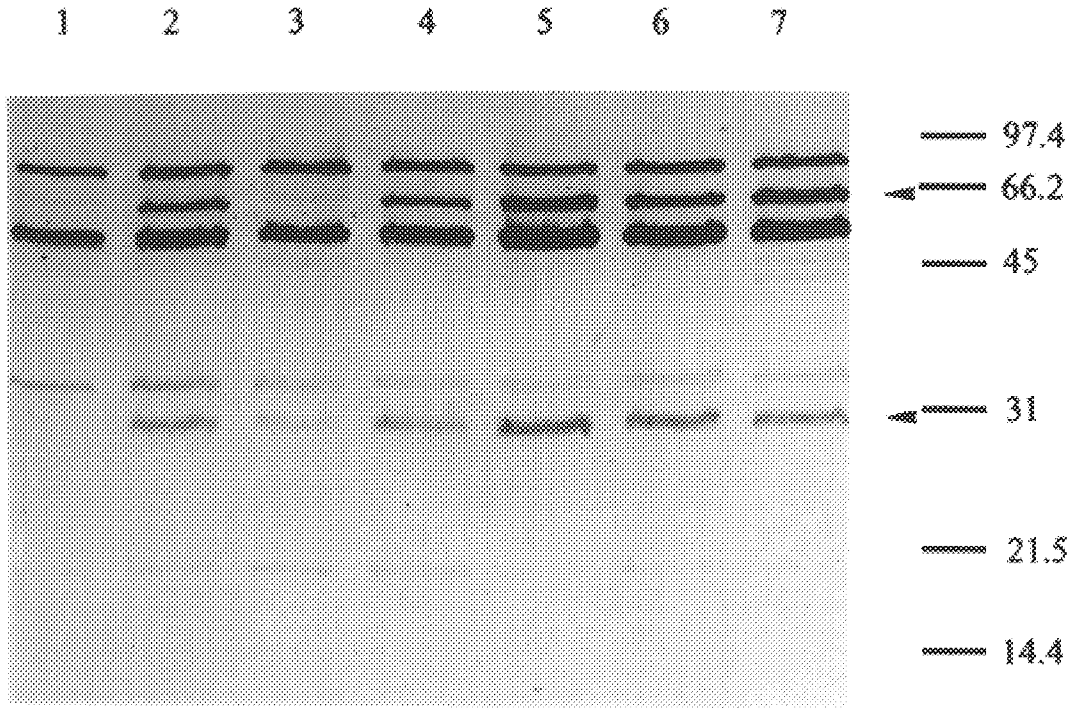
FIG. 2. Western blot analysis of whole-cell extracts of *E. coli* HB101 cells harboring recombinant plasmids were reacted with rabbit polyclonal antiserum (diluted 1:1, 1000) raised against *H. felis* bacteria.
Figure 2B:
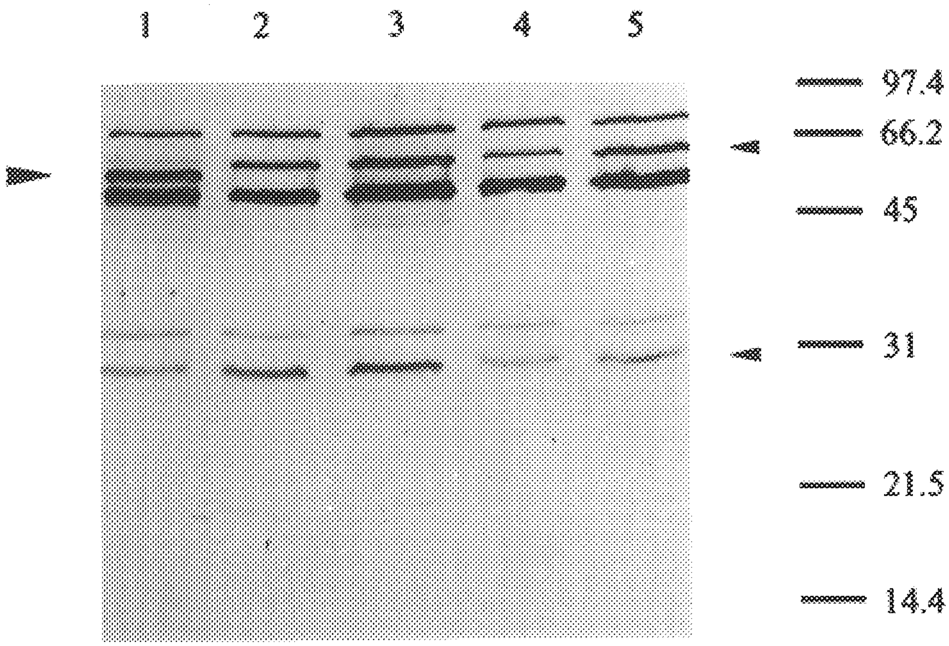

3. Localization of the *H. felis* urease structural genes:

Western blot analysis of extracts of *E. coli* cells harboring pILL205 indicated the presence of two polypeptides of approximately 30 and 66 kDa, which cross-reacted with polyclonal *H. felis* rabbit antiserum (FIG. 2A). These proteins were not produced by bacteria carrying the vector (pILL570). Native *H. felis* urease has been reported to be composed of repeating monomeric subunits with calculated molecular weights of 30 and 69 kDa (Turbett et al., 1992). Thus, the 30 and 66 kDa proteins were thought to correspond to the UreA (SEQ ID NO:20) and UreB (SEQ ID NO:21) gene products, respectively. Interestingly an extract of *E. coli* cells harboring the recombinant plasmid pILL763 (Cussac et al., 1992) containing the *Helicobacter pylori* UreA (SEQ ID NO:22) and UreB (SEQ ID NO:26) genes, expressed two polypeptides with approximate molecular sizes of 30 and 62 kDa, which cross-reacted with the anti-*H. felis* antisera (FIG. 2B).

TABLE 1

Mutagensis of *E. coli* clones and effect on urease activity.

| plasmids[a] | Urease activity[b] ($\mu$mol urea $min^{-1}$ $mg^{-1}$ protein) |
|---|---|
| pILL205 | 1.2 ± 0.46[c] |
| pILL205 :: a | neg[d] |
| pILL205 :: b | 0.74 ± 0.32 |
| pILL205 :: c | neg |
| pILL205 :: d | neg |
| pILL205 :: e | 0.54 ± 0.15 |
| pILL205 :: f | neg |
| pILL205 :: g | neg |
| pILL205 :: h | 1.05 ± 0.25 |
| pILL205 :: i | 0.93 ± 0.35 |

[a]*E. coli* cells harbored pILL205 and its derivatives constructed by transposon mutagenesis. The letters correspond to the insertion sites of the MiniTn3-transposon on pILL205.
[b]Activities of bacteria grown aerobically for 3 days at 37° C. on solid M9 minimal medium supplemented with 10 mM L-arginine. The values represent the means ± standard deviations calculated from three determinations.
[c]Urease activity was approximately a fifth as large as that of *H. felis* wild-type strain (ATCC 49179), i.e. 5.7 ± 0.1 $\mu$mol urea $min^{-1}$ protein (Ferrero and Lee, 1991).
[d]No activity detected (limit of detection was <1 nmol urea $min^{-1}$ $mg^{-1}$ of bacterial protein).

Clones harboring the mutated derivatives of pILL205, in all but one case, expressed the UreA and UreB gene products (FIGS. 2A, B). Given that several of the mutants (i.e., mutants “c”, “d”, “f” and “g”) synthesized the urease subunits yet did not produce an active enzyme, it is possible to speculate that accessory functions essential for urease activity may have been disrupted by transposon insertion. In contrast, the mutant designated pILL205::a did not produce the UreB product and was urease-negative. Thus, the site of transposon insertion was presumed to be located in the UreB gene. Sequence analyses of the DNA region corresponding to insertion site “a” were undertaken to elucidate potential open reading frames encoding the structural polypeptides of *H. felis* urease.

4. Sequence analyses of *H. felis* structural urease genes:

Sequencing of a 2.4 kb region of *H. felis DNA adjacent to transposon insertion site “a” resulted in the identification of two open reading frames (ORFs) designated UreA (SEQ ID NO:*20) and UreB (SEQ ID NO:21), which are transcribed in the same direction (FIG. 3). The transposon was confirmed to be located at 240 bp upstream from the end of UreB (SEQ ID NO:21). Both ORFs commenced with an ATG start codon and were preceded by a site similar to the *E. coli* consensus ribozome-binding sequence (Shine and Dalgarno, 1974). The intergenic space for the *H. felis* structural genes consisted of three codons, which were in phase with the adjacent open reading frames. This suggests that, as has already been observed to be the case for *Helicobacter pylori* (Labigne et al., 1991), a single mutation in the stop codon of the ure A gene would theoretically result in a fused single polypeptide.

The *H. felis* UreA (SEQ ID NO:20) and UreB (SEQ. ID NO:21) genes encode polypeptides with calculated molecular weights of 26,074 Da and 61,663 Da, respectively, which are highly homologous at the amino acid sequence level to the UreA (SEQ ID NO:22) and UreB (SEQ ID NO:26) gene products of *H. pylori*. The levels of identity between the corresponding ure A and ure B gene products of the two Helicobacter spp. was calculated to be 73.5% and 88.2%, respectively. From the amino acid sequence information, the predicted molecular weights of the UreA (SEQ ID NOS:20, 22) and UreB (SEQ ID NOS:21,26) polypeptides from *H. felis* and *H. pylori* (Labigne et al., 1991) are very similar. Nevertheless the UreB (SEQ ID NO:21) product of *H. felis* had a lower mobility than the corresponding gene product from *Helicobacter pylori* when subjected to SDS-polyacrylamide gel electrophoresis (FIG. 2B)

II. EXPRESSION OF RECOMBINANT UREASE SUBUNIT PROTEINS FROM *H. PYLORI* AND *H. FELIS*: ASSESSMENT OF THESE PROTEINS AS POTENTIAL MUCOSAL IMMUNOGENS IN A MOUSE MODEL

The aims of the study were to develop recombinant antigens derived from the urease subunits of *H. pylori* and *H. felis*, and to assess the immunoprotective efficacies of these antigens in the *H. felis*/mouse model. Each of the structural genes encoding the respective urease subunits from *H. pylori* and *H. felis* was independently cloned and over-expressed in *Escherichia coli*. The resulting recombinant urease antigens (which were fused to a 42 kDa maltose-binding protein of *E. coli*) were purified in large quantities from *E. coli* cultures and were immunogenic, yet enzymatically inactive. The findings demonstrated the feasibility of developing a recombinant vaccine against *H. pylori* infection.

A. EXPERIMENTAL PROCEDURES FOR PART II

1. Bacterial strains, plasmids and growth conditions:

*H. felis* (ATCC 49179) was grown on a blood agar medium containing blood agar base no. 2 (Oxoid) supplemented with 10% lysed horse blood (BioMerieux) and an antibiotic supplement consisting of vancomycin (10 $\mu$g/mL), polymyxin B (25 ng/mL), trimethoprim (5 $\mu$g/mL) and amphotericin B (25 $\mu$g/mL). Bacteria were cultured under microaerobic conditions at 37° C. for 2 days, as described previously. *E. coli* strains MC1061 and JM101, used in cloning and expression experiments, were grown routinely at 37° C. in Luria medium, with or without agar added. The antibiotics carbenicillin (100 $\mu$g/mL) and spectinomycin (100 $\mu$g/mL) were added as required.

2. DNA manipulations and analysis:

All DNA manipulations and analyses, unless mentioned otherwise, were performed according to standard procedures. Restriction and modification enzymes were purchased from Amersham (France). DNA fragments to be cloned were electroeluted from agarose gels and then purified by passage on Elutip mini-columns (Schleicher and Schull, Germany). Single-stranded DNA sequencing was performed using M13mp18 and M13mp19 bacteriophage vectors (Pharmacia, France). Single-stranded DNA templates were prepared from recombinant phage DNA by polyethylene glycol treatment. Sequencing of the templates was achieved according to the dideoxynucleotide chain termination method using a Sequenase kit (United States Biochemical Corp., U.S.A.).

3. Preparation of inserts for cloning using the polymerase chain reaction (PCR):

To clone the UreA genes of *H. pylori* (SEQ ID NO:22) and *H. felis* (SEQ ID NO:20), degenerate 36-mer primers were conceived from the published urease sequences (Labigne et al., 1991; Ferrero and Labigne, 1993) (primer set #1 (SEQ ID NOS:2–3); refer to Table 2). Purified DNA from *E. coli* clones harboring plasmids pILL763 and pILL207 (Table 3), that encoded the structural genes of *H. pylori* and *H. felis* ureases, were used as template material in PCR reactions. Reaction samples contained: 10–50 ng of denatured DNA; PCR buffer (50 mmol/L KCl in 10 mmol/L Tris-HCl [pH 8.3)]); dATP, dGTP, dCTP and dTTP (each at a final concentration of 1.25 mmol/L); 2.5 mmol/L $MgCl_2$; 25 pmol of each primer and 0.5 μL Taq polymerase. The samples were subjected to 30 cycles of the following program: 2 min at 94° C., 1 min at 40° C.

The amplification products were cloned into the cohesive ends of the pAMP vector (FIG. 1) according to the protocol described by the manufacturer ("CloneAmp System", Gibco BRL; Cergy Pontoise, France). Briefly, 60 ng of amplification product was directly mixed in a buffer (consisting of 50 mmol/L KCl, 1.5 mmol/L $MgCl_2$, 0.1% (wt/vol) gelatine in 10 mmol/L Tris-HCl, pH 8.3) with 50 ng of the pAMP 1 vector DNA and 1 unit of uracil DNA glycolsylase. Ligation was performed for 30 min at 37° C. Competent cells (200 μL) of *E. coli* MC1061 were transformed with 20 μL of the ligation mixture. Inserts were subsequently excised from the polylinker of the pAMP vector by double digestion with BamHI and Pst1, and then subcloned into the expression vector pMAL (New England Biolabs Inc., Beverly, USA) chosen for the production of recombinant antigens (pILL919 and pILL920, respectively, FIG. 13), as well as in M13mp bacteriophage for sequencing.

Amplification of a product containing the UreB gene of *H. pylori* (SEQ ID NO:26) was obtained by PCR using a couple of 35-mer primers (set #2 (SEQ ID NOS:4–5), Table 2). The PCR reaction mixtures were first denatured for 3 min at 94° C., then subjected to 30 cycles of the following program: 1 min at 94° C., 1 min at 55° C., and 2 min at 72° C. The purified amplification product (1850 bp was digested with EcoRI and PstI and then cloned into pMAL (pILL927, FIG. 2). Competent cells of *E. coli* MC1061 were transformed with the ligation reaction.

*H. felis* UreB (SEQ ID NO:21) was cloned in a two-step procedure that allowed the production of both complete and truncated versions of the UreB subunit. Plasmid pILL213 (Table 3) was digested with the enzymes DraI, corresponding to amino acid residue number 219 of the UreB subunit and HindIII. The resulting 1350 bp fragment was purified and cloned into pMAL that had been digested with XmnI and HindIII (pILL219, FIG. 2). In order to produce a clone capable of synthesizing a complete UreB protein, PCR primers were developed (set #3 (SEQ ID NOS:6–7), Table 2) that amplified a 685 bp fragment from the N-terminal portion of the ureB gene (excluding the ATG codon), that also overlapped the beginning of the insert in plasmid pILL219. The PCR amplified material was purified and digested with bamHI and HindIII, and then cloned into PMAL (pILL221, FIG. 14). A 1350 bp PstI-PstI fragment encoding the remaining portion of the UreB gene product was subsequently excised from pILL219 and cloned into a linearized preparation of pILL221 (pILL222, FIG. 14).

4. Expression of recombinant urease polypeptides in the vector pMAL:

The expression vector pMAL is under the control of an inducible promoter ($P_{lac}$) and contains an open-reading frame (ORF) that encodes the production of MalE (Maltose-binding protein, MBP). Sequences cloned in-phase with the latter ORF resulted in the synthesis of MBP-fused proteins, which were easily purified on amylose resin. of the two versions of PMAL that are commercially available, the version not encoding a signal sequence (i.e., pMAL-c2) synthesized greater amounts of recombinant proteins and was thus used throughout.

*E. coli* clones harboring recombinant plasmids were screened for the production of fusion proteins prior to performing large-scale purification experiments.

5. Purification of recombinant urease polypeptides:

Fresh 500 mL volumes of Luria broth containing carbenicillin (100 μg/mL and 2% (wt/vol) glucose were inoculated with overnight cultures (5 mL) of *E. coli* clones. The cultures were incubated at 37° C. and shaken at 250 rpm, until the $A_{600}$=0.5. Prior to adding 1 mmol/L (final concentration) isopropyl-β-D-thiogalactopyranoside (IPTG) to cultures, a 1.0 mL sample was taken (non-induced cells). Cultures were incubated for a further 4 h at which time another 1.0 mL sample (induced cells) was taken. The non-induced and induced cell samples were later analyzed by SDS-PAGE.

IPTG-induced cultures were centrifuged at 7000 rpm for 20 min at 4° C. and the supernatant discarded. Pellets were resuspended in 50 mL column buffer (200 mmol/L NaCl, 1 mmol/L EDTA in 10 mmol/L Tris HCl,pH 7.4), containing the following protease inhibitors (supplied by Boehringer, Mannheim, Germany): 2 μmol/L leupeptin, 2 μmol/L pepstatin, and 1 mmol/L phenylmethylsulphonyl fluoride (PMSF). Intact cells were lysed by passage through a French Pressure cell (16,000 lb/in$^2$). Cell debris was removed by centrifugation and lysates were diluted in column buffer to give a final concentration of 2.5 mg protein/mL, prior to chromatography on a 2.6 cm×20 cm column of amylose resin (New England Biolabs). The resin was washed with column buffer at 0.5 mL/min until the $A_{280}$ returned levels. The MBP-fused recombinant proteins were eluted from the column by washing with column buffer containing 10 mmol/L ρ-maltose.

Fractions containing the recombinant proteins were pooled and then dialyzed several times at 4° C. against a low salt buffer (containing 25 mmol/L NaCl in 20 mmol/L TrisHCl, pH 8.0). The pooled fractions were then loaded at a flow rate of 0.5 mL/min onto a 1.6×10 cm anion exchange column (HP-Sepharose, Pharmacia, Sweden) connected to a Hi-Load chromatography system (Pharmacia). Proteins were eluted from the column using a salt gradient (25 mmol/L to 500 mmol/L NaCl). Fractions giving high absorbance readings at $A_{280}$ were exhaustively dialyzed against distilled water at 4° C. and analyzed by SDS-PAGE.

6. Rabbit antisera:

Polyclonal rabbit antisera was prepared against total cell extracts of *H. pylori* strain 85P (Labigne et al., 1991) and *H. felis* (ATCC 49179). Polyclonal rabbit antisera against recombinant protein preparations of *H. pylori* and *H. felis* urease subunits was produced by immunizing rabbits with 100 μg of purified recombinant protein in Freund's complete adjuvant (Sigma). Four weeks later, rabbits were booster-immunized with 100 μg protein in Freund's incomplete adjuvant. On week 6, the animals were terminally bled and the sera kept at −20° C.

7. Protein analyzes by SDS-PAGE and Western blotting:

Solubilized cell extracts were analyzed an slab gels comprising a 4.5% acrylamide stacking gel and a 10% resolving gel, according to the procedure of Laemmli. Electrophoresis was performed at 200 V on a mini-slab gel apparatus (Bio-Rad, USA).

Proteins were transferred to nitrocellulose paper in a Mini Trans-Blot transfer cell (Bio-Rad) set at 100 V for 1 h, with cooling. Nitrocellulose membranes were blocked with 5% (wt/vol) casein (BDH, England) in phosphate-buffered saline (PBS, pH 7.4) with gentle shaking at room temperature for 2 h. Membranes were reacted at 4° C. overnight with antisera diluted in 1 casein prepared in PBS. Immunoreactants were detected using specific biotinylated secondary antibodies and streptavidin-peroxidase conjugate (Kirkegaard and Parry Lab., Gaithersburg, USA). Reaction products were visualized on autoradiographic film (Hyperfilm, Amersham, France) using a chemiluminescence technique (ECL system, Amersham).

Protein concentrations were determined by the Bradford assay (Sigma Chemicals corp., St Louis, USA).

8. Animal experimentation:

Six week old female Swiss Specific Pathogen-Free (SPF) mice were obtained (Centre d'Elevage R. Janvier, Le-Genest-St.-Isle, France) and maintained on a commercial pellet diet with water ad libitum. The intestines of the animals were screened for the absence of *Helicobacter muridarum*. For all orogastric administrations, 100 $\mu$L aliquots were delivered to mice using 1.0 mL disposable syringes to which polyethylene catheters (Biotrol, Paris, France) were attached.

9. Preparation of sonicated extracts and inocula from *H. felis* cultures:

*H. felis* bacteria were harvested in PBS and centrifuged at 5000 rpm, for 10 min in a Sorvall RC-5 centrifuge (Sorvall, USA) at 4° C. The pellets were washed twice and resuspended in PBS. Bacterial suspensions were sonicated as previously described and were subjected to at least one freeze-thaw cycle. Protein determinations were carried out on the sonicates.

To ensure a virulent culture of *H. felis* for protection studies, *H. felis* bacteria were maintained in vivo until required. Briefly, mice were inoculated three times (with $10^{10}$ bacteria/mL), over a period of 5 days. The bacteria were reisolated from stomach biopsies on blood agar medium (4–7 days' incubation in a microaerobic atmosphere at 37° C.). Bacteria grown for two days on blood agar plates were harvested directly in peptone water (Difco, USA). Bacterial viability and motility were assessed by phase microscopy prior to administration to animals.

10. Mouse protection studies:

Fifty $\mu$g of recombinant antigen and 10 $\mu$g cholera holotoxin (Sigma Chemical Corp.), both resuspended in $HCO_3$, were administrated orogastrically to mice on weeks 0, 1, 2 and 3. Mice immunized with sonicated *H. felis* extracts (containing 400–800 $\mu$g of total protein) were also given 10 $\mu$g of cholera toxin. On week 5, half of the mice from each group were challenged with an inoculum of virulent *H. felis*. The remainder of the mice received an additional "boost" immunization on week 15. On week 17 the latter were challenged with a culture of *H. felis*.

11. Assessment of *H. felis* colonization of the mouse:

Two weeks after receiving the challenge dose (i.e., weeks 7 and 19, respectively) mice were sacrificed by spinal dislocation. The stomachs were washed twice in sterile 0.8% NaCl and a portion of the gastric antrum from each stomach was placed on the surfaces of 12 cm×12 cm agar plates containing a urea indicator medium (2% urea, 120 mg $Na_2HPO_4$, 80 mg $KH_2PO_4$, 1.2 mg phenol red, 1.5 g agar prepared in 100 mL). The remainder of each stomach was placed in formal-saline and stored until processed for histology. Longitudinal sections (4 $\mu$m) of the stomachs were cut and routinely stained by the Giemsa technique. When necessary, sections were additionally stained by the Haematoxylin-Eosin and Warthin-Starry silver stain techniques.

The presence of *H. felis* bacteria in mouse gastric mucosa was assessed by the detection of urease activity (for up to 24 h) on the indicator medium, as well as by the screening of Giemsa-stained gastric sections that had been coded so as to eliminate observer bias. The numbers of bacteria in gastric sections were semi-quantitatively scored according to the following scheme: 0, no bacteria seen throughout sections; 1, few bacteria (<20) seen throughout; 2, occasional high power (H.P.) field with low numbers (<20) of bacteria; 3, occasional H.P. field with low to moderate numbers (<50) of bacteria; and 4, numerous (>5) H.P. fields with high numbers of bacteria (>50). Mononuclear cell infiltrates were scored as follows: 0, no significant infiltration; 1, infiltration of low numbers of mononuclear cells limited to the submucosa and muscularis mucosa; 2, infiltration of moderate numbers of mononuclear cells to the submucosa and muscularis mucosa, sometimes forming loose aggregates; and 3, infiltration of large numbers of mononuclear cells and featuring nodular agglomerations of cells.

B. RESULTS OF PART II EXPERIMENTS

1. Expression of Helicobacter urease polypeptides in *E. coli:*

Fragments containing the sequences encoding the respective UreA gene products of *H. felis* (SEQ ID NO:20) and *H. pylori* (SEQ ID NO:22) were amplified by PCR and cloned in-phase with an ORF encoding the 42 kDa MBP, present on the expression vector pMAL. Sequencing of the PCR products revealed minor nucleotide changes that did not, however, alter the deduced amino acid sequences of the respective gene products. *E. coli* MC1061 cells transformed with these recombinant plasmids (pILL919 and pILL920, respectively) expressed fusion proteins with predicted molecular weights of approximately 68 kDa. Following chromatography on affinity (amylose resin) and anion exchange gel media (Q-Sepharose), these proteins were purified to high degrees of purity (FIG. 1). The yield from 2-L cultures of recombinant *E. coli* cells was approximately 40 mg of purified antigen.

Similarly, the large UreB subunits of *H. pylori* (SEQ ID NO:26) and *H. felis* (SEQ ID NO:21) ureases were expressed in *E. coli* (plasmids pILL927 and pILL222, respectively) and produced fusion proteins with predicted molecular weights of 103 kDa. The yield in these cases was appreciably lower than for the UreA preparations (approximately 20 mg was recovered from 2-L of bacterial culture). Moreover, problems associated with the cleavage of the UreB polypeptides from the MBP portion of the fusion proteins were encountered. These difficulties were attributed to the large sizes of the recombinant UreB polypeptides.

2. Analysis of the recombinant urease polypeptides:

Western blot analyses of the antigen preparations with rabbit polyclonal antisera raised to whole-extracts of *H. pylori* and *H. felis* bacteria demonstrated that the antigens retained immunogenicity to the homologous as well as heterologous antisera (FIGS. 14 and 15). The antisera did not recognize the MBP component alone. Cross-reactivity between the urease polypeptides of *H. pylori* and *H. felis* was consistent with the high degrees of identity between the amino acid sequences of these proteins.

Rabbit polyclonal antisera raised against purified recombinant UreA (SEQ ID NOS:20,22) and UreB (SEQ ID NOS:21,26) proteins prepared from *H. pylori* and *H. felis* strongly reacted with the urease polypeptides present in whole-cell extracts of the bacteria (FIG. 16). As we had already observed, the UreB subunit of *H. felis* (SEQ ID NO:21) urease migrated slightly higher on SDS-PAGE gels than did that of *H. pylori* (SEQ ID NO:26) (FIG. 16).

3. Preparation of *H. felis* inocula used in immunoprotection studies:

To ensure the virulence of *H. felis* bacterial inocula, bacteria were reisolated from *H. felis*-infected mouse stomachs (see Materials and Methods). The bacteria were passaged a minimum number of times in vitro. Stock cultures prepared from these bacteria, and stored at −80° C., were used to prepare fresh inocula for other mouse protection studies. This procedure ensured that the inocula used in successive experiments were reproducible.

Immunization of mice against gastric *H. felis* infection

Mice that had been immunized for three weeks with the given antigen preparations were divided into two lots and one half of these were challenged two weeks later with an *H. felis* inoculum containing $10^7$ bacteria/mL. One group of animals that had been immunized with recombinant *H. felis* UreA (SEQ ID NO: 20) were also challenged but, unlike the other animals, were not sacrificed until week 19.

a) Protection at week 5:

Eighty-five % of stomach biopsy samples from the control group of mice immunized with *H. felis* sonicate preparations were urease-negative and therefore appeared to have been protected from *H. felis* infection (Table 4). This compared to 20% of those from the other control group of animals given MBP alone. The proportion of urease-negative stomachs for those groups of mice given the recombinant urease subunits varied from 70% (for *H. pylori* UreB (SEQ ID NO:26)) to 20% (for *H. pylori* UreA (SEQ ID NO:22)).

The levels of bacterial colonization by *H. felis* was also assessed from coded histological slides prepared from gastric tissue. Due to the striking helical morphology of *H. felis* bacteria, the organisms could be readily seen on the mucosal surfaces of both gastric pit and glandular regions of the stomach. Histological evidence indicated that the levels of protection in mice was lower than that observed by the biopsy urease test: 25% and 20% of gastric tissue from mice immunized with *H. felis* sonicate preparations of *H. pylori* UreB (SEQ ID NO:26), respectively, were free of *H. felis* bacteria.

Amongst certain groups of these mice the preponderance of urease-negative biopsies, as well as lower histological scores for bacterial colonization (unpublished data), suggested that an immunoprotective response had been elicited in the animals. This response, however, may have been insufficient to protect against the inoculum administered during the challenge procedure.

b) Protection at week 17:

The remaining mice, from each group of animals, were boosted on week 15. These mice were challenged at week 17 with an *H. felis* inoculum containing approximately 100-fold less bacteria than that used previously. Two weeks later all stomach biopsies from the MBP-immunized mice were urease-positive (Table 4). In contrast, urease activity for gastric biopsies from mice immunized with the recombinant urease subunits varied from 50% for *H. pylori* UreA (SEQ ID NO:22) to 100% for *H. felis* UreB (SEQ ID NO:21). The latter was comparable to the level of protection observed for the group of animals immunized with *H. felis* sonicated extracts. Histological evidence demonstrated that the UreB subunits of *H. felis* (SEQ ID NO:21) and *H. pylori* (SEQ ID NO:26) protected 60% and 25% of immunized animals, respectively. This compared with a level of 85% protection for mice immunized with *H. felis* sonicated extracts. Immunization of mice with recombinant *H. pylori* UreA (SEQ ID NO:22) did not protect the animals. Similarly, the stomachs of all *H. felis* UreA (SEQ ID NO:20)-immunized mice, that had been challenged at week 5, were heavily colonized with *H. felis* bacteria at week 19 (Table 4).

The urease gastric biopsy test, when compared to histological analysis of gastric tissue sections, gave sensitivity and specificity values of 63% and 95%, respectively. Thus, histology proved to be the more accurate predictor of *H. felis* infection in the mouse.

5. Cellular immune response in immunized stomachs:

In addition to the histological assessment of *H. felis* colonization, mouse gastric tissue was also scored (from 0 to 3) for the presence of a mononuclear cell response. In mice immunized with MBP alone, a mild chronic gastritis was seen with small numbers of mononuclear cells restricted to the muscularis mucosa and to the submucosa of the gastric epithelium. In contrast, there were considerable numbers of monouclear cells present in the gastric mucosae from animals immunized with either the recombinant urease polypeptides, or with *H. felis* sonicate preparations. These inflammatory cells coalesced to form either loose aggregates, in the submucosal regions of the tissue, or nodular structures that extended into the mucosal regions of the gastric epithelia. The mononuclear cell response did not appear to be related to the presence of bacteria as the gastric mucosae from the *H. felis* UreA (SEQ ID NO:20)-immunized mice, that were heavily colonized with *H. felis* bacteria, contained little or no mononuclear cells.

TABLE 2

The oligomeric primers used in PCR-based amplification of urease-encoding nucleotide sequences.

| Primer set | | Nucleotide sequence (5' ->3') |
|---|---|---|
| #1 | forw | . . . CAU CCT* AAA$^{G}$ GAA$^{G}$ T$^{C}$TA* GAT$^{C}$ AAA$^{G}$ T$^{C}$TA* ATG (SEQ ID NO:2) |
| | rev | T$^{C}$TC C$^{T}$TT A*CG A*CG A*G$^{C}$A$^{T}$ A$^{G,T}$AT C$^{T}$TT C$^{T}$TT CAT CUA (SEQ ID NO:3) . . . |
| #2 | forw | CC GGA GAA TTC ATT AGC AGA AAA GAA TAT GTT TCT ATG (SEQ ID NO:4) *Eco*RI¥ |
| | rev | AC GTT CTG CAG CTT ACG AAT AAC TTT TGT TGC TTG AGC (SEQ ID NO:5) *Pst*I¥ |
| #3 | forw | GGA TCC AAA AAG ATT TCA CG (SEQ ID NO:6) *Bam*HI¥ |

TABLE 2-continued

The oligomeric primers used in PCR-based amplification of urease-encoding nucleotide sequences.

| Primer set | Nucleotide sequence (5' ->3') |
|---|---|
| rev | GGA AGC TT C TGC AGG TGT GCT TCC CCA GTC (SEQ ID NO:7)<br>*Hind*III[¥] *Pst*I[¥] |

*Degenerated nucleotides in which all possible permutations of the genetic code were included (A, T, G, C).
G,C,T The given nucleotides were degenerate with the specific base(s) shown.
[¥]Restriction sites introduced in the amplified fragments.

TABLE 3

Plasmids used.

| Plasmid Reference | Vector | Relevant phenotype or character | |
|---|---|---|---|
| pILL763 | pILL570 | 9.5 kb fragment (Sau3a partial digest of *H. pylori* chromosome) ($Sp^R$) | Cussac et al., 1991 |
| pILL199 | pILL575 | 35 kb fragment (Sau3A partial digest of *H. felis* chromosome) | Ferrero & Labigne, '93 |
| pIll207 | pILL570 | 11 kb fragment (Sau3A partial digest of pILL199) | Infection & Immunity 1994, 62: 4981–4989 |
| pILL919 | pMAL-C2 | 0.8 kb BamHI-PstI[a] insert containing a nucleotide fragment encoding *H. felis* (SEQ ID NO:19) ureA gene ($Ap^R$) | Infection & Immunity 1994, 62: 4981–4989 |
| pILL920 | pMAL-C2 | 0.8 kb BamHI-PstI[a] insert containing PCR product encoding *H. pylori* ureA gene | Infection & Immunity 1994, 62: 4981–4989 |
| pILL927 | pMAL-C2 | 1.8 kb EcoRI-PstI[a] PCR fragment encoding *H. pylori* ureB gene | Infection & Immunity 1994, 62: 4981–4989 |
| pILL213 | pUC19 | 2 kb fragment resulting from Sau3A partial digest of pILL207 ($Ap^R$) | Infection & Immunity 1994, 62: 4981–4989 |
| pILL219 | pMAL-C2 | 1.4 kb DraI-HindIII[b] insert containing *H. felis ureB* (SEQ ID NO:19) (bases 657–1707) | Infection & Immunity 1994, 62: 4981–4989 |
| pILL221 | pMAL-C2 | 0.7 kb BamHI-PstI PCR fragment encoding *H. felis* ureB (SEQ ID NO:19) (bases 4–667) | Infection & Immunity 1994, 62: 4981–4989 |
| pILL222 | pMAL-C2 | 1.35 kb PstI-PstI[c] fragment encoding *H. felis* ureB (SEQ ID NO:19) from (bases 667–1707) pILL219 cloned into linerized pILL221 | Infection & Immunity 1994, 62: 4981–4989 |

TABLE 4

Protection of mice by immunization with recombinant urease proteins.

| Antigen | Protection (%)[a] | | | |
|---|---|---|---|---|
| | Urease | | Histology | |
| MBP | 0% | (0/10) | 0% | (0/10) |
| UreA *H. pylori* (SEQ ID NO:22) | 50 | (4/8) | 0 | (0/10) |
| UreA *H. felis*[b] (SEQ ID NO:20) | 12.5 | (1/8) | 0 | (0/10) |

TABLE 4-continued

Protection of mice by immunization with recombinant urease proteins.

| Antigen | Protection (%)[a] | | | |
|---|---|---|---|---|
| | Urease | | Histology | |
| UreB *H. pylori* (SEQ ID NO:26) | 65 | (5/8) | 25 | (2/8) |

TABLE 4-continued

| Protection of mice by immunization with recombinant urease proteins. | | | | |
|---|---|---|---|---|
| | Protection (%)[a] | | | |
| Antigen | Urease | | Histology | |
| UreB *H. felis* (SEQ ID NO: 21) | 100 | (7/7) | 60 | (5/7) |
| *H. felis sonicate* | 100 | (8/8) | 85 | (7/8) |

[a]Challenge inoculum dose was $10^5$ bacteria/mouse
[b]Mice were challenged on week 5 (with $10^7$ bacteria) and were sacrificed on week 19.

III. HELICOBACTER PYLORI HspAB HEAT SHOCK GENE CLUSTER: NUCLEOTIDE SEQUENCE, EXPRESSION AND FUNCTION:

A homolog of the heat shock proteins (Hsps) of the GroEL class, reported to be closely associated with the urease of *Helicobacter pylori* (a nickel metalloenzyme), has recently been purified from *H. pylori* cells by Dunn et al., and Evans et al. (Infect. Immun. 60:1946, 1992, 1946 and 2125, respectively). Based on the reported N-terminal amino acid sequence of this immunodominant protein, degenerate oligonucleotides were synthesized in order to target the gene (hspB) (SEQ ID NO:28) encoding the GroEL-like protein in the chromosome of *H. pylori* strain 85P. Following gene amplification, a 108-base pair (bp)-fragment encoding the 36 first amino acids of the hspB protein (SEQ ID NO:30) was purified, and used a probe to identify in the *H. pylori* genomic bank a recombinant cosmid harboring the entire hspB encoding gene (SEQ ID NO:28). The hspB gene (SEQ ID NO:28) was mapped to a 3.15 kilobases (kb) BglII restriction fragment of the pILL684 cosmid (Table 5). The nucleotide sequence of that fragment subcloned into the pILL570 plasmid (pILL689) revealed the presence of two open reading frames (OFRs) designated hspA and hspB, the organization of which was very similar to be groESL bicistronic operons of other bacterial species. hspA and hspB (SEQ ID NO:28) encode polypeptides of 118 and 545 amino acids, respectively, corresponding to calculated molecular masses of 13.0 and 58.2 kilodaltons (kDa), respectively. Amino acid sequence comparison studies revealed i) that the *H. pylori* HspA (SEQ ID NO:29) and HspB (SEQ ID NO:30) protein were highly similar to their bacterial homologs; ii) that the HspA (SEQ ID NO:29) *H. pylori* protein features a striking motif at the carboxyl terminus that other bacterial GroEs-homologs lack; this unique motif consists of a series of eight histidine residues resembling metal binding domain, such a nickel binding. Surprisingly, immediately upstream of the gene cluster an IS5 insertion element was found that was absent in the *H. pylori* genome, and was positively selected during the cosmid cloning process. The IS5 was found to be involved in the expression of the hspA and hspB genes in pILL689. The expression of the HspA (SEQ ID NO:29) and HspB (SEQ ID NO:30) proteins from the pILL689 plasmid was analyzed in minicell-producing strain. Both polypeptides were shown to be constitutively expressed in the *E. coli* cells. When the pILL689 recombinant plasmid was introduced together with the *H. pylori* urease gene cluster into an *E. coli* host strain, an increase of urease activity was observed suggesting a close interaction between the heat shock proteins and the urease enzyme. Supporting the concept of a specific function for the HspA chaperone, was the fact that whereas a single hspB copy was found in the *H. pylori* genome, two copies of the hspA were found in the genome, one linked to the hspB gene and one unlinked to the hspB gene. Attempts to construct isogenic mutants of *H. pylori* in the HspA and the hspB gene were unsuccessful suggesting that these genes are essential for the survival of the bacteria.

A. EXPERIMENTAL PROCEDURES FOR PART III

1. Bacterial strains, plasmids, and culture conditions:

The cloning experiments were performed with genomic DNA prepared from *H. pylori* strain 85P. *H. pylori* strain N6 deposited at NCIMB No. 40512 on Jun. 26, 1992 was used as the recipient strain for the electroporation experiments because of its favorable transformability. *E. coli* strain HB101 or strain MC1061 were used as a host for cosmid cloning and subcloning experiments, respectively. *E. coli* P678-54 was used for preparation of minicells. Vectors and recombinant plasmids used in this study are listed in Table 1. *H. pylori* strains were grown on horse blood agar plates, supplemented with vancomycin (10 mg/l), polymyxin B (2,500 U/l), trimethoprim (5 mg/l), and amphotericin B (4 mg/l ). Plates were incubated at 37° C. under microaerobic conditions in an anaerobic jar with a carbon dioxide generator envelope (BBL 70304). *E. coli* strains were grown in L-broth without glucose (10 g of tryptone, 5 g of yeast extract, and 5 g of NaCl per liter; pH 7.0) or on L-agar plates (1.5% agar) at 37° C. For measurement of urease activity, the nitrogen-limiting medium used consisted of ammonium-free M9 minimal agar medium (pH 7.4) containing 0.4% D-glucose as the carbon source, and freshly prepared filter-sterilized L-arginine added to the final concentration of 10 mM. Antibiotic concentrations for the selection of recombinant clones were as follows (in milligrams per liter): kanamycin, 20; spectinomycin, 100; carbenicillin, 100.

2. Preparation of DNA:

Genomic DNA from *H. pylori* was prepared as previously described. Cosmid and plasmid DNAs were prepared by an alkaline lysis procedure followed by purification in cesium chloride-ethidium bromide gradients as previously described.

3. Cosmid cloning:

The construction of the cosmid gene bank of *H. pylori* 85P in *E. coli* HB101, which was used for the cloning of the *H. pylori* HspA-B (SEQ ID NO:28) gene cluster, has been described previously. Labigne et al., 1991, J. Bact. 173:1920.

4. DNA analysis and cloning methodology:

Restriction endonucleases, T4 DNA ligase, DNA polymerase I large (Klenow) fragment, and Taq polymerase were purchased from Amersham, T4 DNA polymerase from Biolabs, and calf intestinal phosphatase from Pharmacia. All enzymes were used according to the instructions of the manufacturers. DNA fragments were separated on agarose gels run in Tris-acetate buffer. The 1-kb ladder from Bethesda Research Laboratories was used as a fragment size standard. When necessary, DNA fragments were isolated by electroelution from agarose gels as previously described and recovered from the migration buffer by means of an Elutip-d minicolumn (Schleicher and Schuell, Dassel, Germany). Basic DNA manipulations were performed according to the protocols described by Sambrook et al.

5. Hybridization:

Colony blots for screening of the *H. pylori* cosmid bank and for identification of subclones were prepared on nitrocellulose membranes (Schleicher and Schuell, Dassel, Germany) according to the protocol of Sambrook et al. Radioactive labelling of PCR-products was performed by random priming using as primers the random hexamers from Pharmacia. Colony hybridizations were performed under high stringency conditions (5×SSC, 0.1% SDS, 50% formamide, 42° C.) (1×SSC; 150 mM NaCl, 15 mM sodium citrate, pH 7.0). For Southern blot hybridizations, DNA fragments were transferred from agarose gels to nitrocellulose sheets (0.45-μm pore size; Schleicher & Schuell, Inc.), and hybridized under low stringency conditions (5×SSC, 0.1% SDS, 30 or 40% formamide, at 42° C. with $^{32}$P-labeled deoxyribonucleotide probes.) Hybridization was revealed by autoradiography using Amersham Hyperfilm-MP.

6. DNA sequencing:

Appropriate fragments of plasmid DNA were subcloned into M13 mp 18/19 vectors. Single-stranded DNA was prepared by phage infection of *E. coli* strain JM101. Sequencing was performed by the dideoxynucleotide chain termination method using the United States Biochemicals Sequenase kit. Both the M13 universal primer and additional specific primers (FIG. 1) were used to sequence both the coding and non-coding DNA strands. Sequencing of double-stranded DNA was performed as previously described. Direct sequencing of PCR product was carried out following purification of the amplified, electroeluted PCR product through an Elutip-d minicolumn (Schleicher & Schuell). The classical protocol for sequencing using the Sequenase kit was then used with the following modifications: PCR product was denatured by boiling annealing mixture containing 200 picomoles of the oligonucleotide used as primer and DMSO to the final concentration of 1% for 3 minutes; the mixture was then immediately cooled on ice; the labeling step was performed in presence of manganese ions (mM).

7. Electroporation of *H. pylori:*

In the attempt to construct *H. pylori* mutants, appropriate plasmid constructions carrying the targeted gene disrupted by a cassette containing a kanamycin resistance gene (aph3'-III), were transformed into *H. pylori* strain N6 by means of electroporation as previously described. Plasmid pSUS10 harboring the kanamycin disrupted flaA gene was used as positive control of electroporation. After electroporation, bacteria were grown on non-selective plates for a period of 48 h in order to allow for the expression of the antibiotic resistance and then transferred onto kanamycin-containing plates. The selective plates were incubated for up to 6 days.

8. Polymerase chain reaction (PCR):

PCRs were carried out using a Perkin-Elmer Cetus thermal cycler using the GeneAmp kit (Perkin-Elmer Cetus). Classical amplification reaction involved 50 picomoles (pmoles) of each primer and at least 5 pmoles of the target DNA. The target DNA was heat denatured prior to addition to the amplification reaction. Reaction consisted of 25 cycles of the following three steps: denaturation (94° C. for 1 minute), annealing (at temperatures ranging between 42° and 55° C., depending on the calculated melting temperatures of the primers, for 2 min), and extension (72° C. for 2 min). When degenerate oligonucleotides were used in non-stringent conditions, up to 1000 pmoles of each oligonucleotide were added, 50 cycles were carried out, and annealing was performed at 42° C.

9. Analysis of proteins expressed in minicells:

Minicells harboring the appropriate hybrid plasmid were isolated and labeled with [$^{35}$S] methionine (50 μCi/ml). Approximately 100,000 cpm of acetone-precipitable material was subjected to sodium dodecyl sulfate (SDS)-polyacrylamide gel electrophoresis in a 12.5% gel. Standard proteins with molecular weights ranging from 94,000 to 14,000 (low<molecular-weights kit from Bio-Rad Laboratories) were run in parallel. The gel was stained and examined by fluorography, using En$^3$Hance (New England Nuclear).

10. Urease activity:

Urease activity was quantitated by the Berthelot reaction by using a modification of the procedure, which has already been described (Cussac et al., 1992, J. Bact. 176:2666–2673). Urease activity was expressed as micromoles of urea hydrolyzed per minute per milligram of bacterial protein.

B. RESULTS OF PART III EXPERIMENTS

1. Identification of a recombinant cosmid harboring the *Helicobacter pylori* GroEL-like heat shock protein encoding gene:

Based on the published N-terminal amino sequence of the purified heat shock protein of *H. pylori*, two degenerate oligonucleotides were synthesized to target the gene of interest in the chromosome of *H. pylori* strain 85P. The first one 5'-G C N A A R G A R A T H A A R T T Y T C N G (SEQ ID NO:8)-3', where N stands for the four nucleotides, R=A and G, Y=T and C, H=T, C, and A, is derived from the first 8 amino acids of the protein (AKEIKFSD)(SEQ ID NO:9); the second one 5'-C R T T N C K N C C N C K N G G N C C C A T (SEQ ID NO:10)-3', where K=G and T, corresponds to the complementary codons specifying the amino acid from position 29 to position 36 (MGPRGRNV (SEQ ID NO:11), Evans et al. 1992, Inf. Immun., 60:2125–2127). The expected size for the PCR product was 108 base pairs (bp). The amplification reaction was performed under low stringency conditions as described in the Materials and Methods section, and led to the synthesis of six fragments with sizes ranging from 400 bp to 100 bp. The three smallest fragments were electroeluted from an acrylamide gel and purified. Direct sequencing of the PCR products permitted the identification of a DNA fragment encoding an amino acid sequence corresponding to the published sequence. This fragment was, therefore, labeled and used as probe in colony hybridization to identify recombinant cosmids exhibiting homology to a 5' segment of the *H. pylori* GroEL-like encoding gene; this gene was further designated hspB. The gene bank consists of 400 independent kanamycin-resistant *E. coli* transductants harboring recombinant cosmids. Of those, one single clone hybridized with the probe and harbored a recombinant plasmid designated pILL684, 46 kb in size. The low frequency observed when detecting the hspB gene (1 of 400) was unusual when compared with that of several cloned genes, which were consistently detected in five to seven recombinant cosmids. In order to identify the hspB gene, fragments with sizes of 3 to 4 kb were generated by partial restriction of the pILL684 cosmid DNA with endonuclease Sau3A, purified, and ligated into the BglII site of plasmid vector pILL570. Of 100 subclones, 7 were positive clones, and one was further studied (pILL689) (Table 5); it contains a 3.15 kb insert, flanked by two BglII restriction sites, that was mapped in detail (FIG. 5). Using the PCR $^{32}$P labeled probe, the 5' end of the hspB gene was found to map to the 632 bp HindIII-SphI central restriction fragment of pILL689, indicating that one could expect the presence of the entire HspB gene in the pILL689 recombinant plasmid.

2. DNA sequence and deduced amino acid sequence of the *H. pylon* HspA-B gene cluster:

The 2300 bp of pILL689 depicted in FIG. 5 were sequenced by cloning into M13mp18 and M13mp19, the asymmetric restriction fragments BglII-SphI, SphI-HindIII, HindIII-BglII; each cloned fragment was independently sequenced on both strands, 16 oligonucleotide primers were synthesized to confirm the reading and/or to generate sequences overlapping the independently sequenced fragments; these were used as primers in double-stranded DNA sequencing analyses.

The analysis of the sequence revealed two distinct genetic elements. First the presence of two open reading frames (ORFs), depicted in FIG. 5, transcribed in the same direction, that were designated hspA (SEQ ID NO:29) and hspB (SEQ ID NO:30). The nucleotide sequence (SEQ ID NO:28) and the deduced amino acid sequence of the two ORFs are presented in FIG. 6. The first codon of hspA begins 323 bp upstream of the leftward HindIII site of pILL689 (FIG. 5) and is preceded by a Shine-Dalgarno ribosome-binding site (RBS) (GGAGAA). The hspA ORF codes for a polypeptide of 118 amino acids. The initiation codon for the hspB ORF begins 25 nucleotides downstream the hspA stop codon; it is preceded by a RBS site (AAGGA). The hspB ORF encodes a polypeptide of 545 amino acids and is terminated by a TAA codon followed by a palindromic sequence resembling a rho-independent transcription terminator (free energy, $\Delta G=-19.8$ kcal/mol) (FIG. 6). The N-terminal amino acid sequence of the deduced protein HspB was identical to the N-terminal sequence of the purified *H. pylori* heat shock protein previously published with the exception of the N-terminal methionine, which is absent from the purified protein and might be post-translationally removed, resulting in a mature protein of 544 amino acids.

The deduced amino acid sequences of *H. pylori* HspA (SEQ ID NO:29) and HspB (SEQ ID NO:30) were compared to several amino acid sequences of Hsps of the GroES and GroEL class (FIG. 7). HspB exhibited high homology at the amino acid level with the *Legionella pneumophila* HtpB protein (82.9% of similarities), with the *Escherichia coli* GroEL protein (81.0% of similarities), with the *Chlamydia psittaci* or *C. trachomatis* HypB protein (79.4% of similarities), with *Clostridium perfringens* Hsp60 protein (80.7% of similarities), and to a lesser extent to the GroEL-like proteins of Mycobacterium. However, like almost all the GroEL homologs, *H. pylori* HspB (SEQ ID NO:30) demonstrated the conserved carboxyl-terminus glycine-methionine motif (MGGMGGMGGMGGMM (SEQ ID NO:12)), which was recently shown to be dispensable in the *E. coli* GroEL chaperonin. The degree of homology at the amino acid level between the *H. pylori* HspA (SEQ ID NO:29) protein and the other GroES-like proteins (SEQ ID NOS:36–40) is shown in FIG. 7. The alignment shown features a striking motif at the carboxyl terminus of the *H. pylori* HspA (SEQ ID NO:29) protein that other bacterial GroES-homologs lack. This unique highly charged motif consists of 27 additional amino acids capable of forming a loop between two double cysteine residues; of the 27 amino acids, 8 are histidine residues highly reminiscent of a metal binding domain.

The second genetic element revealed by the sequence analysis, was the presence of an insertion sequence (IS5) 84 bp upstream of the hspA gene. The nucleotide sequence of this element matched perfectly that previously described for IS5 in *E. coli*, with the presence of a 16 nucleotide sequence (CTTGTTCGCACCTTCC (SEQ ID NO:13)) that corresponds to one of the two inverted repeats, which flank the IS5 element. Because of the perfect match at the DNA level, we suspected that the IS5 was not initially present in the *H. pylori* chromosome, but had rather inserted upstream of the HspA-HspB gene cluster during the cloning process, a hypothesis that needed to be confirmed by further analyses.

3. Identification of the upstream sequence of the HspA-B gene cluster in *H. pylori* chromosome:

The presence of the IS5 was examined by gene amplification using two oligonucleotides, one being internal to the IS5 element and the other one downstream of the IS5 element to target a putative sequence i) in the chromosome of *H. pylori* strain 85P, ii) in the initial cosmid pILL684 (Table 5), and iii) in the 100 subclones resulting from the Sau3A partial restriction of the pILL684 recombinant cosmid. IS5 was absent from the chromosome of *H. pylori*, and was present in the very first subcultures of the *E. coli* strain harboring cosmid pILL684. Among the 100 pILL684 subclone derivatives that appeared to contain all or part of the IS5 sequence, we then looked for a subclone harboring the left end side of the IS5 plus the original upstream sequence of the HspA-HspB gene cluster. This screening was made by restriction analysis of the different Sau3A partial generated subclones. The restriction map of one (pILL694) of the plasmids fulfilling these criteria is shown in Suerbaum et al., 1996, Molec. Microbiology. The left end side of the IS5 nucleotide sequence was determined; the presence of a 4-bp duplication CTAA on both sides of the 16-bp inverted repeats of the IS5 element allowed us to confirm the recent acquisition of the IS5 element by transposition. A 245-nucleotide sequence was then determined that mapped immediately upstream of the IS5 element. This sequence consists of a non-coding region in which the presence of a putative consensus heat shock promoter sequence was detected; it shows a perfectly conserved −35 region (TAACTCGCTTGAA (SEQ ID NO:14)) and a less consentaneous −10 region (CTCAATTA). Two oligonucleotides were synthesized, which mapped to sequences located on both sides of the IS5 element present in the recombinant cosmid; these two oligonucleotides should lead to the amplification of a 350 bp fragment when the IS5 sequence is present and a fragment in the absence of the IS5. The results of the PCR reaction using as target DNA the pILL684 cosmid, the pILL694 plasmid, and the *H. pylori* 85P chromosome fit the predictions (results not shown). Moreover, direct sequencing of the PCR product obtained from the *H. pylori* chromosome was performed and confirmed the upstream hspA-hspB reconstructed sequence. To further confirm the genetic organization of the whole sequenced region, two probes internal to the hspA and hspB genes, respectively, were prepared by gene amplification; they were used as probes in Southern hybridization experiments under low stringency conditions against an HindIII digest of the *H. pylori* 85P chromosome. The results demonstrate that no other detectable rearrangement had occurred during the cloning process (data not shown). These experiments allowed us to demonstrate that, whereas a single copy of the hspB gene was present in the chromosome of *H. pylori* strain 85, two copies of the hspA gene were detected by Southern hybridization.

4. Analysis of polypeptides expressed in minicells:

The pILL689 and the pILL692 recombinant plasmids and the respective cloning vectors pILL570, and pACYC177, were introduced by transformation into,*E. coli* P678-54, a minicell-producing strain. The pILL689 and pILL692 plasmids (Table 5) contain the same 3.15-kb insert cloned into the two vectors. pILL570 contains upstream of the polycloning site a stop of transcription and of translation; the orientation of the insert in pILL689 was made in such way that the transcriptional stop was located upstream of the IS5 fragment and therefore upstream of the HspA and HspB genes. Two polypeptides that migrated with polypeptides having apparent molecular weights of 60 kDa and 14 kDa were clearly detected in minicell-experiments from pILL689 and pILL692 (results not shown), whereas they were absent from the corresponding vectors; these results indicated that the hspA and hspB genes were constitutively expressed from a promoter located within the IS5 element. Moreover, whereas the amount of polypeptides visualized on the SDS gel was in good agreement with the copy number of the respective vectors, the intensity of the two polypeptidic bands suggested a polycistronic transcription of the two genes.

5. Attempts to understand the role of the HspA and HspB proteins:

complementations, the expression of the HspA (SEQ ID NO:29) and HspB (SEQ ID NO:30) proteins in the same *E. coli* cell allows to observe a three-fold increase in the urease activity following induction of the urease genes on minimum medium supplemented with 10 mM $L^{-1}$ arginine as limiting nitrogen source.

TABLE 5

Vectors and hybrid plasmids used in this study.

| Plasmid | Vector | Size(kb) | Characteristics(a) | Origin or Reference |
|---|---|---|---|---|
| | pILL575 | 10 | Mob, Cos, Km | — |
| | pILL570 | 5.3 | Mob, Sp | — |
| | pACYC177 | 3.9 | Ap, Km | — |
| pILL600 | pBR322 | 5.7 | Ap, Km, source of Km-cassette | — |
| pILL684 | pILL575 | 46 | Mob, Km, cosmid containing *H. pylori* hspA-B | Sau3A partial digest of *H. pylori* 85P DNA |
| pILL685 | pILL570 | 9.29 | Mob, Sp, plasmid containing *H. pylori* hspB | Sau3A partial digest of pILL684 |
| pILL686 | pUC19*c | 4.5 | Ap, plasmid containing *H. pylori* hspB | 1.9-kb BglII-cIaI pILL685 cloned into PUC19* |
| pILL687 | pUC19*(c) | 5.9 | Ap, Km, *H. pylori* hspB Ω Km-orientation A(b) | 1.4-kb SmaI-SmaI pILL600 cloned into pILL686 |
| pILL688 | pUC19*(c) | 5.9 | Ap, Km, *H. pylori* hspB Ω Km-orientation B(b) | 1.4-kb SmaI-SmaI pILL600 cloned into pILL686 |
| pILL689 | pILL570 | 8.45 | Mob, Sp, plasmid containing *H. pylori* hsp A-B | Sau3A partial digest of pILL684 |
| pILL691 | pUC19**(c) | 3.9 | Ap, plasmid containing *H. pylori* hspA 1.3-kb | SphI-SphI pILL689 cloned into pUC19** |
| pILL692 | pACYC177 | 7.05 | Ap, Km, plasmid containing *H. pylori* hspA-B | 3.15-kbBglII pILL689 cloned into pACYC177 |
| pILL694 | pILLS70 | 8.7 | Sp, plasmid containing left end of IS5 | Sau3A partial digest of pILL684 |
| pILL696 | pUC19**(c) | 5.3 | Ap, Km, *H. pylori* hspA Ω Km-orientation A (b) | 1.4-kb SmaI-SmaI pILL600 cloned into pILL691 |
| pSUS10 | pIC20R2 | 7.7 | Ap, Km, *H. pylori* flaA Ω Km | — |
| pILL753 | pILL570 | 16.5 | Sp, plasmid containing ureA, B, C, D, E, F, G, H, I | — |
| pILL763 | pILL570 | 14.75 | Sp, plasmid containing ureA, B, E, F, G, H, I- | — |

(a) Mob, conjugative plasmid due to the presence of OriT; Ap, Km and Sp, resistance to ampicillin, kanamycin, and spectinomycin, respectively; Cos, presence of lambda cos site.
(b) Orientation A indicates that the Kanamycin promoter initiates transcription in the same orientation as that of the of the gene where the cassette has been inserted; orientation B, the opposite.
(c) pUC19* and pUC19**: derivatives from pUC19 vector in which the SphI and HindIII site, respectively, have been end-filled by using the Klenow polymerase and self religated.

Two disruptions of genes were achieved in *E. coli* by inserting the Km cassette previously described within the hspA or the hspB gene of plasmids pILL686 and pILL691. This was done in order to return the disrupted genes in *H. pylori* by electroporation, and to select for allelic replacement. The pILL696 resulting plasmid encoded a truncated form of the HspA protein, corresponding to the deletion of the C-terminal end amino acid sequence, in that plasmid the Km cassette was inserted in such way that the promoter of the Km gene could serve as promoter for the HspB downstream gene. The pILL687 and pILL688 plasmids (Table 5) resulted from the insertion of the Km cassette in either orientation within the hspB gene. None of these constructs led to the isolation of kanamycin transformants of *H. pylori* strain N6, when purified pILL687, pILL688, pILL696 plasmids (Table 5) were used in electroporation experiments, whereas the pSUS10 plasmid used as positive control always did. These results suggest the *H. pylori* HspA and HspB protein are essential proteins for the survival of *H. pylori.*

Because of i) the constant description in the literature of a close association of the HspB protein with the urease subunits; ii) the unique structure of the HspA protein with the C-terminal sequence reminiscent of a nickel binding domain, and iii) of the absence of viable HspA and/or HspB mutants of *H. pylori*, we attempted to demonstrate a role of the *H. pylori* Hsp proteins in relation with the *H. pylori* urease by functional complementation experiments in *E. coli*. Plasmids pILL763 or pILL753 (both pILL570 derivatives, Table 5) encoding the urease gene cluster were introduced with the compatible pILL692 plasmid (pACYC177 derivative) that constitutively expresses the HspA (SEQ ID NO: 29) and HspB (SEQ ID NO:30) polypeptides as visualized in minicells. In both

IV. EXPRESSION, PURIFICATION AND IMMUNOGENIC PROPERTIES OF *H. PYLORI* HspA AND HspB

A. EXPERIMENTAL PROCEDURE FOR PART IV

1. Expression and purification of recombinant fusion proteins:

The MalE-HspA, and MalE-HspB fusion proteins were expressed following the cloning of the two genes within the pMAL-c2 vector as described in the "Results" section using the following primers:

oligo #1 ccgga gaattcAAGTTTCAACCATTAGGAGAAAGGGTC (SEQ ID NO:15)

oligo #2 acgtt ctgcagTTTAGTGTTTTTTGTGATCATGACAGC (SEQ ID NO:16)

oligo #3 ccgga gaattcGCAAAAGAAATCAAATTTTCAGATAGC (SEQ ID NO:17)

oligo #4 acgtt ctgcagATGATACCAAAAAGCAAGGGGGCTTAC (SEQ ID NO:18)

Two liters of Luria medium containing glucose (30%) and ampicillin (100 μmg/ml) were inoculated with 20 ml of an overnight culture of strain MC1061 containing the fusion plasmid and incubated with shaking at 37° C. When the OD600 of the culture reached 0.5, IPTG (at a final concentration of 10 mM) was added, and the cells were incubated for a further 4 hours. Cells were harvested by centrifugation (5000 rpm for 30 min at 4° C.), resuspended in 100 ml of column buffer consisting of 10 mM Tris-HCl, 200 mM NaCl, 1 mM EDTA supplemented with protease inhibitors [(Leupeptin (2 μM)-Pepstatin (2 μm)-PMSF (1 mM)-

Aprotinin (1:1000 dilution)], and passed through a French press. After centrifugation (10,000 rpm for 20 min at 4° C.), the supernatant were recovered and diluted (2-fold) with column buffer. The lysate was filtered through a 0.2 $\mu$m nitrocellulose filter prior to loading onto a pre-equilibrated amylose resin (22×2.5 cm). The fusion proteins were eluted with a 10 mM maltose solution prepared in column buffer, and the fractions containing the fusion proteins were pooled, dialyzed against distilled water, and lyophilized. Fusion proteins were resuspended in distilled water at a final concentration of 2 mg of lyophilized material/ml, and stored at −20° C. Concentration and purity of the preparations were controlled by the Bradford protein assay (Sigma Chemicals) and SDS-PAGE analyses.

2. Nickel binding properties of recombinant proteins:

*E. coli* MC1061 cells, containing either the pMAL-c2 vector or derivative recombinant plasmids, were grown in 100 ml-Luria broth in the presence of carbenicillin (100 $\mu$g/ml). The expression of the genes was induced with IPTG for four hours. The cells were centrifuged and the pellet was resuspended in 2 ml of Buffer A (6M guanidine hydrochloride, 0.1M $NaH_2PO_4$, 0.01 Tris, pH 8.0). After gentle stirring for one hour at room temperature, the suspensions were centrifuged at 10,000 g for 15 min at 4° C. A 1.6 ml aliquot of Nickel-Nitrilo-Tri-Acetic resin (Nickel-NTA, QIA Express), previously equilibrated in Buffer A, was added to the supernatant and this mixture was stirred at room temperature for one hour prior to loading onto a column. The column was washed with 20 ml buffer A, then 30 ml buffer B (8M urea, 0.1M Na-phosphate, 0.01M Tris-HCl, pH8.0). The proteins were eluted successively with the same buffer as buffer B adjusted to pH 6.3 (Buffer C), pH 5.9 (Buffer D) and pH 4.5 (Buffer E) and Buffer F (6M guanidine hydrochloride, 0.2M acetic acid). Fifty $\mu$l of each fraction were mixed with 50 $\mu$l of SDS buffer and loaded on SDS gels.

3. Human sera:

Serum samples were obtained from 40 individuals, 28 were *H. pylori*-infected patients as confirmed by a positive culture for *H. pylori* and histological examination of the biopsy, and 12 were uninfected patients. The sera were kindly provided by R. J. Adamek (University of Bochum, Germany).

4. Immunoblotting:

Upon completion of SDS-PAGE runs in a Mini-PROTEAN II electrophoresis cell, proteins were transferred to nitrocellulose paper in a Mini Trans-Blot transfer cell (Bio-Rad) set at 100 V for 1 h (with cooling). Immunostaining was performed as previously described (Ferrero et al., 1992), except that the ECL Western blotting detection system (Amersham) was used to visualize reaction products. Human sera and the rabbit antiserum, raised against a whole-cell extract of *H. pylori* strain 85P, were diluted 1:1000 and 1:5000, respectively, in 1% (w/v) casein prepared in phosphate-buffered saline (PBS, pH7.4).

5. Serological methods [enzyme-linked immunosorbent assay, (ELISA)]:

The following quantities of antigens were absorbed onto 96-well plates (Falcon 3072): 2.5 $\mu$g of protein MalE, 5 $\mu$g of MalE-HspA, or 2.5 of $\mu$g of MalE-HspB. The plates were left overnight at 4° C., then washed 3 times with ELISA wash solution (EWS) [1% PBS containing 0.05% (v/v) Tween 20]. Saturation was achieved by incubating the plates for 90 min at 37° C. in EWS supplemented with 1% milk powder. Wells were again washed 3 times with EWS and then gently agitated for 90 min at 37° C. in the presence of human sera (diluted 1:500 in EWS with 0.5% milk powder), under agitation. Bound immunoglobulins were detected by incubation for 90 min at 37° C. with biotinylated secondary antibody (goat anti-human IgG, IgA or IgM diluted [1:1000] in EWS supplemented with 0.5% milk powder) in combination with streptavidin-peroxidase (1:500) (Kirkegaard and Perry Lab.). Bound peroxidase was detected by reaction with the citrate substrate and hydrogen peroxide. Plates were incubated in the dark, at room temperature, and the optical density at 492 nm was read at intervals of 5, 15 and 30 min in an ELISA plate reader. After 30 min, the reaction was stopped by the addition of hydrochloric acid to a final concentration of 0.5M.

B. RESULTS OF PART IV EXPERIMENTS

1. Construction of recombinant plasmids producing inducible MalE-HspA, and HspB fusion proteins:

The oligonucleotides #1 and #2 (HspA) and #3 and #4 (HspB) were used to amplify by PCR the entire HspA and the HspB genes, respectively. The PCR products were electroeluted, purified and restricted with EcoRI and PstI. The restricted fragments (360 bp and 1600 bp in size, respectively) were then ligated into the EcoRI-PstI restricted pMAL-c2 vector to generate plasmids designated pILL933 and pILL934, respectively. Following induction with IPTG, and purification of the soluble protein on amylose columns, fusion proteins of the expected size (55 kDa for pILL933 [FIG. 17], and 100 kDa for pILL9334) were visualized on SDS-PAGE gels. Each of these corresponded to the fusion of the MalE protein (42.7 kDa) with the second amino acid of each of the Hsp polypeptides. The yield of the expression of the fusion proteins was 100 mg for MalE-HspA and 20 mg for MalE-HspB when prepared from 2 liters of broth culture.

2. Study of the antigenicity of the HspA and HspB fusion proteins, and of the immunogenicity of HspA and HspB in patients infected with *H. pylori:*

In order to determine whether the fusion proteins were still antigenic, each was analyzed by Western blot with rabbit antiserum raised against the MalE protein and a whole-cell extract of *H. pylori* strain 85P. Both fusion proteins were immunoreactive with antibody to MalE (not shown) and with the anti-*H. pylori* antiserum. The anti-*H. pylori* antiserum did not recognize the purified MalE protein (FIG. 18). These results demonstrated that the fusion proteins retained their antigenic properties; in addition, whereas the HspB (SEQ ID NO:30) protein was known to be immunogenic, this is the first demonstration that HspA per se is immunogenic in rabbits.

In the same way, in order to determine whether the HspA (SEQ ID NO:29) and HspB (SEQ ID NO:30) polypeptides were immunogenic in humans, the humoral immune response against HspA (SEQ ID NO:29) and/or HspB (SEQ ID NO:30) in patients infected with *H. pylori* was analyzed and compared to that of uninfected persons using Western immunoblotting assays and enzyme-linked immunosorbent assays (ELISA). None of the 12 sera of the *H. pylori*-negative persons gave a positive immunoblot signal with MalE, MalE-HspA, or MalE-HspB proteins (FIG. 18). In contrast, of 28 sera from *H. pylori*-positive patients, 12 (42.8%) reacted with the HspA (SEQ ID NO:29) protein whilst 20 (71.4%) recognized the HspB (SEQ ID NO:30) protein. All of the sera that recognized HspA also reacted with the HspB (SEQ ID NO:30) protein. No association was observed between the immune response and the clinical presentation of the *H. pylori* infection although such a conclusion might be premature because of the small number of strains analyzed.

3. Nickel binding properties of the fused MalE-HspA protein:

MBP-HspA recombinant protein expressed following induction with IPTG was purified from a whole cell extract by one step purification on nickel affinity column whereas the MBP alone, nor MBP-HspB exhibited this property. FIG. 18 illustrates the one step purification of the MBP-HspA protein that was eluted as a monomer at pH 6.3, and as a monomer at pH 4.5. The unique band seen in panel 7 and the two bands seen in panel 5 were both specifically recognized with anti-HspA rabbit sera. This suggested that the nickel binding property of the fused MBP-HspA protein might be attributed to the C-terminal sequence of HspA, which is rich in histidine and cysteine residues.

V. IMMUNIZATION WITH HELICOBACTER PYLORI GroES HOMOLOG AND UREASE SUBUNIT PROTEINS AFFORDS TOTAL PROTECTION AGAINST MUCOSAL INFECTION

*Helicobacter pylori* is an etiological agent of chronic gastritis and peptic ulceration. Whilst a significant proportion of the population is infected by *H. pylori* bacteria, infected individuals do not always experience symptoms. Recent investigations have established a causal relationship between *H. pylori* and carcinogenesis, which has led to WHO/IARC to classify *H. pylori* as a "definite human carcinogen." Long-term *H. pylori* colonization of the gastric mucosa is involved in the formation of gastric atrophy, which is a known precursor of gastric cancer. It is, therefore, feasible to suggest that prophylaxis against *H. pylori* infection, as well as reducing the incidence of peptic ulcer disease, may also reduce the cases of gastric neoplasia. We believe that for such a strategy to succeed it will be necessary to target properties that are shared by all isolates of *H. pylori.*

Urease activity is a property common to all *H. pylori* isolates and is essential for colonization of the gastric mucosa. *H. pylori* urease is composed of two subunits (UreA (SEQ ID NO:22) and UreB (SEQ ID NO:26)), which from a high molecular weight complex with nickel ions. These subunits are immunodominant antigens and are highly conserved between the different gastric Helicobacter species, including *Helicobacter felis.*

In common with other organisms, *H. pylori* bacteria express heat-shock proteins (SEQ ID NOS:29–30) that share homologies with the GroES and GroEL class of proteins from *Escherichia coli.* We have assessed the heat-shock proteins of *H. pylori* as potential protective antigens in a murine model of gastric Helicobacter infection. Orogastric immunization of mice with recombinant *H. pylori* GroES- and GroEL-like proteins protected 80% (n=20) and 70% (n=10) of animals, respectively, from a challenge dose of $10^4$ Helicobacter bacteria (versus control mice: P=0.0042 and P=0.0904, respectively). All mice (n=19) that were immunized with a dual antigen preparation, consisting of *H. pylori* GroES-like protein and the B subunit of *H. pylori* urease (SEQ ID NO:26), were protected against infection. This represented an equivalent level of protection as that provided by a sonicated Helicobacter extract (P=0.955). Antibodies directed against the recombinant *H. pylori* antigens were predominantly of the IgG, class, suggesting a type 2 T-helper cell (Th-2) response was involved in protection.

Finally, GroES-like and urease subunit B (SEQ ID NO:26) proteins have been identified as potential components of a future *H. pylori* subunit vaccine. Presented below are data showing that the co-administration of an immunization composition of two defined antigens, *H. pylori* UreB (SEQ ID No:26) and HspA (SEQ ID NO:29), was able to confer a level of protection equivalent to that induced by a whole-cell preparation.

EXPERIMENTAL PROCEDURES FOR PART V

A. MATERIALS AND METHODS

1. Bacterial Strains. Media and Growth:

*H. pylori* (85P) was a clinical isolate. Labigne et al., J. Bacteriol, 173, 1920–1931 (1991). *H. felis* (ATCC 49179) was originally isolated from cat gastric mucosa. Lee (1988). Helicobacters were grown on a blood agar medium, containing an antibiotic mixture, and incubated under microaerobic conditions at 37° C. Ferrero (1993). *Escherichia coli* MC1061 cells were grown routinely at 37° C., in solid or liquid Luria medium.

2. Production of Recombinant *H. pylon* antigens:

The genes encoding *H. pylori* urease subunit B and HSP polypeptides (UreB (SEQ ID NO:26), HspA (SEQ ID NO:29) and HspB (SEQ ID NO:30), respectively) were each cloned into the expression vector pMAL-C2 (New England Biolabs Inc.), as previously described. Ferrero (1994) Infect. Immunol. 62, 4981–4989. Recombinant *H. pylori* proteins were expressed as MalE fusions. *E. coli* MC1061 cells harboring the recombinant plasmids were induced with isopropyl-β-D-thiogalactopyranoside (IPTG), and the fusion proteins purified from culture supernatants by affinity and anion exchange chromatography. The purity of recombinant protein preparations was analyzed by SDS-PAGE and by immunoblotting.

3. SDS-PAGE and Immunoblotting Techniques:

Solubilized protein preparations were analyzed on slab gels, comprising a 4.5% acrylamide stacking gel and a 12.5% resolving gel, according to the procedure of Laemmli. Proteins were transferred to nitrocellulose membranes in a Mini Trans-Blot transfer cell (Bio-Rad). Immunoreactants were detected by chemiluminescence (ECL System, Amersham). Ferrero (1994).

Protein concentrations were determined by the Bradford assay (Sigma Chemical Co., St. Louis, Mo.).

4. Animal Experimentation:

Four to 6 wk-old Swiss specific-pathogen-free mice (Centre d'Elevage R. Janvier, Le-Genest-St-Isle, France) were fed a commercial pellet diet with water ad libitum. These mice were previously shown to be free of the murine Helicobacter sp, *Helicobacter muridarum* (Ferrero 1994). Aliquots (0.1 ml) containing $10^4$ *H. felis* bacteria prepared from a low-subculture stock suspension of *H. felis* were administered orogastrically to mice, as previously described (Ferrero 1994). Antigen extracts (50 $\mu$g protein) containing 5 $\mu$g cholera toxin (Sigma) were prepared in 0.1M sodium bicarbonate, prior to delivery to mice. Following sacrifice, stomachs were removed and sera collected.

*H. felis* colonization was assessed using the biopsy urease test and histological techniques. Portions of gastric antrum and body were placed on the surfaces of individual agar plates (1 cm by 1 cm) containing a modified Christensen's medium, to which had been added a Helicobacter-selective antibiotic mixture. The plates were observed for up to 48 h. The remaining two-thirds of each stomach were dissected into longitudinal segments (approximate width 2 mm), which were processed for histopathology (Ferrero 1994).

So as to eliminate observer bias, Giemsa-stained sections were coded prior to histological assessment. For each stomach, all the available tissue (representing up to ⅔ of the stomach) was scrutinized. Protection from *H. felis* colonization was defined as the absence of *H. felis* bacteria from the totality of sections representing each stomach. The severity of gastritis was assessed on the basis of both the degree of mononuclear cell infiltration as well as the distribution of the cell infiltrates. Thus, gastritis was scored according to the following scale: 0, no significant infiltration; 1, infiltration of low numbers of lymphocytes, limited to the muscularis mucosa and the submucosa; 2, infiltration of moderate numbers of lymphocytes in the submucosa, with variable numbers extending into the mucosa; and 3, infiltration of large numbers of lymphocytes in the mucosa, leading to the formation of several aggregates or even nodular structures.

5. ELISA:

Seric IgG antibodies in immunized mice were detected by ELISA. Sauerbaum et al., Molec. Microbiol. 14, 959–974 (1994). Briefly, 96-well plates (Nunc Maxisorb) were coated with a sonicated extract of *H. pylori* (25 μg protein per well). Bound IgG were detected with biotinylated goat anti-mouse antibodies (Amersham) and streptavidin-peroxidase conjugate. Immune complexes were detected by reaction with a solution containing o-phenylenediamine dihydrochloride (Sigma) and hydrogen peroxide. Optical density readings were read at 492 nm in an ELISA plate reader (Titertek).

6. Statistics:

Data were analyzed by $X^2$ and $X_c^2$ (with Yate's correction) tests as appropriate (Campbell et al., Medical Statistics. A Commonsense Approach, 2nd Ed., John Wiley, Chichester (1993)), using the Statview $512^+$ computer software package (BrainPower, Inc., Calabasas, Calif.).

B. RESULTS OF PART V EXPERIMENTS

1. Determination of the Minimum Infectious Dose for *H. felis* in the Mouse:

The *H. felis*-infected mouse has become the model of choice for trials aimed at identifying antigens that may serve in a future *H. pylori* vaccine. Thus far, the size of the *H. felis* inoculum used to challenge immunized animals has not been reconciled with the low *H. pylori* bacterial load that a vaccinated, non-infected individual would be expected to encounter when exposed to *H. pylori*-infected persons. To this end, we have determined the minimum infectious dose required to colonize Swiss mice with *H. felis* (under the conditions in our laboratory). Groups of five mice were thus colonized with inocula prepared from virulent *H. felis* bacteria, which varied from $10^1$ to $10^5$ bacteria. The results are shown in Table 6.

TABLE 6

Determination of the minimum infectious dose for *H. felis* in mice.
Identification of *H. felis* infection in mice at 2 wk post-inoculation

| Inoculum dose* (no. of bacteria) | Urease activity§ (no.) | Culture¶ (no.) |
|---|---|---|
| $10^1$ | 0/5 | 0/5 |
| $10^2$ | 4/5 | 3/5 |
| $10^3$ | 5/5 | 4/5 |
| $10^4$ | 5/5 | 3/5 |
| $10^5$ | 4/5 | 4/5 |

*To determine cell density, various dilutions of a stock *H. felis* culture (which contained predominantly helical-shaped forms) were prepared. Viable *H. felis* bacteria were then enumerated under phase contrast microscopy (magnification factor, 400 x), using a Malassez chamber. Mice were inoculated orogastrically with 0.1 ml of the appropriate inoculum containing virulent *H. felis* bacteria.
§Urease activity was detected in murine gastric biopsies (see Materials and Methods).
¶*H. felis* bacteria were isolated from gastric tissue biopsies after incubation on blood agar plates under microaerobic conditions for 5–7 days, at 37° C.

Whilst an inoculum containing c. $10^1$ bacteria was found to be insufficient to colonize mice, gastric infection in mice was achieved with inocula containing at least $10^2$ bacteria (the minimum infectious dose). A challenge inoculum equivalent to 100 times the minimum infectious dose (i.e. $10^4$ bacteria) was subsequently chosen for all immunoprotection studies.

2. Protection Against *H. felis* Infection in Mice by Immunization with Recombinant HSPs from *H. pylori.*

To demonstrate the presence of HSP homologs in *H. felis*, whole-cell extracts of the organism were immunoblotted and then reacted with hyperimmune rabbit antisera raised against *H. pylori* MalE-HspA and MalE-HspB fusions. Cross-reactive antigens were detected in the *H. felis* extract: the denatured antigens had approximate molecular weights of 15 kDa and 58 kDa, respectively, which corresponded to those of the *H. pylori* HSPs (FIGS. 20A, B). Interestingly, it appeared that the HspA homologs of both *H. pylori* and *H. felis* exist in dimeric forms and these multimeric forms appeared to be resistant to the denaturing effects of SDS.

Recombinant *H. pylori* HSP antigens were assessed for their potential to induce protective mucosal responses in the *H. felis* mouse model. Mice were immunized once per wk (wks 0 to 3) with 50 μg antigen (or 1 mg *H. felis* whole-cell sonicate) and 5 μg cholera toxin. At wk 5, the mice were challenged with an inoculum containing c. $10^4$ *H. felis* bacteria. At wk 7, the mice were sacrificed. The results are reported in Table 7.

TABLE 7

Immunization of mice against *H. felis* infection using *H. pylori* antigens

| Antigens | *H. felis* infectious status of mice: Infected (no.) | Not infected[f] | Grade of gastritis[g]: Infected | Not infected[f] |
|---|---|---|---|---|
| MalE (M) | 14/20 | 30% | 2.57 ± 0.65 (14) | 1.0 ± 0 (6) |
| sonicate[a] | 1/17 | 94 | 3 (1) | 1.31 ± 0.79 (16) |
| M-HspA[b] | 4/20 | 80 | 3 (4) | 1.19 ± 0.83 (16) |
| M-HspB[c] | 3/10 | 70 | 3 (3) | 1.0 ± 0.82 (7) |
| M-UreB[d] | 3/21 | 86 | 2.3 (3) | 1.17 ± 0.38 (18) |
| M-HspA/UreB[e] | 0/19 | 100 | (h) | 1.53 ± 0.70 (19) |
| | | | Σ 2.68 ± 0.56 (25)[h] | 1.28 ± 0.71 (82)i |

[a]P = 0.0003; [b]P = 0.0042; [c]P = 0.0904; [d]P = 0.001; [e]P = 0.0001 compared with the MalE group of animals.
[f]Mice were considered "not infected" when the biopsy urease test was negative, and no *H. felis* bacteria were detected in coded histological sections (see Materials and Methods).
[g]Gastitis was scored from 0 to 3 (see Materials and Methods). Mean scores ± S.D. are presented. Numbers in paragraphs refer to the numbers of animals per group.
[g]Gastitis was scored from 0 to 3 (see Materials and Methods). Mean scores ± S.D. are presented. Numbers in paragraphs refer to the numbers of animals per group.
[h]No mice from this group were infected.
[i]Comparison of score frequencies between immunized animals that became infected and those that were protected (P = 0.0001).
[h]Comparison of individual scores between immunized animals that became infected and those that were protected (P = 0.0001).

Immunization with HspA- or HspB-MalE fusions protected 80% and 70%, respectively, of mice against *H. felis* infection (Table 7). In comparison, 30% of MalE-immunized control mice did not become infected when challenged with the *H. felis* inoculum (P=0.0042 and P=0.0904, respectively).

Co-administration of recombinant *H. pylori* UreB (SEQ ID NO:26) and HspA (SEQ ID NO:29) antigens to mice resulted in 100% protection, which compared with a protection rate of 86% in those animals that had received the UreB antigen alone (Table 7). The level of protection afforded by the co-administration of MalE-UreB and MalE-HspA was equivalent to that obtained in the group of *H. felis* sonicate-immunized animals (P=0.955; Table 7).

3. Serological Responses Following Immunization with Recombinant HSPs and Urease Polypeptides:

Measurement of *H. pylori*-specific IgG antibodies in the serum of immunized mice demonstrated that virtually all of the animals developed strong humoral responses to the administered *H. pylori* urease and heat-shock antigens. As would be predicted of a mucosal immune response, serum antibodies directed against these antigens appeared to be primarily of the $IgG_1$ idiotype (FIG. 19). This finding was indicative of a predominantly type 2 T-helper cell (Th-2) response. Consistent with this, serum levels of *H. pylori*-specific $IgG_{2a}$, antibodies, which are normally associated with Th-1 type responses, were relatively low and varied depending upon the antigen administered: HspA appeared to induce particularly weak $IgG_{2a}$ serum responses (FIG. 19). These differences were considered to be specific to the *H. pylori* antigenic components of the recombinant proteins, since approximately equivalent levels of $IgG_1$ and $IgG_{2a}$, antibody idiotypes were detected when MalE-specific antibodies were measured (unpublished data). No qualitative nor quantitative differences could be found between IgG serum responses and the infectious status of the mice at sacrifice.

4. Cellular Responses Induced in Mice following Immunization:

Histological assessment of gastric mucosa tissue from the immunized mice revealed low levels of mononuclear cells (mean inflammation score: 1.28±0.71) for those mice which were protected from an *H. felis* infection (Table 7). In contrast, those immunized animals that became infected tended to have a significantly more severe form of lymphocytic gastritis in which lymphoid follicular structures were often observed (mean score: 2.68±0.56; P=0.0001). Large numbers of mononuclear cells were observed in the gastric tissue of *H. felis*-colonized mice from the MalE-immunized group.

In this study, we tested an antigenic preparation consisting of two recombinant proteins, *H. pylori* UreB (SEQ ID NO:26) and HspA (SEQ ID NO:29), and showed that, under identical experimental conditions, it was as effective as a whole-cell extract of *H. felis* in protecting against *H. felis* infection in mice. We observed in both this study, and in an independent one in which immunized mice were not challenged with *H. felis* (unpublished data), that the administration of *H. pylori* Hsp antigens did not appear to be associated with an unduly severe pathology.

The evidence to date suggests that a mild gastric inflammation may be a necessary prerequisite for a successful orogastric immunization. Michetti et al., Gastroenterology 107, 1002–1011 (1994); Ferrero (1994). Activation of a Th-2 immune response is normally associated with the migration of both IgA-secreting B lymphocytes and $T_H$ lymphocytes to effector tissue sites. Staats et al., Curr. Opin. Immunol. 6, 572–583 (1994). It is, therefore, perhaps not surprising that orogastric immunization of mice results in a mild degree of lymphocytic gastritis. Administration of cholera toxin may contribute to this inflammation: in vitro experiments showed that cholera toxin alone increased the proliferation of murine B and T lymphocytes. Elson, Infect. Immun. 60, 2874–2879 (1992). It is also likely that the antigenic load provided by the *H. felis* bacterial challenge exacerbates the inflammation: immunized mice that became infected with *H. felis* displayed a higher degree of gastritis than those immunized animals that were protected against *H. felis* infection. However, as this difference was also observed amongst the MalE-immunized group of mice, it is unlikely that cross-reactivity between the recombinant *H. pylori* antigens and the *H. felis* bacteria accounted for the severe pathology seen in those immunized mice that were not protected. Eaton and Krakowka also observed that immunized piglets, which were not protected against *H. pylori* infection, developed severe gastritis. Eaton et al., Gastroenterology 103, 1580–1586 (1992).

*H. pylori* HspA (SEQ ID NO:29) is particularly appealing as a vaccine component because, in contrast with HspB (SEQ ID NO:30), it possesses a unique domain at its C-terminus, which is absent from other known heat-shock homologs, including those of eucaryotic organisms. The C-terminus of *H. pylori* HspA (SEQ ID NO:29) consists of a series of 26 amino acids (out of a total of 118 amino acids), and undoubtedly confers a unique conformational structure to this polypeptide. The capacity of *H. pylori* HspA (SEQ ID NO:29) to bind to nickel ions should facilitate the large-scale purification of this polypeptide by metal affinity chromatography.

Evidence from the immunoprotection studies and immunoblot analyses suggest that *H. felis* produces a GroES homolog. Whether this protein also contains the C-terminal nickel-binding domain is currently a subject of investigation in our laboratory. It is noteworthy that these Helicobacter GroES homologs seem to exist as dimeric forms, a feature that has also been described for other known nickel-binding proteins, such as the UreE proteins from *Proteus mirabilis*, Sriwanthana et al., J. Bacteriol, 176, 6836–6841 (1994), and *Klebsiella aerogenes*, Lee et al., Protein Sci. 2, 1042–1052 (1993).

Thus, the immunization composition of this invention preferably contains *H. pylori* UreB (SEQ ID NO:26) and HspA (SEQ ID NO:29) as immunogens. The UreB (SEQ ID NO:26) and HspA (SEQ ID NO:29) can be isolated from *H. pylori* lysates or sonicates, but are preferably free of other *H. pylori* antigens, including multimeric urease. Thus, in one embodiment of the invention the UreB (SEQ ID NO:26) and HspA (SEQ ID NO:29) are substantially free of UreA (SEQ ID NO:22). It is particularly preferred that the UreB (SEQ ID NO:26) and the HspA (SEQ ID NO:29) be prepared by recombinant techniques. The resulting recombinant antigens are substantially free of multimeric urease and other *H. pylori* antigens.

The immunization composition of the invention can also include an adjuvant in an amount sufficient to enhance the magnitude or duration of the immune response in the host, or to enhance the qualitative response in the subject, such as by stimulating antibodies of different immunoglobulin classes than those stimulated by the immunogen. The adjuvant should efficiently elicit cell-mediated or humoral immune responses to antigens without systemic or localized irritation of the host system. Preferably, the adjuvant has low pyrogenicity.

Well known adjuvant formulations for human or veterinary applications can be employed. Such adjuvants can be based on emulsions, with or without mycobacteria, or adjuvants based on adsorption of antigens to aluminum salts, especially aluminum hydroxide or aluminum phosphate. Among these adjuvants are oil adjuvants based on mineral, animal, and vegetable oils. Oil based adjuvants are useful for increasing humoral responses of animals to vaccine antigens, and certain oil-based adjuvants have been tested for human use. Typical adjuvants are Freund's complete adjuvant and Freund's incomplete adjuvant.

Suitable adjuvants that have been developed more recently, include liposomes, immune-stimulating complexes (ISCOMs), and squalene or squalene emulsions. Surface active agents having adjuvant activity can also be employed. These include saponin-like Quil A molecules in ISCOMs and Pluronic® block copolymers that are used to make stable squalene emulsions. Saponins are surface-active agents widely distributed in plants.

Analogs of muramyl dipeptide (MDP) or muramyl tripeptide (MTP), such as threonine analog of MDP and lipopolysaccharide (LPS) having adjuvant activity and reduced side effects, are also suitable for use as adjuvants. Synthetic analogs of MDP and the monophosphoryl derivative of lipid A are also known for their adjuvant activity and reduced pyrogenicity. A particularly suitable formulation is Syntex Adjuvant Formulation-1 or SAF-1, which combines the threonyl analog of MDP in a vehicle comprised of Pluronic L-121 triblock polymer with squalene and a small proportion of Tween 80 as an emulsifying detergent. The preferred adjuvants for use in humans are MDP and its analogs, with or without squalene, saponins, and the monophosphoryl derivative of lipid A. When an adjuvant is combined with the immunogen in the composition and method of the invention, a further enhancement in immune response is observed.

A preferred route of administering the composition of the invention to a host is mucosal. Oral administration is the particularly preferred mode of administration because of its simplicity and because it is relatively non-invasive. It will be understood that the immunogenic composition of the invention can also be employed in a vaccine. An alternative mucosal adjuvant could be used. All or part of the cholera (CT) or *E. coli* LT holotoxins in either toxic or detoxified forms are examples.

The composition of the invention can be incorporated into any suitable delivery system. For example, the antigen and adjuvant can be combined with a pharmaceutically acceptable liquid vehicle, such as water, buffered saline, or edible animal or vegetable oil. The composition can be combined with one or more suitable pharmaceutically acceptable excipients or core materials, such as cellulose, cellulose derivatives, sucrose, gelatin, Starch 1500, NuTab, lactose, malto-dextrin, talc, Cabosil, magnesium stearate, alginate, Actisol, PEG 400, Myvacet, Triacetine, syrup, oil, sorbitol, mannitol, and Plasdone. This list is not intended to be exhaustive or limiting; alternative or additional excipients or core materials can also be used.

It will also be understood that the compositions of the invention can be formulated to include chemical agents that are capable of neutralizing stomach pH. Suitable neutralizing agents include $H_2$ antagonists, proton pump inhibitors, bicarbonate of soda, calcium carbonate, and aluminum hydroxide.

The composition of the invention can be utilized in the form of elixirs, solutions, suspensions, syrups, aerosols, and the like. The composition can also be prepared in dosage units suitable for oral or parenteral administration, such as particles, granules, beads, tablets, hard gelatin capsules, and soft gelatin capsules.

The immunogen and adjuvant are employed in a combined amount to provide an immune response against an infectious agent. This can be determined by estimating seroconversion, that is, the levels of antibody before and after immunization. If the host has a preexisting antibody titer to the antigen, the success of immunization can be determined by the extent of increase in the level of specific antibody. In cases where there is no correlation between seroconversion and protection, cell-mediated immune response can be monitored.

The amount of antigen and adjuvant per dosage unit will depend on the desired dose and the frequency of administration. In one embodiment, each dosage unit contains an amount of antigen effective to protect the animal against disease following exposure to the pathogen. The dose can be defined as the amount of immunogen necessary to raise an immune response against *H. pylori* infection in an individual. As an example, the immunization schedule in animals (mice) consists of 4 administrations (one/week). Each oral dose unit (one per week) comprises 250 to 900 micrograms of UreB and 250 to 900 micrograms of HspA and 25 to 90 micrograms of adjuvant. A suitable weight ratio of UreB:HspA:adjuvant is 1:1:0.1, but it will be understood that other ratios of ingredients can be employed. The average weight of a mouse is 20 g and one can calculate for one kilogram of other animal or a human patient to be immunized the equivalent dose unit. The precise composition will necessarily vary depending on the antigen and adjuvant selected, the species to be immunized, and other factors, and it is within the capacity of one with ordinary skill in the art to search for an optimal formulation.

The immunogenic composition can be administered before or after infection. A booster dose can comprise the antigen in an amount sufficient to enhance the initial immune response. It has to be adapted to each protocol depending on the antigen and the host. Multiple doses may be more appropriate for children and for individuals with no known prior exposure.

The immunogenic composition containing UreB and HspA can be administered to an infected or non-infected animal. Thus, it will be understood that this invention can be employed for the prophylactic, therapeutic, or curative treatment of any animal in need thereof, such as dogs, cats, poultry, pigs, horses, and cattle, and especially mammals, such as primates, including humans, using UreB and HspA or the species equivalent thereof.

Finally, a preferred embodiment of the previously described antibodies of the invention comprises monoclonal antibodies, polyclonal antibodies, or fragments of such antibodies that immunologically recognize UreB, HspA, or mixtures of UreB and HspA. Antibodies and antibody fragments that are specific for these polypeptides and their immunologically recognizable fragments can be prepared by the techniques described above.

Inasmuch as the present invention is subject to many variations, modifications, and changes in details, it is intended that all subject matter discussed above or shown in the accompanying drawings be interpreted as illustrative and not in a limiting sense. Such modifications and variations are included within the scope of this invention as defined by the following claims.

REFERENCES

Boyer, H. W., and Roulland-Dussoix, D. (1969) A complementation analysis of the restriction and modification of DNA in *Escherichia coli*. J Mol Biol 41:459–472.

Chen, M., Lee, A., and Hazell, S. L. (1992) Immunization against gastric helicobacter infection in a *mouse/Helicobacter felis model. Lancet* 339:1120–1121.

Corthesy-Theulaz, I. et al (1993), Acta Gastro-Enterol. Belgica Suppl., vol. 56, p 64 (VIth Workshop on Gastroduodenal pathology and *H. pylori*).

Cover, T. L., Puryear, W.; Perez-Perez, G. J., and Blaser, M. (1991) Effect of urease on HeLa cell vacuolation induced by *Helicobacter pylori* cytotoxin. *Infect Immun* 59:1264–1270.

Cussac, V., Ferrero, R. L., and Labigne, A. (1992) Expression of *Helicobacter pylori* urease genes in *Escherichia coli* grown under nitrogen-limiting conditions. *J Bacteriol* 174:2466–2473.

Davin, C. et al., Abstract A-304, Gastroenterology 1993 (Abstract supplement).

Dick-Hegedus, E., and Lee, A. (1991) The use of a mouse model to examine anti-*Helicobacter pylori* agents. *Scand J Gastroenterol* 26:909–915.

Dick E., Lee A., Watson G., and O'Rourke J. (1989) Use of the mouse for the isolation and investigation of stomach-associated, spiral-helical shaped bacteria from man and other animals. *J Med Microbiol* 29:55–62.

Dunn, B. E., R. M., Roop II, C.-C. Sung, S. A. Sharma, G. I. Perez-Perez, and M. J. Blaser, 1992. Identification and purification of a cpn60 heat shock protein homolog from *Helicobacter pylori*. Infect Immun. 60:1946–1951.

Eaton, K. A., Brooks, C. L., Morgan, D. R., and Krakowka, S. (1991) Essential role of urease in pathogenesis of gastritis induced by *Helicobacter pylori* in gnotobiotic piglets. Infect Immun 59:2470–2475.

Evans, D. J., Evans, D. G., Engstrand, L. and Graham, D. Y. (1992) Heat shock protein of *Helicobacter pylori*. Infect Immun 60:2125–2127.

Ferrero, R. L., and Lee, A. (1991) The importance of urease in acid protection for the gastric-colonising bacteria *Helicobacter pylori* and *Helicobacter felis* sp. nov. *Microb Ecol Hlth Dis* 4:121–134.

Ferrero, R. L., Cussac, V., Courcoux, P. and Labigne, A. (1992) Construction of isogenic urease-negative mutants of *Helicobacter pylori* by allelic exchange. *J Bacteriol* 174:4212–4217.

Ferrero, R. L. and Labigne, A. (1993) Cloning, expression and sequencing of *Helicobacter felis* urease genes. Molec. Microbiol. 9, 323–333.

Ferrero, R. L. et al. (1994) Recombinant antigens prepared from Urease Subunits of Helicobacter spp. Evidence of Protection in a Mouse model of Gastric infection. *Inf. and Immunity,* 62, 4981–4989.

Freedburg, A. S., and Barron, L. E. (1940) The presence of spirochetes in human gastric mucosa. *American Journal of Digestive Diseases* 7:443–445.

Goodwin, C. S., Armstrong, J. A., Chilvers, T., Peters, M., Collins, M. D., Sly, L., McConnell, W., and Harper, W. E. S. (1989) Transfer of Campylobacter pylori comb. nov. and *Helicobacter mustelae* comb. nov., respectively. *Int J Syst Bacteriol* 39:397–405.

Hazell, S. L., and Lee, A. (1986) *Campylobacter pyloridis*, urease, hydrogen ion back diffusion, and gastric ulcers. *Lancet ii:*15–17.

Hazell, S. L., Borody, T. J., Gal, A., and Lee, A. (1987) *Campylobacter pyloridis* gastritis I: Detection of urease as a marker of bacterial colonization and gastritis. *Am J Gastroenterol* 82:292–296.

Hu, L-T, Foxall, P. A., Russell, R., and Mobley, H. L. T. (1992) Purification of recombinant *Helicobacter pylori urease apoenzyme encoded by ureA and ureB. InfectImmun.* 60:2657–2666.

Jones, B. D., and Mobley, H. L. T. (1989) *Proteus mirabilis* urease: nucleotide sequence determination and comparison with jack bean urease. *J Bacteriol* 171:6414–6422.

Krakowka, S., Morgan D. R., Kraft W. G., and Leunk R. D. (1987) Establishment of gastric *Campylobacter pylori* infection in the neonatal gnotobiotic piglet. Infect Immun 55:2789–2796.

Labigne-Roussel, A., Courcoux, P., and Tompkins, L. (1988) Gene disruption and replacement as a feasible approach for mutagenesis of *Campylobacter jejuni. J Bacteriol* 170:1704–1708.

Labigne, A., Cussac, V., and Courcoux, P. (1991) Shuttle cloning and nucleotide sequences of *Helicobacter pylori* genes responsible for urease activity. *J Bacteriol* 173:1920–1931.

Labigne, A., Courcoux, P., and Tompkins, L. (1992) Cloning of *Campylobacter jejuni* genes required for leucine biosynthesis, and construction of leu-negative mutant of *C. jejuni* by shuttle transposon mutagenesis. *Res Microb* 143:15–26.

Laemmli, E. K. (1970) Cleavage of structural proteins during the assembly of the head of bacteriophage T4. *Nature* 227:680–685.

Lee, A., Hazell, S. L., O'Rourke, J., and Kouprach, S. (1988) Isolation of a spiral-shaped bacterium from the cat stomach. *Infect Immun* 56:2843–2850.

Lee, A., Fox, J. G., Otto, G., and Murphy, J. (1990) A small animal model of human *Helicobacter pylori* active chronic gastritis. *Gastroenterol* 99:1315–1323.

Lee, M. H., Mulrooney, S. B., Renner, M. J., Marckowicz, Y., and Hausinger, R. P. (1992) Klebsiella aerogenes urease gene cluster: Sequence of ure D and demonstration that four accessory genes (ure D, ure E, ure F, and ure G) are involved in nikel metallocenter biosynthesis. *J Bacteriol* 174:4324–4330.

Luger, A., and Neuberger, H. (1921) Uber spirochatenbefunde im magensaft und der diagnostische Bedeutung f ür das carcinoma ventriculi. *Zeit Klin* Med 92:54.

Mai, U. E. H., Perez-Perez, G. I., Allen, J. B., Wahl, S. M., Blaser, M. J., and Smith, P. D. (1992) surface proteins from *Helicobacter pylori* exhibit chemotactic activity for human leukocytes and are present in gastric mucosa. *J Exp Med* 175:517–525.

Maniatis, T., Fritsch, E., and Sambrook, J. (1983) Molecular cloning: a laboratory manual. Cold Spring Harbor Laboratory, Cold Spring Harbor N.Y.

Marshall, B.-J., Royce, H., Annear, D. I., Goodwin, C. D., Pearman, J. W., Warren, J. R., and Armstrong, J. A. (1984) Original isolation of *Campylobacter pyloridis* from human gastric mucosa. *Microbios Lett* 25:83–88.

Marshall, B. J., Barrett, L. J., Prakash, C., McCallem, R. W., and Guerrant, R. L. (1990) Urea protects *Helicobacter* (*Campylobacter*) *pylori* from the bactericidal effect of acid. *Gastroenterol* 99:697–702.

Meissing, J., and Vieira, J. (1982) A new pair of M13 vectors for selecting either DNA strand of double-digest restriction fragments. *Gene* 19:269–276.

Mobley, H. L. T., and Hausinger, R. P. (1989) Microbial ureases: significance, regulation, and molecular characterisation. *Microbiol Rev* 53:85–108.

Newell, D. G., Lee, A.; Hawtin, P. R., Hudson, M. J., Stacey, A. R., and Fox, J. (1989) Antigenic conservation of the ureases of spiral- and helical-shaped bacteria colonising the stomachs of man and animals. *FEMS Microbiol Lett* 65:183–186.

Nomura, A., Stermmermann, G. N., Ghyou, P-H., Kato, I., Perez-Perez, G. I., and Blaser, M. J. (1991) *Helicobacter pylori* infection and gastric carcinoma among Japanese Americans in Hawaii. *N Eng J Med* 325:1132–1136.

Parsonnet, J., Friedman, G. D., Vanderstee, D. P., Chang, Y., Vogelman, J. H., Orentreich, N., and R. Sibley (1991) *Helicobacter pylori* infection and the risk of gastric carcinoma. *N Eng J Med* 325:1127–1131.

Paster, B. J., Lee, A., Dewhirst, F. E., Fox, J. G., Tordoff, L. A., Fraser, G. J., O'Rourke, J. L., Taylor, N. S., and Ferrero, R. (1990) The phylogeny of *Helicobacter felis* sp. nov., *Helicobacter mustalae*, and related bacteria. *Int J Syst Bacteriol* 41:31–38.

Peterson, W. L. (1991) *Helicobacter pylori* and peptic ulcer disease. *N Engl J Med* 324:1043–1047.

Radin, J. M., Eaton, K. A., Krakowka, S., Morgan, D. R., Lee, A., Otto, G., and Fox, J. G. (1990) *Helicobacter pylori* infection in gnotobiotic dogs. *Infect Immun* 58:2606–2612.

Salomon, H. (1896) Ueber das Spirillem des Saugetiermagens und sein Verhalten zu den Belegzellen. *Zentral Bakteriol Parasiten Infektion* 19:433–442.

Sanger, F., Nicklen, S., and Coulson, A. R. (1977) DNA sequencing with chain terminating inhibitors. *Proc Natl Acad Sci USA* 74:5463–5467.

Shine, J., and Dalgarno, L. (1974) The 3'-terminal sequence of *Escherichia coli* 16S ribosomal RNA: complementarity to nonsense triplets and ribosome binding sites. *Proc Natl Acad Sci USA* 71:1342–1346.

Sidebotham, R. L., and Baron, J. H. (1990) Hypothesis: *Helicobacter pylori*, urease, mucus, and gastric ulcer. *Lancet* 335:193–195.

Smoot, D. T., Mobley, H. L. T., Chippendale, G. R., Lewinson, J. F., and Resau, J. H. (1990) *Helicobacter pylori* urease activity is toxic to human gastric epithelial cells. *Infect Immun* 58:1992–1994.

Solnick, J. V., et al., *Infec. and Immunity*, May 1994, p 1631–1638.

Suerbaum, S. et al., (1994). *Helicobacter pylori* hspA-hspB heat-shock gene cluster; nucleotide sequence, expression, putative function and immunogenicity. Mol. Microb. 14(5), 959–979.

Towbin, H., Staehelin, T., and Gordon, J. (1979) Electrophoretic transfer of proteins from polyacrylamide gels to nitrocellulose sheets: procedure and some applications. *Proc Natl Acad Sci* 76:4350–4354.

Turbett, G. R., Nandapalan, N., Campbell, I. G., Nikoletti, S. M., and Mee, B. J. (1991) Characterization of the urease from *Helicobacter pylori* and comparison with the ureases from related spiral gastric bacteria. *FEMS Microbiol Immunol* 76:19–24. Turbett, G. R., Hoj, P., Horne, R., and Mee, B. J. (1992) Purification and characterization of the urease enzymes of Helicobacter species from humans and animals. *Infect Immun* 60:5259–5266.

We claim:

1. An immunogenic composition, capable of inducing antibodies against Helicobacter infection, comprising:

i) at least one urease structural polypeptide encoded by the UreB gene of *Helicobacter pylori* or *Helicobacter felis* or immunogenic fragment thereof comprising at least six consecutive amino acids; and ii) at least one heat shock protein encoded by the Hsp A gene of *Helicobacter pylori* or *Helicobacter felis* or immunogenic fragment thereof, comprising at least 6 consecutive amino acids, said composition being substantially free of other *Helicobacter pylori* or *Helicobacter felis* proteins.

2. An immunogenic composition comprising an immunizing amount of a mixture of *Helicobacter pylori* or *Helicobacter felis* antigens, wherein said mixture consists essentially of UreB and HspA of *H. pylori* or *H. felis* substantially free of other *H. pylori* or *H felis* proteins.

3. The immunogenic composition according to claim 1 or claim 2, wherein the HspA is encoded by the HspA gene of plasmid pILL689 (CNCM I-1356).

4. The immunogenic composition according to claim 1 or claim 2, wherein the HspA comprises the amino acid sequence of SEQ ID NO: 1 or an immunogenic fragment thereof having at least 6 consecutive amino acids.

5. The immunogenic composition according to claim 1 or claim 2, additionally comprising an adjuvant.

6. The immunogenic composition according to claim 1 or claim 2, wherein said composition produces an immunogenic effect when administered to a mammal, wherein the immunogenic effect is substantially the same as the immunogenic effect produced in the mammal when a total cell extract of *Helicobacter pylori* or *Helicobacter felis* is administered to said mammal.

7. A method of inducing an immune response in an animal, comprising the step of administering to the animal an immunizing amount of a composition according to claim 1 or claim 2.

8. The method according to claim 7, wherein the animal is a cat or a dog.

9. The method according to claim 7, wherein the animal is a human.

10. A pharmaceutical composition for use in a vaccine against *Helicobacter pylori* or *Helicobacter felis,* comprising the immunogenic composition according to claim 1 or claim 2, in combination with a pharmaceutically acceptable carrier.

* * * * *